(12) United States Patent
Chakravarthy et al.

(10) Patent No.: US 11,702,466 B2
(45) Date of Patent: Jul. 18, 2023

(54) FUSION PROTEIN COMPRISING A BLOOD-BRAIN BARRIER (BBB)-CROSSING SINGLE DOMAIN ANTIBODY FC5, AN IMMUNOGLOBULIN FC FRAGMENT AND A BETA-AMYLOID BINDING POLYPEPTIDE (ABP)

(71) Applicant: National Research Council of Canada, Ottawa (CA)

(72) Inventors: Balu Chakravarthy, Ottawa (CA); Danica Stanimirovic, Ottawa (CA); Yves Durocher, Montreal (CA)

(73) Assignee: National Research Council of Canada, Ottawa (CA)

( * ) Notice: Subject to any disclaimer, the term of this patent is extended or adjusted under 35 U.S.C. 154(b) by 241 days.

(21) Appl. No.: 16/481,898

(22) PCT Filed: Jan. 30, 2018

(86) PCT No.: PCT/IB2018/050576
§ 371 (c)(1),
(2) Date: Jul. 30, 2019

(87) PCT Pub. No.: WO2018/138709
PCT Pub. Date: Aug. 2, 2018

(65) Prior Publication Data
US 2019/0352383 A1 Nov. 21, 2019

Related U.S. Application Data

(60) Provisional application No. 62/530,980, filed on Jul. 11, 2017, provisional application No. 62/452,015, filed on Jan. 30, 2017.

(51) Int. Cl.
| | | |
|---|---|---|
| *C07K 16/46* | (2006.01) | |
| *C07K 16/00* | (2006.01) | |
| *C07K 14/00* | (2006.01) | |
| *A61K 39/00* | (2006.01) | |
| *A61K 38/00* | (2006.01) | |
| *C07K 16/18* | (2006.01) | |
| *A61K 9/00* | (2006.01) | |
| *C07K 14/47* | (2006.01) | |

(52) U.S. Cl.
CPC ............ *C07K 16/18* (2013.01); *A61K 9/0019* (2013.01); *C07K 14/4711* (2013.01); *C07K 2317/24* (2013.01); *C07K 2317/565* (2013.01); *C07K 2317/569* (2013.01); *C07K 2319/10* (2013.01); *C07K 2319/30* (2013.01); *C07K 2319/33* (2013.01); *C07K 2319/70* (2013.01)

(58) Field of Classification Search
CPC .......... C07K 2317/569; C07K 2317/22; C07K 2317/24; C07K 2317/565; C07K 16/2863; C07K 16/28; C07K 2317/52; C07K 16/2803; C07K 2317/622; C07K 2319/33; C07K 2319/70; C07K 2317/70; C07K 2319/00; C07K 14/4711; A61K 2039/505; A61K 47/6849; A61P 25/28
See application file for complete search history.

(56) References Cited

U.S. PATENT DOCUMENTS

| | | | | |
|---|---|---|---|---|
| 5,385,915 | A | 1/1995 | Buxbaum et al. | |
| 6,943,241 | B2 * | 9/2005 | Isogai | C07K 14/47 435/252.1 |
| 7,615,626 | B2 * | 11/2009 | Van Rompaey | A61P 19/00 536/24.5 |
| 7,745,391 | B2 * | 6/2010 | Mintz | A61P 37/00 514/19.3 |
| 7,943,129 | B2 * | 5/2011 | Muruganandam | C12N 15/1037 424/130.1 |
| 8,257,705 | B2 * | 9/2012 | Tanha | C40B 40/02 424/133.1 |
| 8,318,137 | B2 * | 11/2012 | Van Rompaey | A61P 19/00 424/9.2 |
| 8,323,925 | B2 * | 12/2012 | Chakravarthy | C07K 14/4711 524/2 |
| 8,383,107 | B2 * | 2/2013 | Muruganandam | C07K 16/28 424/130.1 |
| 8,715,659 | B2 * | 5/2014 | Muruganandam | C07K 16/00 424/130.1 |
| 8,883,425 | B2 * | 11/2014 | Van Rompaney | A61P 19/08 435/6.13 |
| 9,676,849 | B2 * | 6/2017 | Farrington | C07K 16/28 |

(Continued)

FOREIGN PATENT DOCUMENTS

| | | |
|---|---|---|
| JP | 2015-509097 | 3/2015 |
| JP | 2015-528452 | 9/2015 |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Abbott, Blood-brain barrier structure and function and the challenges for CNS drug delivery. J Inherit Metab Dis. 2013;36(3):437-449. doi:10.1007/s10545-013-9608-0.

(Continued)

*Primary Examiner* — Chang-Yu Wang
(74) *Attorney, Agent, or Firm* — Cooley LLP

(57) ABSTRACT

A brain-penetrating composition of amyloid-ß binding peptide is disclosed. This may be useful in the treatment of Alzheimer's disease, for example as a bifunctional molecule, comprising a blood-brain barrier crossing antibody and an amyloid-ß targeting peptide linked via an Fc fragment that is able to transmigrate across the blood-brain barrier into the brain, and compositions comprising same. Methods of using this composition for treating Alzheimer's disease are disclosed.

8 Claims, 29 Drawing Sheets
Specification includes a Sequence Listing.

(56) References Cited

U.S. PATENT DOCUMENTS

| | | | | |
|---|---|---|---|---|
| 10,100,117 | B2* | 10/2018 | Stanimirovic | C07K 16/465 |
| 10,106,614 | B2* | 10/2018 | Stanimirovic | A61K 47/6811 |
| 10,112,998 | B2* | 10/2018 | Stanimirovic | G01N 33/74 |
| 10,184,008 | B2* | 1/2019 | Webster | A61P 25/04 |
| 10,563,263 | B2* | 2/2020 | Shiftman | A61P 9/10 |
| 10,738,115 | B2* | 8/2020 | Stanimirovic | A61K 47/6849 |
| 10,906,973 | B2* | 2/2021 | Stanimirovic | C07K 16/28 |
| 2003/0190598 | A1* | 10/2003 | Tanha | C12N 15/1037 435/5 |
| 2004/0161738 | A1* | 8/2004 | Muruganandam | C07K 16/28 435/5 |
| 2009/0162422 | A1* | 6/2009 | Muruganandam | C12N 15/1037 424/450 |
| 2011/0171720 | A1* | 7/2011 | Muruganandam | C12N 15/1037 435/235.1 |
| 2011/0300141 | A1* | 12/2011 | Chakravarthy | C07K 14/4711 424/134.1 |
| 2013/0150561 | A1* | 6/2013 | Muruganandam | C40B 40/02 530/389.1 |
| 2013/0272958 | A1 | 10/2013 | Zhang et al. | |
| 2015/0210762 | A1 | 7/2015 | Farrington et al. | |
| 2017/0015748 | A1* | 1/2017 | Stanimirovic | G01N 33/57492 |
| 2017/0015749 | A1* | 1/2017 | Stanimirovic | A61P 25/16 |
| 2017/0022277 | A1* | 1/2017 | Stanimirovic | A61K 49/0002 |
| 2019/0241653 | A1* | 8/2019 | Stanimirovic | A61K 47/6849 |
| 2019/0352383 | A1* | 11/2019 | Chakravarthy | C07K 16/1282 |
| 2020/0095316 | A1* | 3/2020 | Stanimirovic | C07K 17/00 |

FOREIGN PATENT DOCUMENTS

| | | |
|---|---|---|
| JP | 2017512464 A | 5/2017 |
| JP | 2017513461 A | 6/2017 |
| JP | 2017514456 A | 6/2017 |
| WO | WO 1995/004069 A1 | 2/1995 |
| WO | WO 01/88088 A1 | 11/2001 |
| WO | WO 2002/057445 A1 | 7/2002 |
| WO | WO 02/086122 A1 | 10/2002 |
| WO | WO 2003/046560 A2 | 6/2003 |
| WO | WO 2004/076670 A1 | 9/2004 |
| WO | WO 2006/133566 A1 | 12/2006 |
| WO | WO 2007/036021 A1 | 4/2007 |
| WO | WO 2011/127580 A1 | 10/2011 |
| WO | WO 2015/131256 A1 | 9/2015 |
| WO | WO 2015/131257 A1 | 9/2015 |
| WO | WO 2015/131258 A1 | 9/2015 |
| WO | WO 2016/097315 A2 | 6/2016 |
| WO | WO 2018/007950 A1 | 1/2018 |
| WO | WO 2018/109663 | 6/2018 |
| WO | WO2018/109663 * | 6/2018 |
| WO | WO 2018/138709 | 8/2018 |
| WO | WO 2019/150183 | 8/2019 |

OTHER PUBLICATIONS

Abulrob et al., The blood-brain barrier transmigrating single domain antibody: mechanisms of transport and antigenic epitopes in human brain endothelial cells. J Neurochem. 2005;95(4):1201-1214. doi:10.1111/j.1471-4159.2005.03463.x.

Alzheimer's Association, 2015 Alzheimer's disease facts and figures. Alzheimer's & Dementia. 2015;11:332-384.

Arbabi Ghahroudi et al., Selection and identification of single domain antibody fragments from camel heavy-chain antibodies. FEBS Lett. 1997;414(3):521-526. doi:10.1016/s0014-5793(97)01062-4.

Ballard et al., Alzheimer's disease. Lancet. 2011;377(9770):1019-1031. doi:10.1016/S0140-6736(10)61349-9.

Barage et al., Amyloid cascade hypothesis: Pathogenesis and therapeutic strategies in Alzheimer's disease. Neuropeptides. 2015;52:1-18. doi:10.1016/j.npep.2015.06.008.

Bard et al., Peripherally administered antibodies against amyloid beta-peptide enter the central nervous system and reduce pathology in a mouse model of Alzheimer disease. Nat Med. 2000;6(8):916-919. doi:10.1038/78682.

Bell et al., Differential tumor-targeting abilities of three single-domain antibody formats. Cancer Lett. 2010;289(1):81-90. doi:10.1016/j.canlet.2009.08.003.

Caram-Salas et al., In vitro and in vivo methods for assessing FcRn-mediated reverse transcytosis across the blood-brain barrier. Methods Mol Biol. 2011;763:383-401. doi:10.1007/978-1-61779-191-8_26.

Chothia et al., Canonical structures for the hypervariable regions of immunoglobulins. J Mol Biol. 1987;196(4):901-917. doi: 10.1016/0022-2836(87)90412-8.

Davies et al., Affinity improvement of single antibody VH domains: residues in all three hypervariable regions affect antigen binding. Immunotechnology. 1996;2(3):169-179. doi:10.1016/s1380-2933(96)00045-0.

De-Paula et al., Alzheimer's disease. Subcell Biochem. 2012;65:329-352. doi:10.1007/978-94-007-5416-4_14.

Delagarza et al., Pharmacologic treatment of Alzheimer's disease: an update. Am Fam Physician. 2003;68(7):1365-1372..

Dumoulin et al., Single-domain antibody fragments with high conformational stability. Protein Sci. 2002;11(3):500-515. doi:10.1110/ps.34602.

Durocher et al., High-level and high-throughput recombinant protein production by transient transfection of suspension-growing human 293-EBNA1 cells. Nucleic Acids Res. 2002;30(2):E9. doi:10.1093/nar/30.2.e9.

Eisenberg et al., Analysis of membrane and surface protein sequences with the hydrophobic moment plot. J Mol Biol. 1984;179(1):125-142. doi:10.1016/0022-2836(84)90309-7.

Farrington et al., A novel platform for engineering blood-brain barrier-crossing bispecific biologies. FASEB J. 2014;28(11):4764-4778. doi:10.1096/fj.14-253369.

Garberg et al., In vitro models for the blood-brain barrier. Toxicol In Vitro. 2005;19(3):299-334. doi:10.1016/j.tiv.2004.06.011.

Gergov et al., Simultaneous screening for 238 drugs in blood by liquid chromatography-ionspray tandem mass spectrometry with multiple-reaction monitoring. J. Chromatograph. B. 2003;795:41-53.

Gonzales et al., Minimizing the immunogenicity of antibodies for clinical application. Tumour Biol. 2005;26(1):31-43. doi:10.1159/000084184.

Gottesman et al., Biochemistry of multidrug resistance mediated by the multidrug transporter. Annu Rev Biochem. 1993;62:385-427. doi:10.1146/annurev.bi.62.070193.002125.

Goure et al., Targeting the proper amyloid-beta neuronal toxins: a path forward for Alzheimer's disease immuno therapeutics. Alzheimers Res Ther. 2014;6(4):42. Published Jul. 9, 2014. doi:10.1186/alzrt272.

Gupta et al., Impaired Aβ clearance: a potential link between atherosclerosis and Alzheimer's disease. Front Aging Neurosci. 2015;7:115. Published Jun. 16, 2015. doi:10.3389/fnagi.2015.00115.

Hamers-Casterman et al., Naturally occurring antibodies devoid of light chains. Nature. 1993;363(6428):446-448. doi:10.1038/363446a0.

Haqqani et al., Multiplexed evaluation of serum and CSF pharmacokinetics of brain-targeting single-domain antibodies using a NanoLC-SRM-ILIS method. Mol Pharm. 2013;10(5):1542-1556. doi:10.1021/mp3004995.

Hardy et al., Alzheimer's disease: the amyloid cascade hypothesis. Science. 1992;256(5054):184-185. doi: 10.1126/science.1566067.

Hardy et al., Pathways to Alzheimer's disease. J Intern Med. 2014;275(3):296-303. doi:10.1111/joim.12192.

Hardy et al., The amyloid hypothesis of Alzheimer's disease: progress and problems on the road to therapeutics [published correction appears in Science Sep. 27, 2002;297(5590):2209]. Science. 2002;297(5580):353-356. doi:10.1126/science.1072994.

(56) References Cited

OTHER PUBLICATIONS

Huang et al., A new approach for multiple sampling of cisternal cerebrospinal fluid in rodents with minimal trauma and inflammation. J. Neurosci. Methods. Dec. 1995;63(1-2):13-22. doi:10.1016/0165-0270(95)00080-1.

Hussack et al., Engineered single-domain antibodies with high protease resistance and thermal stability. PLoS One. 2011;6(11):e28218. doi:10.1371/journal.pone.0028218.

Hussack et al., Neutralization of Clostridium difficile toxin A with single-domain antibodies targeting the cell receptor binding domain. J Biol Chem. 2011;286(11):8961-8976. doi:10.1074/jbc.M110.198754.

Iqbal et al., Kinetic analysis of novel mono- and multivalent VHH-fragments and their application for molecular imaging of brain tumours. Br J Pharmacol. 2010;160(4):1016-1028. doi:10.1111/j.1476-5381.2010.00742.x.

Jespers et al., Aggregation-resistant domain antibodies selected on phage by heat denaturation. Nat Biotechnol. 2004;22(9):1161-1165. doi:10.1038/nbt1000.

Ji et al., Drug Development for Alzheimer's Disease: Recent Progress. Exp Neurobiol. Dec. 2010; 19(3): 120-131. EPub Dec. 31, 2010. doi: 10.5607/en.2010.19.3.120.

Jones et al., Replacing the complementarity-determining regions in a human antibody with those from a mouse. Nature. 1986;321(6069):522-525. doi:10.1038/321522a0.

Kabat et al., Identical V region amino acid sequences and segments of sequences in antibodies of different specificities. Relative contributions of VH and VL genes, minigenes, and complementarity-determining regions to binding of antibody-combining sites. J Immunol. 1991;147(5):1709-1719.

Kim et al., Disulfide linkage engineering for improving biophysical properties of human V(H) domains. Protein Eng Des Sel. 2012;25(10):581-589. Epub Aug. 30, 2012. doi:10.1093/protein/gzs055.

Kornhuber et al., A method for repeated CSF sampling in the freely moving rat. J. Neurosci. Mehods. Jul. 1986;17(1):63-68. doi: 10.1016/0165-0270(86)90035-X.

Lannfelt et al., Amyloid-β-directed immunotherapy for Alzheimer's disease [published correction appears in J Intern Med. May 2014;275(5):546]. J Intern Med. 2014;275(3):284-295. doi:10.1111/joim.12168.

Li et al., Pentabody-mediated antigen delivery induces antigen-specific mucosal immune response. Mol Immunol. May 2009;46(8-9):1718-26. doi: 10.1016/j.molimm.2009.02.007.

Mangialasche et al., Alzheimer's disease: clinical trials and drug development [published correction appears in Lancet Neurol. Jun. 2011;10(6):501]. Lancet Neurol. 2010;9(7):702-716. doi:10.1016/S1474-4422(10)70119-8.

Mawuenyega et al., Decreased clearance of CNS beta-amyloid in Alzheimer's disease. Science. 2010;330(6012):1774. doi:10.1126/science.1197623.

Monsonego et al., Immunotherapeutic approaches to Alzheimer's disease. Science. 2003;302(5646):834-838. doi:10.1126/science.1088469.

Morishima-Kawashima et al., Alzheimer's disease: beta-Amyloid protein and tau. J Neurosci Res. 2002;70(3):392-401. doi:10.1002/jnr.10355.

Morrone et al., Interaction between therapeutic interventions for Alzheimer's disease and physiological Aβ clearance mechanisms. Front Aging Neurosci. 2015;7:64. Published May 5, 2015. doi:10.3389/fnagi.2015.00064.

Muruganandam et al., Selection of phage-displayed llama single-domain antibodies that transmigrate across human blood-brain barrier endothelium. FASEB J. 2002;16(2):240-242. doi:10.1096/fj.01-0343fje.

Musiek et al., Three dimensions of the amyloid hypothesis: time, space and 'wingmen'. Nat Neurosci. 2015;18(6):800-806. doi:10.1038/nn.4018.

Nicaise et al., Affinity transfer by CDR grafting on a nonimmunoglobulin scaffold. Protein Sci. Jul. 2004; 13(7): 1882-1891. doi: 10.1110/ps.03540504.

Nuttall et al., Isolation and characterization of an IgNAR variable domain specific for the human mitochondrial translocase receptor Tom70. Eur J Biochem. 2003;270(17):3543-3554. doi:10.1046/j.1432-1033.2003.03737.x.

Padlan, A possible procedure for reducing the immunogenicity of antibody variable domains while preserving their ligand-binding properties. Mol Immunol. 1991;28(4-5):489-498. doi:10.1016/0161-5890(91)90163-e.

Pardridge et al., Drug and gene delivery to the brain: the vascular route. Neuron. 2002;36(4):555-558. doi:10.1016/s0896-6273(02)01054-1.

Pardridge et al., Transport of small molecules through the blood-brain barrier: biology and methodology. Adv Drug Del Rev. Jul. 1995;15(1-3):5-36. doi: 10.1016/0169-409X(95)00003-P.

Queen et al., A humanized antibody that binds to the interleukin 2 receptor. Proc Natl Acad Sci U S A. Dec. 1989; 86(24): 10029-10033. doi: 10.1073/pnas.86.24.10029.

Rafii et al., Advances in Alzheimer's disease drug development. BMC Med. 2015;13:62. Published Mar. 25, 2015. doi:10.1186/s12916-015-0297-4.

Riechmann et al., Reshaping human antibodies for therapy. Nature. 1988;332(6162):323-327. doi:10.1038/332323a0.

Samuels et al., Modulation of vinblastine resistance with cyclosporine: A phase I study. Clin Pharmacol Thera. Oct. 1993;54(4):421-429. doi: 10.1038/clpt.1993.169.

Savonenko et al., Alzheimer's Therapeutics: Translation of Preclinical Science to Clinical Drug Development. Neuropsychopharmacology. Jan. 2012; 37(1): 261-277. EPub Sep. 21, 2011. doi: 10.1038/npp.2011.211.

Selkoe et al., The amyloid hypothesis of Alzheimer's disease at 25 years. EMBO Mol Med. 2016;8(6):595-608. Published Jun. 1, 2016. doi:10.15252/emmm.201606210.

Selkoe, Alzheimer's disease: genes, proteins, and therapy. Physiol Rev. 2001;81(2):741-766. doi:10.1152/physrev.2001.81.2.741.

Selkoe, The molecular pathology of Alzheimer's disease. Neuron. 1991;6(4):487-498. doi:10.1016/0896-6273(91)90052-2.

Sengupta et al., The Role of Amyloid-β Oligomers in Toxicity, Propagation, and Immunotherapy. EBioMedicine. 2016;6:42-49. doi:10.1016/j.ebiom.2016.03.035.

Sevigny et al., The antibody aducanumab reduces Aβ plaques in Alzheimer's disease. Nature. 2016;537(7618):50-56. doi:10.1038/nature19323.

Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. 2001;276(9):6591-6604. doi:10.1074/jbc.M009483200.

Sloane et al., The public health impact of Alzheimer's disease, 2000-2050: potential implication of treatment advances. Annu Rev Public Health. 2002;23:213-231. doi:10.1146/annurev.publhealth.23.100901.140525.

Stanimirovic et al., Engineering and pharmacology of blood-brain barrier-permeable bispecific antibodies. Adv Pharmacol. 2014;71:301-335. doi:10.1016/bs.apha.2014.06.005.

Tempest et al., Reshaping a human monoclonal antibody to inhibit human respiratory syncytial virus infection in vivo. Biotechnology (N Y). 1991;9(3):266-271. doi:10.1038/nbt0391-266.

To et al., Isolation of monomeric human V(H)s by a phage selection. J Biol Chem. 2005;280(50):41395-41403. doi:10.1074/jbc.M509900200.

Tsurushita et al., Design of humanized antibodies: from anti-Tac to Zenapax. Methods. 2005;36(1):69-83.doi:10.1016/j.ymeth.2005.01.007.

Watanabe et al., Comparative study on reversal efficacy of SDZ PSC 833, cyclosporin A and verapamil on multidrug resistance in vitro and in vivo. Acta Oncol. 1995;34(2):235-241. doi:10.3109/02841869509093961.

Chakravarthy et al., A synthetic peptide corresponding to a region of the human pericentriolar material 1 (PCM-1) protein binds

(56) References Cited

OTHER PUBLICATIONS

β-amyloid (Aβ1-42) oligomers. J Neurochem. Aug. 2013;126(3):415-24. doi:10.1111/jnc.12208. Epub Mar. 18, 2013.
Chakravarthy et al., Brain Delivery Of An Amyloid-β Oligomer (AβO)-Targeting Peptide-Therapeutic By A Novel Blood-Brain Barrier (BBB)-Crossing Domain Antibody. Alzheimer's and Dementia. Jul. 2017;13(7 suppl):P625. doi:doi.org/10.1016/j.jalz.2017.06.703. 1 page.
Chakravarthy et al., Evidence that a synthetic amyloid-β oligomer-binding peptide (ABP) targets amyloid-β deposits in transgenic mouse brain and human Alzheimer's disease brain. Biochem Biophys Res Commun. Mar. 14, 2014;445(3):656-60. doi: 10.1016/j.bbrc.2014.02.064. Epub Feb. 22, 2014.
Pardridge, Re-engineering therapeutic antibodies for Alzheimer's disease as blood-brain barrier penetrating bi-specific antibodies. Expert Opin Biol Ther. Dec. 2016;16(12):1455-1468. Epub Sep. 7, 2016.
Sumbria et al., Disaggregation of amyloid plaque in brain of Alzheimer's disease transgenic mice with daily subcutaneous administration of a tetravalent bispecific antibody that targets the transferrin receptor and the Abeta amyloid peptide. Mol Pharm. Sep. 3, 2013;10(9):3507-13. doi: 10.1021/mp400348n. Epub Aug. 20, 2013.
"PCM1 Protein," viewed Jan. 9, 2012, 3 pages.
Camden et al., "P2Y2 nucleotide receptors enhance alpha-secretase-dependent amyloid precursor protein processing," J. Biol. Chem., vol. 280, No. 18, May 13, 2005, pp. 18696-18702.
Collins et al., "Generation and initial analysis of more than 15,000 full-length human and mouse cDNA sequences," Proc Natl Acad Sci USA, vol. 99, No. 26, 2002, pp. 16899-16903.
D'Andrea et al., "Consistent immunohistochemical detection of intracellular beta-amyloid 42 in pyramidal neurons of Alzheimer's disease entorhinal cortex," Neurosci. Lett., vol. 333, 2002, pp. 163-166.
Extended European Search Report for European Application No. 06752809, dated Jul. 21, 2008, 6 pages.
Extended European Search Report for European Notification No. 18745446, dated Mar. 19, 2021, 11 pages.
Extended European Search Report for European Application No. 18904229, dated Mar. 17, 2021, 14 pages.
Friedman et al., "The Microbial Alkaloid Toxin Staurosporine Blocks the Phorbol Ester-Induced Increase in β-Amyloid Precursor Protein in PC12 Cells," Nat. Toxins, vol. 5, 1997, pp. 173-179.
Golde, "Alzheimer disease therapy: Can the Amyloid cascade be halted?" J. Clin. Invest, vol. 111, 2003, pp. 11-18.
Guo et al., "Protein tolerance to random amino acid change," Proc Natl Acad Sci USA, vol. 101, 2004, pp. 9205-9210.
Hill et al., "Functional Analysis of conserved Histidines in ADP-Glucose Pyrophosphorylase from *Escherichia coli*," Biochem. Biophys. Res. Comm., vol. 244, 1998, pp. 573-577.
International Search Report and Written Opinion of the International Searching Authority for International Application No. PCT/CA2006/000990, dated Oct. 19, 2006.
International Search Report and Written Opinion of the International Searching Authority for International Application No. PCT/IB2018/050576, dated May 4, 2018.
International Search Report and Written Opinion of the International Searching Authority for International Application No. PCT/IB2018/055747, dated Nov. 22, 2018.
Joliot et al., "Transduction peptides: from technology to physiology," Nat. Cell Biol., vol. 6, 2004, pp. 189-196.
Lazar et al., "Transforming Growth Factor a: Mutation of Aspartic Acid 47, and Leucine 48 Results in Different Biological Activity," Mol. Cell. Biol., vol. 8, 1988, pp. 1247-1252.
Lee et al., "Amyloid beta peptide directly inhibits PKC activation," Mol. Cell Neurosci., vol. 26, No. 2, 2004, pp. 222-231.
McLean et al., "Soluble pool of Abeta amyloid as a determinant of severity of neurodegeneration in Alzheimer's disease," Ann. Neurol., vol. 46, 1999, pp. 850-866.
Van Geel et al., "Comparative analysis of an evolutionary chromosomal breakpoint indicates a recent origin for the human 4q telomere," Genbank Ascension No. AAK21980, Jul. 1, 2001, 4 pages.
Wacey et al., "Disentangling the perturbational effects of amino acid substitutions in the DNA-binding domain of p53.," Hum Genet, vol. 104, 1999, pp. 15-22.
Zhao et al., "Intracellular cargo delivery using tat peptide and derivatives," Med. Res. Rev., vol. 24, 2004, pp. 1-12.

* cited by examiner

IR-800-FC5-mFc-ABP binding of brain Aβ

Wild type  AD-Tg

A            FC5-ABP

B            FC5-Fc-ABP

FC5(H3)-hFc1X7-ABP (ABP SEQ ID NO 35)

FC5(H3)-hFc1X7-ABP (ABP SEQ ID NO 36)

*FC5(H3)-hFc-ABP crosses in vitro rat-BBB intact*

A. Ex vivo binding of FC5(H3)-hFc-ABP (ABP SEQ ID NO 36)
(in vitro target engagement)

B. In vivo binding of FC5(H3)-hFc1x7-ABP (ABP SEQ ID NO 36)

FUSION PROTEIN COMPRISING A BLOOD-BRAIN BARRIER (BBB)-CROSSING SINGLE DOMAIN ANTIBODY FC5, AN IMMUNOGLOBULIN FC FRAGMENT AND A BETA-AMYLOID BINDING POLYPEPTIDE (ABP)

RELATED APPLICATIONS

This application is a national stage filing under 35 U.S.C. § 371 of International Patent Application Serial No. PCT/IB2018/050576, filed on Jan. 30, 2018, which claims benefit under 35 U.S.C § 119(e) from U.S. Provisional Application No. 62/452,015, filed on Jan. 30, 2017, and U.S. Provisional Application No. 62/530,980, filed on Jul. 11, 2017, the entire contents of each of which are incorporated herein by reference.

The instant application contains a Sequence Listing which has been submitted in ASCII format via EFS-Web and is hereby incorporated by reference in its entirety. Said ASCII copy, created on Mar. 25, 2021 is named "A0899.70015US00-SUBSEQ-LJG.txt" and is 84,133 bytes in size.

FIELD OF THE INVENTION

The present invention relates to compounds that transmigrate the blood-brain barrier, and uses thereof. More specifically, the present invention relates to compounds that may comprise an antibody or fragment thereof that crosses the blood-brain barrier, an immunoglobulin Fc domain or fragment thereof, and a polypeptide binding to beta-amyloid, fusion proteins and compositions thereof and their use in the treatment of Alzheimer's disease.

BACKGROUND OF THE INVENTION

Neurodegenerative diseases, such as Alzheimer's and Parkinson's disease, are an increasing burden on our ageing society because there are currently no effective treatments for these disabling conditions. Alzheimer's disease (AD) is an irreversible neurodegenerative disorder affecting approximately 15% of the population over 65 years of age and is the predominant cause of progressive intellectual and cognitive failure in the ageing population (Hardy et al, 2014).

In AD, there is a severe loss of cholinergic neurons with a consequent decline in the levels of acetylcholine (ACh), a key neurotransmitter involved in memory processing and storage. In addition, excitotoxicity induced by neurotransmitter glutamate is also implicated in the pathogenesis of AD. Therefore, cholinergic augmentation and/or inhibition of glutamate toxicity might improve cognition in AD. Indeed, the only FDA approved drugs for the treatment of AD are acetylcholine esterase (AChE) inhibitors (e.g., donepezil, rivastigmine, galantamine) to prevent the loss of ACh and inhibitors of specific glutamate receptors (e.g., memantine) (Mangialasche et al, 2010; Ji and Ha, 2010; Savonenko et al, 2012). However, the beneficial effects of these symptomatic drugs are limited and transient, providing temporary improvement in cognitive functions and do not stop the progression of the disease. While other treatments including antioxidants, anti-inflammatory drugs (NSAIDS), cholesterol-lowering drugs and estrogen therapy are considered, none of these treatments appear to have any long-term beneficial effects, particularly in improving memory and cognitive function in AD patients (Magialasche et al, 2010; Ji and Ha, 2010).

A major hallmark of Alzheimer's disease is the accumulation of a 39-43 amino acid peptide β-amyloid (Aβ) in the brain in the form of aggregates and plaques. A considerable body of evidence based on genetic, pathological and biochemical studies indicate that Aβ, particularly its oligomeric aggregates, plays a central role in the development of AD pathology (Hardy et al, 2014; DeLaGarza, 2003; Selkoe and Hardy, 2016). According to amyloid hypothesis, a chronic imbalance in the production and clearance of Aβ in the brain results in its accumulation and aggregation with ageing. These Aβ aggregates are believed to initiate a cascade of events leading to synaptic loss and neuronal functions, leading to a progressive loss of memory and other cognitive functions (Hardy et al, 2014; DeLaGarza, 2003; Selkoe and Hardy, 2016; Sengupta et al, 2016).

The generation of Aβ from its precursor protein APP is achieved by the sequential proteolysis of APP by proteases β and γ secretases (Barageb and Sonawane, 2015). Inhibitors of these enzymes have been shown to reduce Aβ production and are being developed as potential drugs for treating AD (Hardy et al, 2014; Mangialasche et al, 2010; Selkoe and Hardy, 2016; Ji and Ha, 2010). Similarly, agents that sequester and/or promote Aβ clearance are also being developed. Notable among these are the development of immunotherapies with AD vaccine. Both active (Aβ peptides) and passive immunization (Aß-antibodies) have been shown to be effective in preventing amyloid deposition as well as clearing of preformed amyloid plaques in transgenic animal models of AD and in clinical trials involving AD patients (Mangialasche et al, 2010; Ji and Ha, 2010; Morrone et al, 2015; Lannfelt et al, 2014; Selkoe and Hardy, 2016; Goure et al, 2014).

Inhibitors of β and γ secretases that prevent proteolytic cleavage of amyloid precursor protein (APP) and thereby reduce or suppress brain Aβ production are being developed (e.g., tarenflurbil, semagacestat, verubecestat). However, their therapeutic efficacy in reducing Aβ burden is not yet known and many of these drugs have failed in pre-clinical or clinical trials (Savonenko et al, 2012; Musiek and Holtzman, 2015). Moreover, since these enzymes are also involved in the processing of other enzymes and signaling molecules such as Notch that are linked to neuronal development (Savonenko et al, 2012; Musiek and Holtzman, 2015), these inhibitors may have serious non-specific side effects.

Immunotherapeutic approaches such as active (Aß vaccine, AN1792) and passive immunization (e.g., Bapineuzumab, Solanezumab, Crenezumab, aducanumab etc) have been shown to be quite effective in reducing Aβ deposition and partial elimination of memory deficits in transgenic animals (Monsonego and Weiner, 2003; Bard et al, 2000, Sevigny J et al., 2016). Several clinical trials using both active and passive immunization have shown reduction in brain Aβ deposition with moderate improvement in cognition. However, clinical trials had to be abandoned due to severe inflammatory reactions (meningo-encephalitic presentation), vasogenic edema, and micro-haemorrhages in AD patients. Despite these limitations, the immunotherapy approach indicates that agents that effectively sequester Aβ, and prevent its deposition and toxicity, could potentially serve as effective drugs in arresting the progression of AD, and even prevent its development (Rafii and Aisen, 2015; Selkoe and Hardy, 2016).

Treatment as well as early diagnosis of AD and other diseases that originate in the brain remain challenging because the majority of suitable therapeutic molecules and diagnostics cannot penetrate the tight and highly restrictive blood-brain barrier (BBB) (Abbott, 2013). The BBB constitutes a physical barricade that is formed by brain endothelial cells (BECs) that line the blood vessels and connect with each other through tight junctions (Abbott, 2013). The tight junctions formed between the BECs are essential for the integrity of the BBB and prevent the paracellular transport of molecules larger than 500 daltons (Da). Because brain endothelial cells exhibit very low pinocytosis rates (Abbott, 2013), transcellular transport of larger molecules is limited to the highly specific receptor mediated transcytosis (RMT) pathway, and the passive, charge-based adsorption mediated transcytosis (Abbott, 2013; Pardridge, 2002). Additionally, the high density of efflux pumps, such as P-glycoprotein or the multi-drug resistance protein-1 (MDR-1), contribute to the removal of unwanted substances from the brain (Abbott, 2013).

While all these characteristics protect the brain from pathogens and toxins, they equally prevent the entry of most therapeutics. In fact, less than 5% of small molecule therapeutics and virtually none of the larger therapeutics can cross the BBB in pharmacologically relevant concentrations (i.e., sufficient to engage a central nervous system (CNS) target and elicit pharmacologic/therapeutic response) unless they are specifically 'ferried', that is, coupled to a transporter molecule. Due to the lack of effective 'carriers' to transport molecules across the BBB, numerous drugs against neurodegenerative diseases have been 'shelved' or eliminated from further development as they cannot be delivered to the brain in sufficient amount.

Despite considerable progress in understanding the molecular mechanism of AD pathology, there are no effective drugs or treatments currently available that can prevent the progression of or cure the disease. Furthermore, the lack of high-capacity and high-selectivity BBB carriers delays the development of new therapeutics and diagnostics for diseases originating in the brain, including brain tumors and neurodegenerative diseases.

SUMMARY OF THE INVENTION

The present invention relates to compounds or compositions that transmigrate the blood-brain barrier, and uses thereof.

The present invention provides polypeptides which binds beta-amyloid (ß-amyloid). The polypeptides (or proteins) that bind β-amyloid may selectively bind pathologically relevant ß-amyloid$_{1-42}$ (Aβ$_{1-42}$) aggregates, and may be abbreviated and referred to herein as ABP or ABP variants.

The present invention provides fusion proteins (also referred to herein as compounds, compositions or constructs) comprising a beta-amyloid (ß-amyloid) binding polypeptide (ABP or ABP variant) linked to an antibody or fragment thereof that crosses the blood-brain barrier (BBB), wherein BBB herein refers to an abbreviation for the carrier antibody or fragment that transmigrates the blood brain barrier. In a preferred embodiment, the fusion protein comprising an ABP or ABP variant and a BBB carrier, or fragment thereof, wherein the ABP and BBB components of the fusion protein may be linked via an Fc region or portion thereof. In a preferred embodiment, the fusion protein comprising an ABP or ABP variant and a BBB, further comprises an immunoglobumin protein effector domain, known as Fc, or fragment thereof, wherein the ABP and BBB components of the fusion protein may be linked via the Fc region or portion thereof. For example, a construct of the present invention may further comprise a linker (L), wherein L is a small linking peptide or peptide-like chain. For example, the BBB-Fc-L-ABP construct provided may be a single chain polypeptide or a dimeric polypeptide, wherein the single chain polypeptide comprising BBB-Fc-L-ABP may form a dimer by Fc dimerization. Fc dimerization may be mediated by interaction of a large tightly packed hydrophobic interface between two Fc CH3 domains. For example, a construct of the present invention may comprise BBB-Fc-ABP. The BBB-Fc-ABP construct provided may be a single chain polypeptide (monovalent) or a dimeric polypeptide (bivalent), wherein the single chain polypeptide comprising BBB-Fc-ABP may form a dimer through Fc which allows the dimerization of the fusion protein. A compound of the present invention may be referred to as a fusion protein, construct, fusion molecule, formulation or composition.

The compounds of the present invention may be used in the treatment of Alzheimer's disease (AD).

The polypeptide that binds β-amyloid may comprise a sequence selected from the group consisting of:

(SEQ ID NO: 27)
SGKTEYMAFPKPFESSSSIGAEKPRNKKLPEEEVESSRTPWLYEQEGEVE

KPFIKTGFSVSVEKSTSSNRKNQLDTNGRRRQFDEESLESFSSMPDPVDP

TTVTKTFKTRKASAQASLASKDKTPKSKSKKRNSTQLKSRVKNITHARRI

LQQSNRNACNEAPETGSDFSMFEA;

(SEQ ID NO: 28)
FSSMPDPVDPTTVTKTFKTRKASAQASLASKDKTPKSKSK;

(SEQ ID NO: 29)
KDKTPKSKSKKRNSTQLKSRVKNITHARRILQQSNRNACN;

(SEQ ID NO: 30)
KTFKTRKASAQASLASKDKTPKSKSKKRNSTQLKSRVKNI;

The polypeptide that binds β-amyloid may be a variant that comprises a sequence:

(SEQ ID NO: 31)
X$_1$TFX$_2$TX$_3$X$_4$ASAQASLASKDKTPKSKSKKX$_5$X$_6$STQLX$_7$SX$_8$VX$_9$NI where X$_1$ = G or A, X$_2$ = G or V, X$_3$ = G or A, X$_4$ = G or A, X$_5$ = G or V, X$_6$ = G or V, X$_7$ = G or V, X$_8$ = G or A, X$_9$ = G or A In specific non-limiting embodiments, the ABP, or its variants, may comprise a sequence selected from any one of:

(SEQ ID NO: 32)
KTFKTRKASAQASLASKDKTPKSKSKKRGSTQLKSRVKNI;

(SEQ ID NO: 33)
KTFKTRKASAQASLASKDKTPKSKSKKGGSTQLKSRVKNI;

(SEQ ID NO: 34)
KTFKTRGASAQASLASKDKTPKSKSKKRGSTQLKSRVKNI;

(SEQ ID NO: 35)
KTFKTGGASAQASLASKDKTPKSKSKKRGSTQLKSRVKNI;

(SEQ ID NO: 36)
GTFGTGGASAQASLASKDKTPKSKSKKGGSTQLKSRVKNI;

-continued

```
                                          (SEQ ID NO: 37)
KTFKTRKASAQASLASKDKTPKSKSKKGGSTVKNI;

(SEQ ID NO: 38)
KTFKTRKASAQASLASKDKTPKSKSKKRG;
``` and a sequence substantially identical to any of the above sequences.

The polypeptide that binds β-amyloid (ABP) variant may comprise a polypeptide sequence selected from the group consisting of SEQ ID NO: 32, SEQ ID NO: 33, SEQ ID NO: 34, SEQ ID NO: 35, SEQ ID NO: 36, SEQ ID NO: 37, and SEQ ID NO: 38. An ABP comprising a polypeptide sequence selected from the group consisting of SEQ ID NO: 32, SEQ ID NO: 33, SEQ ID NO: 34, SEQ ID NO: 35, SEQ ID NO: 36, SEQ ID NO: 37, and SEQ ID NO: 38 may be referred to as an ABP or ABP variant. The present invention additionally comprises an ABP variant sequence having consensus sequence SEQ ID NO: 31, and may be for example SEQ ID NO: 35, or SEQ ID NO: 36, or any equivalently stable polypeptide sequence. An equivalently stable polypeptide sequence exhibits peptide stability during expression and production of fusion protein in mammalian expression system. For example, an ABP variant of the present invention may exhibit improved peptide stability over ABP peptides of the prior art (Ref. WO2006/133566).

The present invention provides an isolated polypeptide that binds β-amyloid, the isolated polypeptide that binds β-amyloid may comprise a sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, and SEQ ID NO: 38, or a sequence comprising an equivalently stable polypeptide sequence.

The present invention provides a fusion protein comprising an ABP or ABP variant selected from the group consisting of SEQ ID NO: 31, SEQ ID NO: 27, SEQ ID NO: 28, SEQ ID NO: 29, SEQ ID NO: 30, SEQ ID NO: 32, SEQ ID NO: 33, SEQ ID NO: 34, SEQ ID NO: 35, SEQ ID NO: 36, SEQ ID NO: 37, and SEQ ID NO: 38. In a non-limiting example, the ABP variant may comprise the sequence KTFKTGGASAQASLASKDKTPKSKSKKRG-STQLKSRVKNI (SEQ ID NO:35); GTFGTG-GASAQASLASKDKTPKSKSKKGGSTQLKSRVKNI (SEQ ID NO:36).

A fusion protein of the present invention may comprise an antibody, or fragment thereof, that transmigrates across the blood brain barrier (BBB) (as noted above, BBB is an abbreviation of the antibody carrier that transmigrates the blood brain barrier). The antibody, or fragment thereof, (BBB) may bind surface receptor epitopes on brain endothelial cell that allow for transmigration across the blood brain barrier. For example, such surface receptor epitopes may be TMEM30A or an Insulin-Like Growth Factor 1 Receptor (IGF1R) epitope, or isoforms, variants, portions, or fragments thereof.

The antibody, or fragment thereof, may comprise a sequence selected from the group consisting of:
  an antibody or fragment thereof comprising a complementarity determining region (CDR) 1 sequence of GFKITHYTMG (SEQ ID NO:1), a CDR2 sequence of RITWGGDNTFYSNSVKG (SEQ ID NO:2), a CDR3 sequence of GSTSTATPLRVDY (SEQ ID NO:3);
  an antibody or fragment thereof comprising CDR1 sequence of EYPSNFYA (SEQ ID NO:4), a CDR2 sequence of VSRDGLTT (SEQ ID NO:5), a CDR3 sequence of AIVITGVWNKVDVNSRSYHY (SEQ ID NO:6);
  an antibody or fragment thereof comprising CDR1 sequence of GGTVSPTA (SEQ ID NO:7), a CDR2 sequence of ITWSRGTT (SEQ ID NO:8), a CDR3 sequence of AASTFLRILPEESAYTY (SEQ ID NO:9); and
  an antibody or fragment thereof comprising CDR1 sequence of GRTIDNYA (SEQ ID NO:10), a CDR2 sequence of IDWGDGGX; where X is A or T (SEQ ID NO:11), a CDR3 sequence of AMARQSRVNLD-VARYDY (SEQ ID NO:12).

The antibody or fragment thereof may comprise a sequence selected from the group consisting of:

```
                                          (SEQ ID NO: 13)
X1VQLVX2SGGGLVQPGGSLRLSCAASGFKITHYTMGWX3RQAPGKX4X5

EX6VSRITWGGDNTFYSNSVKGRFTISRDNSKNTX7YLQMNSLRAEDTA

VYYCAAGSTSTATPLRVDYWGQGTLVTVSS, where X1 = D or E,

X2 = A or E, X3 = F or V, X4 = E or G,

X5 = R or L, X6 = F or W, X7 = L or V;

(SEQ ID NO: 18)
X1VX2LX3ESGGGLVQX4GGSLRLSCX5ASEYPSNFYAMSWX6RQAPGKX7

X8EX9VX10GVSRDGLTTLYADSVKGRFTX11SRDNX12KNTX13X14LQMNS

X15X16AEDTAVYYCAIVITGVWNKVDVNSRSYHYWGQGTX17VTVSS, where X1 is E or Q; X2 is K or Q; X3 is V or E;
X4 is A or P; X5 is V or A; X6 is F or V; X7 is
E or G; X8 is R or L; X9 is F or W; X10 is A or S;
X11 is M or I; X12 is A or S; X13 is V or L; X14 is
D or Y; X15 is V or L; X16 is K or R; and
X17 is Q or L;

(SEQ ID NO: 21)
X1VX2LX3ESGGGLVQX4GGSLRLSCX5X6SGGTVSPTAMGWX7RQAPGK

X8X9EX10VX11HITWSRGTTRX12ASSVKX13RFTISRDX14X15KNTX16Y

LQMNSLX17X18EDTAVYYCAASTFLRILPEESAYTYWGQGTX19VTVSS, where X1 is E or Q; X2 is K or Q; X3 is V or E;

X4 is A or P; X5 is A or E; X6 i sV or A; X7 is

V or F; X8 is G or E; X9 is L or R; X10 is F or W;

X11 is G or S; X12 is V or Y; X13 is D or G; X14 is

N or S; X15 is A or S; X16 is L or V; X17 is K or

R; X18 is A or S; and X19 is L or Q;

and (SEQ ID NO: 24)
X1VX2LX3ESGGGLVQX4GGSLRLSCAASGRTIDNYAMAWX5RQAPGKX6

X7EX8VX9TIDWGDGGX10RYANSVKGRFTISRDNX11KX12TX13YLQMN

X14LX15X16EDTAVYX17CAMARQSRVNLDVARYDYWGQGTX18VTVSS, where X1 is E or Q; X2 is K or Q;

X3 is V or E; X4 is A or P; X5 is V or S; X6 is D or G; X7 is L or R; X8 is F or W; X9 is A or S;

X10 is A or T; X11 is A or S; X12 is G or N; X13
```

-continued
is M or L; X₁₄ is N or R; X₁₅ is E or R; X₁₆ is P or A; X₁₇ is S or Y; and X₁₈ is Q or L.

In specific non-limiting embodiments, the antibody, or fragment thereof, may comprise a sequence selected from any one of:

(SEQ ID NO: 14)
DVQLQASGGGLVQAGGSLRLSCAASGFKITHYTMGWFRQAPGKEREFVSR

ITWGGDNTFYSNSVKGRFTISRDNAKNTVYLQMNSLKPEDTADYYCAAGS

TSTATPLRVDYWGKGTQVTVSS;

(SEQ ID NO: 15)
EVQLVESGGGLVQPGGSLRLSCAASGFKITHYTMGWVRQAPGKGLEWVSR

ITWGGDNTFYSNSVKGRFTISRDNSKNTLYLQMNSLRAEDTAVYYCAAGS

TSTATPLRVDYWGQGTLVTVSS (SEQ ID NO: 16)
EVQLVESGGGLVQPGGSLRLSCAASGFKITHYTMGWVRQAPGKGLEWVSR

ITWGGDNTFYSNSVKGRFTISRDNSKNTVYLQMNSLRAEDTAVYYCAAGS

TSTATPLRVDYWGQGTLVTVSS;

(SEQ ID NO: 17)
EVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSS;

(SEQ ID NO: 19)
QVKLEESGGGLVQAGGSLRLSCVASEYPSNFYAMSWFRQAPGKEREFVAG

VSRDGLTTLYADSVKGRFTMSRDNAKNTVDLQMNSVKAEDTAVYYCAIVI

TGVWNKVDVNSRSYHYWGQGTQVTVSS;

(SEQ ID NO: 20)
EVQLVESGGGLVQPGGSLRLSCAASEYPSNFYAMSWFRQAPGKEREFVSG

VSRDGLTTLYADSVKGRFTISRDNSKNTLYLQMNSLRAEDTAVYYCAIVI

TGVWNKVDVNSRSYHYWGQGTLVTVSS;

(SEQ ID NO: 22)
QVKLEESGGGLVQAGGSLRLSCEVSGGTVSPTAMGWFRQAPGKEREFVGH

ITWSRGTTRVASSVKDRFTISRDSAKNTVYLQMNSLKSEDTAVYYCAAST

FLRILPEESAYTYWGQGTQVTVSS;

(SEQ ID NO: 23)
QVQLVESGGGLVQPGGSLRLSCAVSGGTVSPTAMGWFRQAPGKGLEFVGH

ITWSRGTTRYASSVKGRFTISRDNSKNTVYLQMNSLRAEDTAVYYCAAST

FLRILPEESAYTYWGQGTLVTVSS;

(SEQ ID NO: 25)
QVKLEESGGGLVQAGGSLRLSCAASGRTIDNYAMAWSRQAPGKDREFVAT

IDWGDGGARYANSVKGRFTISRDNAKGTMYLQMNNLEPEDTAVYSCAMAR

QSRVNLDVARYDYWGQGTQVTVSS;

(SEQ ID NO: 26)
QVQLVESGGGLVQPGGSLRLSCAASGRTIDNYAMAWVRQAPGKGLEWVAT

IDWGDGGTRYANSVKGRFTISRDNSKNTMYLQMNSLRAEDTAVYYCAMAR

QSRVNLDVARYDYWGQGTLVTVSS;

and a sequence substantially identical to any of the above sequences.

The BBB may be an antibody, or fragment thereof, in a preferred embodiment, the BBB may be a single-domain antibody (sdAb). The sdAb may be humanized.

In a preferred embodiment, the antibody or fragment thereof (BBB) may be linked to an Fc, or fragment thereof, wherein the BBB-Fc construct may form a dimer. The invention further provides a fusion peptide comprising BBB-Fc-L-ABP, wherein the BBB-Fc portion of the fusion peptide is linked to the ABP via a short peptidic linker (for example a linker having less than 12 amino acids) and the Fc or Fc fragment allows for the dimerization of said fusion peptides to provide dimers, which accordingly protects the construct from degradation and increases its serum half-life. The Fc fragment may be any suitable Fc fragment, selected in order to impart desirable pharmacokinetics, in which the Fc or Fc fragment contributes to the long half-life of the fusion molecule. Other preferred Fc or Fc fragment embodiments may modulate, modify or suppress an immunological effector function (Shields et al., 2001). Other highly preferred Fc fragment embodiments may mediate clearance of the fusion peptide from the brain (Caram-Salas N, 2011). In a non-limiting example Fc or Fc fragments may be Fc mouse Fc2a, or a human Fc1, selected from any one of SEQ ID NO:39, SEQ ID NO:40, SEQ ID NO:41, and a sequence substantially identical thereto with attenuated effector function, which, when included in said fusion peptide, may have enhanced clearance of amyloid from the brain.

In a compound of the present invention, the BBB may be linked to the ABP via an Fc fragment, and/or any additional suitable linker L.

A compound of the present invention comprises a fusion protein; wherein the fusion protein comprises an antibody or fragment thereof, an Fc fragment, and the polypeptide that binds β-amyloid. The fusion protein may comprise an antibody or fragment thereof linked to the N-terminus of Fc fragment, and the polypeptide that binds β-amyloid is linked to the C-terminus of the Fc fragment via L, a linking peptide or a chemical linker. The antibody or fragment thereof may be linked to the C-terminus of Fc fragment and the polypeptide that binds β-amyloid linked to the N-terminus of the Fc fragment.

Accordingly, the present invention provides fusion proteins comprising an antibody or fragment thereof selected from the group consisting of SEQ ID NO:13 to SEQ ID NO:26; a polypeptide that binds b-amyloid selected from the group consisting of SEQ ID NO: 27 to SEQ ID NO:38; and an Fc fragment selected from the group consisting of SEQ ID No: 39 to SEQ ID NO:41. The provided Fc may comprise an Fc with attenuated effector functions.

For example, the fusion protein may comprise SEQ ID NOs: 42 to SEQ ID NO:52, or a sequence substantially identical thereto. The fusion protein may be a single chain polypeptide, and the single chain polypeptide of the fusion protein may for a dimeric polypeptide. It is noted that the (GGGSGGGGS (SEQ ID NO: 55) or GGGGSGGGGS (SEQ ID NO: 56)) linker provided in the fusion protein comprised in SEQ ID NO: 42 to SEQ ID NO: 52 may be any suitable linker sequence. For example, the linker sequence highlighted (ex. GGGSGGGGS (SEQ ID NO: 55)) may be any equivalent peptide linking sequence that allows for the linking of the components of the fusion protein provided, as exemplified in SEQ ID NO: 53, wherein the linker may be any peptide or chemical linker.

In an embodiment, the BBB may be linked to an Fc fragment, thus forming a dimer. The Fc fragment may be any suitable Fc fragment, for example mouse Fc2a or human Fc1, with attenuated effector function (Shields et al., 2001).

An ABP variant of the present invention may comprise SEQ ID NO: 31, for example, may be a sequence selected from any one of SEQ ID NO: 32 to 38. An ABP variant as provided herein exhibits unexpected and significant advantages over ABP polypeptides of the prior art. More specifically, the present ABP variants exhibit increased stability and bio-manufacturability. Moreover, a compound or composition of the present invention comprising an ABP or variant, as provided herein, when coupled to BBB, via a linker and/or Fc fragment as provided herein, exhibits a synergistic and unexpected efficacy in transmigrating the blood brain barrier. Such an ABP variant, when coupled to BBB, via a selected Fc fragment as provided herein, provides an unexpected, rapid and improved clearance of Aβ from the brain. Moreover, a fusion protein of the present invention comprising an ABP or ABP variant as provided herein exhibits a synergistic and unexpected efficacy in transmigrating the BBB and improved clearance of Aβ from the brain.

Accordingly, there is provided a therapeutic composition comprising a blood brain barrier transmigrating antibody or fragment thereof (BBB), an Fc (Fc), linked to a polypeptide that binds β-amyloid (ABP or ABP variant), wherein said polypeptide confers a synergistic increase in stability and efficacy of the therapeutic composition provided. As shown, unexpectedly and most significantly, a single bolus of BBB-Fc-ABP reduced brain Aβ burden by 50% within 24 hrs of treatment (FIG. 9B) compared to three months of multiple treatments with free ABP to achieve similar results in animals, (mouse model of AD) (FIG. 9A). Thus, the compound as provided herein was shown to be far more potent than free ABP in reducing brain Aβ burden. Additionally, this fusion protein comprising Fc provided a substantially longer serum half-life compared to free ABP or BBB-ABP (WO 2006/133566), thereby providing an improved therapeutic compound. (FIG. 10).

The ABP variants of the present invention, and fusion proteins (constructs) comprising ABP overcome the disadvantages of the prior art. In the prior art, the linking of ABP with a BBB carrier (WO 2006/133566) alone does not assure the generation of an effective molecule. Fusions comprising an Fc aimed at enhancing serum half-life do not ensure efficient transport of ABP across the blood brain barrier. Specific engineering and formulation of a fusion molecule comprising a BBB carrier-, Fc fragment- and ABP provide an efficient BBB-permeable therapeutic compound. The efficient blood brain barrier-permeable therapeutic compound provided comprises a specifically engineered formulation of a BBB-Fc-ABP, wherein the formulation exhibits a synergistic improvement in compound stability and efficacy. An unexpected increase in the stability of the fusion compositions, and a synergistic increase in efficacy of transmigrating the blood brain barrier and faster clearance (within 24 hrs) of Aβ from the brain, as shown in FIG. 9, is provided in a composition comprising said fusion protein constructs.

The compound provided herein may be referred to as a compound, a fusion protein, formulation, composition or construct. The provided construct may comprise an antibody or fragment thereof (which may be abbreviated BBB), an Fc fragment (abbreviated Fc), and a polypeptide that binds β-amyloid (abbreviated ABP). The construct or composition provided (which may be abbreviated herein as BBB-Fc-ABP or BBB-Fc-L-ABP), comprises components that synergistically overcome the deficiencies encountered in the prior art with respect to blood brain barrier transmigration, efficacy and compound stability. Accordingly, compounds provided herein comprise a novel formulation having superior and unexpected efficacy in transmigrating the blood brain barrier, therapeutic efficacy and compound stability.

There are instances in the prior art where Fc fusions may increase serum half-life, although serum half-life is not necessarily increased in Fc fusions. Moreover, Fc fusions do not necessarily improve transmigration across the blood brain barrier.

The present invention provides a polypeptide that binds β-amyloid, the polypeptide sequence may be selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, and SEQ ID NO: 38 and a sequence substantially identical in peptide stability.

The present invention provides a polypeptide that binds β-amyloid, wherein when the polypeptide sequence is referred to as an ABP or an ABP variant, ABP variant sequence may comprise SEQ ID NO: 31, and may be selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, and sequence substantially identical in peptide stability, for example, any sequence variant of SEQ ID NO:31. An ABP variant having SEQ ID NO: 31 of the present invention overcomes the disadvantages of the prior art with respect to polypeptide stability. Moreover, a compound comprising an ABP of the present invention exhibits improved compound stability and bio-manufacturability. Furthermore, a compound comprising an ABP or ABP variant as provided herein exhibits a synergistic and unexpected therapeutic improvement.

An ABP variant of the present invention may comprise a sequence selected from any one of SEQ ID NO: 31 to SEQ ID NO: 38, and an equivalently stable polypeptide sequence. An ABP variant of the present invention is superior over ABP sequences of the prior art, wherein the present ABP variant polypeptides exhibit improved stability (as shown in comparison between FIG. 2A and FIG. 16).

The present invention also provides fusion proteins (also referred to as compounds, constructs, or fusion molecules) comprising an ABP, or ABP variant, of the present invention. The fusion protein may comprise an Fc fragment. The fusion protein may comprise an antibody or fragment thereof that transmigrates the blood brain barrier, an Fc fragment, and a β-amyloid binding polypeptide sequence that may be selected from the group consisting of SEQ ID NO: 31, SEQ ID NO: 32-38. The provided BBB-Fc-ABP formulations exhibit synergistic improvement in compound stability and therapeutic efficacy in removing toxic amyloid from the brain.

The fusion protein or construct, which may be referred to herein as BBB-Fc-ABP, may vary in orientations with respect to the components comprised therein. In a compound of the present invention the fusion protein forms a dimer (as shown in FIG. 1) wherein the fusion peptide dimerizes via the Fc region. For example, in an embodiment, the provided compound may comprise a fusion protein comprising a BBB linked to the N-terminus of the Fc fragment (Fc) and an ABP or ABP variant (ABP) linked to the C-terminus of the Fc fragment via a short peptidic linker attached to the C-terminus (FIG. 1A, wherein the compound is shown as a dimer of the fusion protein). In a further embodiment, the provided compound may comprise a BBB linked to the C-terminus of the Fc fragment (Fc) wherein the ABP or ABP variant (ABP) may be linked to the N-terminus of the Fc fragment via a suitable linker (L) (FIG. 1B). It is noted that in configuration 1A, the ABP or ABP variant may be N-terminally (fusion) or C-terminally (chemical linking) fused/linked to Fc. In other possible configurations, the BBB may be linked to the N-terminus of the ABP, and the ABP linked to the N-terminus of the Fc fragment (FIG. 1C). In yet another possible configuration the BBB may be linked to the C-terminus of the ABP, and the ABP is linked to the C-terminus of the Fc fragment (FIG. 1D).

The compounds provided herein comprise fusion proteins comprising a sequence selected from any one of SEQ ID NO:42 SEQ ID NO:43, SEQ ID NO:44, SEQ ID NO: 45, SEQ ID NO:46, SEQ ID NO: 47, SEQ ID NO: 48, SEQ ID NO:49, SEQ ID NO:50, SEQ ID NO:51, SEQ ID NO:52, SEQ ID NO: 53 and a sequence substantially identical to any of these sequences. The fusion protein of the present is a fusion protein (BBB-Fc-ABP or BBB-Fc-L-ABP, wherein L may be any suitable linker) dimer (as shown in FIG. 1, and preferably, FIG. 1A or 1B)". In a non-limiting example, the compound or fusion protein provided may comprise a polypeptide comprising sequence SEQ ID NO:35 (ABP-GG-G) or SEQ ID NO:36 (ABP-6G); an antibody or fragment thereof comprising sequence SEQ ID NO:17 (FC5-H3); and an Fc fragment comprising sequence SEQ ID NO:40 (hFc1×7).

In a specific non-limiting embodiment of the present invention, the compound may comprise sequence SEQ ID NO:46 [FC5-H3-hFc1×7-L-ABP(GG-G)] or SEQ ID NO:47 [FC5-H3-hFc1×7-L-ABP(6G)], wherein the L may be any suitable linker.

The compounds of the present invention transmigrate the blood-brain barrier.

The present invention encompasses a nucleic acid molecule encoding any compound of the present invention as described herein. Vectors comprising the nucleic acid molecule of a fusion protein or compound of the present invention are also included in the scope of the present invention.

The present invention encompasses a composition comprising a compound or fusion protein of the present invention and a pharmaceutically-acceptable carrier, diluent, or excipient.

Kits comprising a pharmaceutical composition of the present invention are also included in the scope of the present invention.

The composition of the present invention may be used for treating Alzheimer's disease in a patient.

The composition of the present invention may be used for reducing toxic ß-amyloid (Aß) levels in the brain or CSF of a subject having increased levels of brain Aß.

The present invention provides a method of treating Alzheimer's disease, wherein a pharmaceutical composition of the present invention may be administered to a subject in need thereof.

The present invention provides a method of reducing toxic ß-amyloid (Aß) levels in the brain of a subject having increased levels of brain Aß. The method of the present invention comprises the administration of a compound of the present invention to a patient with AD. More specifically, the present method comprises the steps of repeated parenteral administration of a sufficient amount of a pharmaceutical composition of the present invention to a subject.

In the method of the present invention, parenteral administration is subcutaneous or intravenous administration.

The method of the present invention reduces toxic ß-amyloid levels, after repeated parenteral administration of a composition provided herein, in the brains of subjects having increased brain levels of Aß. More specifically, toxic ß-amyloid levels are reduced within four weeks of repeated parenteral administration of the composition of the present invention.

The method of the present invention reduces toxic ß-amyloid levels in the cerebrospinal fluid (CSF) of subjects after parenteral administration of the composition of the present invention. More specifically, toxic ß-amyloid levels in the cerebrospinal fluid (CSF) of subjects is significantly reduced within 24 hours of a single parenteral administration of the composition of the present invention; wherein significant reduction is up to 50% within 24 hours.

The present invention provides a blood brain barrier-permeable single domain antibody (sdAb), wherein the sdAb is either camelid FC5 or a humanized version thereof. FC5 displayed in bi-valent format on Fc has been shown to have improved blood brain barrier-crossing properties compared to FC5 in $V_HH$ format (Farrington et al., 2014).

The present invention provides a compound comprising a BBB that facilitates blood brain barrier transmigration in vitro and an Fc fragment and increases serum half-life of the fusion molecule, wherein serum half-life of the Fc fusion becomes similar to that of a full IgG. Prolonged serum half-life of FC5-Fc-ABP also increases overall brain exposure, which is particularly important for treating chronic diseases such as Alzheimer's Disease.

The FC5-Fc-ABP fusion molecule as well as a humanized version FC5(H3)-hFc-ABP, and IGF1R5-H2-ABP fusion molecules were produced in CHO cells. The ABP variants of the present invention, as provided in SEQ ID NO: 31, are methodically re-engineered with specific point-mutations or deletions that enhance bio-manufacturability and stability of the fusion molecule (SEQ ID NO. 45, SEQ ID NO. 46; SEQ ID NO. 47, SEQ ID NO: 48, SEQ ID NO: 49, SEQ ID NO: 50, SEQ ID NO: 51, SEQ ID NO: 52, SEQ ID NO: 53). The fusion molecules of the present invention comprising the ABP variants not only retain Aβ binding ability, the provided fusion molecules comprising the ABP variants not only penetrate the blood brain barrier, but advantageously allow for the clearance of Aβ from the brain, for example, the rapid clearance of Aβ from the brain within 24 hours of administration.

The ABP variants of the present invention, for example ABP(GG-G) (SEQ ID NO: 35) or ABP(6G) (SEQ ID NO: 36), were specifically engineered to enhance stability and manufacturability of the construct (as shown in FIG. 16). The enhanced stability and bio-manufacturability of the construct of the present invention is significant in the present art. The present invention accordingly encompasses ABP and ABP variants that enhance stability and bio-manufacturability of the fusion molecules provided, but also retain therapeutic activity (as provided in FIG. 15A).

Therefore, the fusion molecules comprising different ABP variants, as provided in SEQ ID NO:31, such as in SEQ ID NOs: 32-38 retain the Aβ oligomer binding ability of the parent ABP in vitro (FIGS. 2B,2C, 12 and 15 A, B and C) as well as the BBB-penetrating property of the parent FC5 both in vitro and in vivo (FIGS. 4, 5A, 6, 7, 17A, 17B, 18 and 19). The ABP is transported across the BBB by the carrier, for example FC5, in vitro and in vivo, as established by its presence in the rat and dog CSF (FIGS. 5 and 6). The ABP fusion was also transported and delivered to the target regions in the brain, such as hippocampus and cortex in both wild type and AD transgenic mice (FIGS. 8 and 19). The brain-delivered ABP also promoted Aβ clearance in the CSF (FIGS. 9C and 11A and 11B) and in cortical and hippocampal regions of AD transgenic mice and rat (FIGS. 9B and 11C). In addition, and most importantly, Aβ clearance in rat AD model correlated with enhanced hippocampal volume and neuronal connectivity (FIGS. 12A and 12B) indicating desired pharmacological/physiological response to treatment.

Unexpectedly and most significantly, a single bolus of BBB-Fc-ABP reduced brain Aβ burden by 50% within 24 hrs of treatment (FIG. 9B) compared to three months of multiple treatments with free ABP to achieve similar results in animals (FIG. 9A). Thus, the BBB-enabled ABP was shown to be far more potent than free ABP in reducing brain Aβ burden. Additionally, this compound has a substantially longer serum half-life compared to free- or FC5-ABP, an essential characteristic of a better therapeutic, due to its fusion with Fc (FIG. 10).

In the prior art, the linking of ABP with a BBB carrier (WO 2006/133566) alone does not ensure the generation of an effective molecule. Fusion with Fc to enhance serum half-life also does not ensure efficient transport of ABP across blood brain barrier. Suitable engineering and formulation of BBB carrier-, Fc fragment- and ABP fusion molecule, as provided in the fusion protein constructs of present invention, provide an efficient BBB-permeable therapeutic compound.

This novel bi-functional fusion molecule has distinct advantage over conventional therapeutic antibodies currently under development. First, the BBB-fused therapeutic ABP can penetrate the brain at much higher levels and at a faster rate, which substantially improves the therapeutic efficacy. In addition, ABP and BBB (ex. FC5) have relatively lower affinity towards their respective receptors and thus are likely cleared from the brain faster, and accordingly facilitate faster clearance of ABP-bound Aβ. Unlike therapeutic antibodies that mainly employ reactive microglia/astrocytes for Aβ clearance (e.g., aducanumab), which is a slower process, the fusion molecule of the present invention likely employs faster perivascular drainage pathway for Aβ clearance. This is supported by a nearly 50% reduction in CNS Aβ within 24 hr of treatment compared to free ABP (FIG. 9B) and antibody-based therapeutics, which require months of treatment with repeated multiple doses to achieve similar results.

Moreover, the present compound is less likely to elicit neuro-inflammatory response compared to antibody-based therapeutics.

BRIEF DESCRIPTION OF THE DRAWINGS

These and other features of the invention will now be described by way of example, with reference to the appended drawings, wherein:

FIG. 1 shows the corresponding dimers of the fusion protein comprising BBB-Fc-ABP. The 3 components (i.e. BBB, Fc, and ABP) are depicted in various configurations, as illustrated in FIGS. 1A, 1B, 1C, and 1D.

FIG. 2: shows the production of FC5-mFc-ABP and humanized FC5(H3)-hFc-ABP (ABP SEQ ID NO: 32) fusion molecule in CHO cells.

As shown in FIG. 5, FC5-mFc-ABP appeared in the CSF in a time- and dose-dependent manner with Cmax between 12 and 24 h, indicating transport of ABP by FC5 into brain and CSF compartments in vivo. Serum PK parameters (FIG. 5 and Table 1) show that alpha- and beta-half-life of FC5-mFc-ABP is similar to that of a full IgG (a benchmark antibody containing rat Fc).

As shown in FIG. 12 A, increased hippocampal volume was observed in ABP-treated Tg rats (Tg-ABP) compared to saline-treated Tg rats (Tg-Sal) after four weeks of treatment.

FIG. 18 (1) A and B show immunoblots probed with hFc- and ABP-specific antibodies, respectively. The molecular size is exactly identical to that of the fusion molecule that was applied to in vitro blood brain barrier model. FIG. 18(1) C shows sandwich ELISA in which the molecule after crossing the BBB was captured by FC5-specific antibody on ELISA plate and detected with ABP-specific antibody. This sandwich ELISA confirmed that FC5(H3)-hFc1×7-ABP remained intact after crossing rat blood brain barrier in vitro. Similar results were obtained with FC5(H3)-hFc1×7-ABP (ABP, SEQ ID NO: 36); FIG. 18(2) A, B, and C.

FIG. 19A shows immunoblot probed with ABP-specific antibody. The molecular size is exactly identical to that of the fusion molecule that was injected into the animals. FIG. 19 B shows sandwich ELISA of the same extract, molecule in the extract captured with FC5-specific antibody on the ELISA plate and detected with ABP-specific antibody. This confirms immunoblot results that FC5(H3)-hFc1×7-ABP is transported across the BBB in vivo and delivered to the brain intact.

FIG. 21 A shows binding of Alexa 647-labeled FC5-hFc-ABP construct to natural amyloid-ß (Aß) deposits in AD transgenic mice in vivo after intra-hippocampal injection. Identity of Aß was confirmed by probing the brain sections with Aß-specific antibody 6E10 labelled with Alexa 488 and demonstrating co-localization of two signals (Merge). FIG. 21B shows demonstration of target engagement by ELISA. Following intra-hippocampal injection (4 hrs post-injection) of FC5 (H3)-hFc-ABP construct into wild type and AD transgenic mice, hippocampal formation was dissected and homogenized. FC5-ABP fusion construct was detected by sandwich ELISA using FC5 antibody as capturing antibody and ABP antibody as the detection antibody. In vivo binding of ABP to endogenous Aß was detected by the same sandwich ELISA but with Aß-specific antibody as the detection antibody. It is clear from the FIGS. 21 A and 21B that the FC5-ABP construct remains intact 4 hrs post-injection in both wild type and AD transgenic mice. Most importantly, in Tg mice which expresses human Aß, injected ABP binds Aß and is pulled down as a complex (FC5(H3)-hFc-ABP*Aß) indicating Aß-target engagement by ABP in vivo.

As shown in FIG. 22 A, serum and CSF PK profile were very similar for non-humanized and humanized constructs. FC5-mFc2a-ABP or FC5(H3)-hFc1×7-ABP was administered intravenously into Tg mice via tail vein injection at 15 mg/kg as described for FIG. 9B. FC5-Fc-ABP and Aß levels in the CSF were measured by nanoLC-MRM as described in FIG. 9B. As shown in FIG. 22 B, the levels of non-humanized and humanized FC5-Fc-ABP in the CSF were similar, and most importantly, changes (decrease) in CSF Aß levels were also very similar, indicating that humanization of FC5-Fc-ABP construct did not affect the PK and PD profile of the fusion construct.

DETAILED DESCRIPTION OF THE INVENTION

Figure 1:
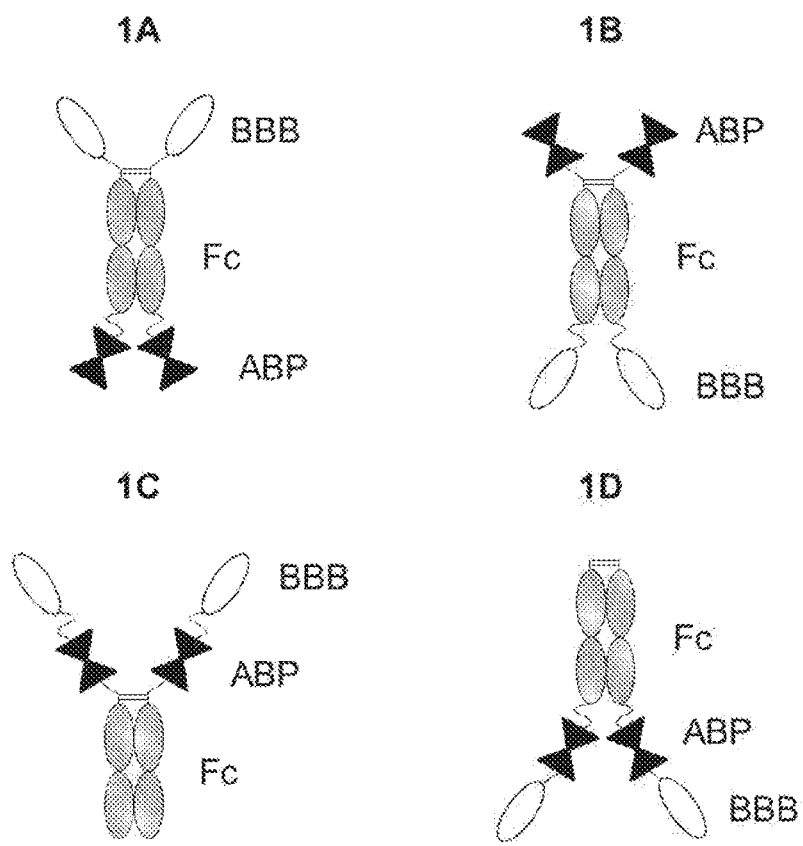
FIG. 1: shows schematic drawings of a blood brain barrier-crossing, amyloid-binding fusion protein. The fusion protein comprises a BBB-crossing single-domain antibody (BBB or BBB carrier), an Fc fragment (Fc) and an amyloid-binding peptide (ABP).

The present invention provides polypeptides, fusion proteins comprising said polypeptides, and fusion proteins comprising said polypeptides and antibodies or fragments thereof that transmigrate the blood-brain barrier.

The present invention provides polypeptides which binds beta-amyloid (ß-amyloid). The polypeptides (or proteins) that bind β-amyloid may selectively bind pathologically relevant ß-amyloid$_{1-42}$ (Aβ$_{1-42}$) aggregates, and may be abbreviated and referred to herein as ABP or ABP variants (or collectively as ABP).

The present invention provides fusion proteins comprising ABP or an ABP variant linked to an antibody or fragment thereof that crosses the blood-brain barrier. In a preferred embodiment, the fusion protein comprising ABP and a BBB additionally comprises an Fc or fragment thereof, wherein the ABP and BBB components of the fusion protein may be linked via an Fc region or portion thereof. For example, a construct of the present invention may comprise BBB-Fc-ABP or BBB-Fc-L-ABP, wherein L may be any suitable linker. The BBB-Fc-APB or BBB-Fc-L-ABP construct provided may be a single chain polypeptide or a dimeric polypeptide, wherein the single-chain polypeptide comprising BBB-Fc-ABP may form a multimer (preferably a dimer) via the component Fc region.

The present invention relates to compounds that transmigrate the blood-brain barrier, and uses thereof. More specifically, the present invention relates to compounds comprising a BBB and an ABP and their use in the treatment of Alzheimer's disease (AD).

There is a need for therapeutic formulations that can efficiently transmigrate ABP across the blood brain barrier, and provide the clearing of Aβ through the binding of ABP. In the prior art, a 40-amino acid Aβ-binding peptide (ABP) was identified that selectively binds Aβ$_{1-42}$ oligomers implicated in AD development (WO 2006/133566). This Aβ-binding peptide inhibits Aβ binding to cellular proteins and inhibits Aβ$_{1-42}$-induced cell toxicity in vitro (Chakravarthy et al, 2013).

This Aβ-binding peptide binds amyloid deposits in AD transgenic mice brain, as well as binds amyloid deposits in the brains from AD patients in vitro. More importantly when directly injected into live AD transgenic mice brain (Chakravarthy et al, 2014) ABP targets natural amyloid deposits in vivo. Thus, ABP can potentially target CNS Aβ, can assist in clearing Aβ from the brain, and reduce its toxic effect. However, systemically-administered ABP has limited ability to cross BBB and access the brain parenchyma by itself.

Accordingly, although ABP has been shown to bind Aβ deposits when directly applied, in order to bind and clear Aβ from the brain, parenterally administered ABP needs to permeate the blood brain barrier. The present invention advantageously provides an ABP fused to a BBB-permeable single-domain antibody, such as FC5 or IGF1R, via an Fc fragment to provide a bi-specific blood brain barrier-permeable therapeutic (Farrington et al, 2014). The BBB-Fc-ABP construct of the present invention may dimerize, i.e. the BBB-Fc-ABP single-chain fusion protein may form dimers of two single chain fusion proteins to yield a dimeric compound wherein each single chain of the dimer comprises a BBB, a Fc fragment and an ABP, to provide a BBB-Fc-ABP dimer. The BBB-Fc-ABP or BBB-Fc-L-ABP construct and dimers thereof, allows for the efficient transmigration of ABP across the blood brain barrier. Accordingly, the advantageous therapeutic clearing of Aβ through the binding of ABP in CSF and brain parenchyma is provided in the constructs and methods of the present invention.

In order to enable brain delivery of ABP and improve its efficacy, the 40-amino acid ABP polypeptide is presently fused to the C-terminus of an Fc fragment, whereas a BBB-permeable single-domain antibody, such as FC5 (WO 2002/057445), is fused to the N-terminus of the same Fc fragment, to create a bi-specific BBB-permeable therapeutic (Farrington et al, 2014). In a non-limiting embodiment of the present invention, the Fc fragment may be mouse (SEQ ID NO. 39) or human (SEQ ID NO: 40; SEQ ID NO: 41). In a preferred embodiment, the Fc fragment of the present invention was engineered to reduce effector functions (Shields et al., 2001). For example the Fc fragment may be hFc1x7 (SEQ ID NO:40) wherein the Fc fragment in the BBB-Fc-ABP fusion protein advantageously allows for the dimerization of the fusion protein to yield a therapeutically effective fusion molecule (BBB-Fc-ABP dimer) capable of transmigrating the blood brain barrier. In an embodiment, the BBB-Fc-ABP fusion protein may be FC5-H3-hFc1x7-ABP (6G) (SEQ ID NO: 47) and dimers thereof. The fusion protein may comprise a linker sequence L that is as embodied in SEQ ID NO: 47 or SEQ ID NO:53, or any suitable linker sequence.

The present invention provides an isolated polypeptide which binds beta-amyloid (ß-amyloid). A polypeptide of the present invention may comprise a sequence.

```
                                           (SEQ ID NO: 31)
X₁TFX₂TX₃X₄ASAQASLASKDKTPKSKSKKX₅X₆STQLX₇SX₈VX₉NI where X₁ = G or A, X₂ = G or V, X₃ = G or A, X₄ = G or A, X₅ = G or V, X₆ = G or V, X₇ = G or V, X₈ = G or A, X₉ = G or A
```

A polypeptide (ABP and ABP variant) of the present invention may be selected from the group consisting of: SEQ ID NO:27 to SEQ ID NO:38 or a sequence substantially identical thereto. In an embodiment, the polypeptide provided is an ABP variant comprising a sequence substantially equivalent to SEQ ID NO: 31. A sequence that is substantially equivalent thereto may confer equivalent stability to the fusion molecules.

The present invention provides a compound, namely a fusion protein, comprising an antibody or fragment thereof that transmigrates across the blood brain barrier (BBB) and a polypeptide that binds β-amyloid. The present invention provides fusion proteins comprising a BBB, a polypeptide that binds β-amyloid, and an Fc.

The term "antibody", also referred to in the art as "immunoglobulin" (Ig), as used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences.

For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen-binding determinants of the molecule, and thus determines the specificity of an antibody for its target antigen. The majority of sequence variability occurs in six hypervariable regions, three each per variable heavy (V$_H$) and light (V$_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the V$_H$ and V$_L$ domains. Chothia and Lesk (1987) define the "hypervariable loops" (H or L) based on the location of the structural loop regions in the V$_H$ and V$_L$ domains. These individual schemes define CDR and hypervariable loop regions that are adjacent or overlapping, those of skill in the antibody art often utilize the terms "CDR" and "hypervariable loop" interchangeably, and they may be so used herein. The CDR/loops are identified herein according to the Kabat scheme.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of V$_L$ and V$_H$ connected with a peptide linker), Fab, F(ab')$_2$, single-domain antibody (sdAb; a fragment composed of a single V$_L$ or V$_H$), and multivalent presentations of any of these. Antibody fragments such as those just described may require linker sequences, disulfide bonds, or other type of covalent bond to link different portions of the fragments; those of skill in the art will be familiar with the requirements of the different types of fragments and various approaches and various approaches for their construction.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed V$_H$H. sdAb have also been observed in shark and are termed V$_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from V$_H$, V$_H$H, V$_L$, or V$_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, camelization, or other methods of antibody engineering. Also encompassed by the present invention are homologues, derivatives, or fragments that retain the antigen-binding function and specificity of the sdAb.

SdAb possess desirable properties for antibody molecules, such as high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996). Further modifications to increase stability, such as the introduction of non-canonical disulfide bonds (Hussack et al, 2011a,b; Kim et al, 2012), may also be brought to the sdAb.

A person of skill in the art would be well-acquainted with the structure of a single-domain antibody (see, for example, 3DWT, 2P42 in Protein Data Bank). An sdAb comprises a single immunoglobulin domain that retains the immunoglobulin fold; most notably, only three CDR/hypervariable loops form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3.

The antibody or fragment thereof as described herein may transmigrate the blood-brain barrier. The brain is separated from the rest of the body by a specialized endothelial tissue known as the blood-brain barrier (BBB). The endothelial cells of the BBB are connected by tight junctions and efficiently prevent many therapeutic compounds from entering the brain. In addition to low rates of vesicular transport, one specific feature of the BBB is the existence of enzymatic barrier(s) and high level(s) of expression of ATP-dependent transporters on the abluminal (brain) side of the BBB, including P-glycoprotein (Gottesman and Pastani, 1993; Watanabe, 1995), which actively transport various molecules from the brain into the blood stream (Samuels, 1993). Only small (<500 Daltons) and hydrophobic (Pardridge, 1995) molecules can more readily cross the BBB. Thus, the ability of the antibody or fragment thereof as described above to specifically bind the surface receptor, internalize into brain endothelial cells, and undergo transcytosis across the blood brain barrier by evading lysosomal degradation is useful in the neurological field. The antibody or fragment thereof that crosses the blood-brain barrier may be used to carry other molecules, such as therapeutics, for delivery to the brain tissue. The antibody or fragment thereof may be any suitable antibody or fragment thereof known in the art to transmigrate the blood brain barrier.

The present invention provides a compound, or fusion protein, comprising an antibody or fragment thereof that transmigrates the blood brain barrier (BBB). An antibody or fragment of the present invention may bind to, for example, transmembrane protein 30A (TMEM30A), as described in WO 2007/036021, or to an Insulin-Like Growth Factor 1 Receptor (IGF1R) epitope, or isoforms, variants, portions, or fragments thereof.

The antibody or fragment thereof in the compound of the present invention may comprise a complementarity determining region (CDR) 1 sequence of HYTMG (SEQ ID NO:1); a CDR2 sequence of RITWGGDNTFYSNSVKG (SEQ ID NO:2); and a CDR3 sequence of GSTSTATPLRVDY (SEQ ID NO:3); or a CDR1 sequence of EYPSNFYA (SEQ ID NO:4), a CDR2 sequence of VSRDGLTT (SEQ ID NO:5), a CDR3 sequence of AIVITGVWNKVDVNSRSYHY (SEQ ID NO:6); or a CDR1 sequence of GGTVSPTA (SEQ ID NO:7), a CDR2 sequence of ITWSRGTT (SEQ ID NO:8), a CDR3 sequence of AASTFLRILPEESAYTY (SEQ ID NO:9); or a CDR1 sequence of GRTIDNYA (SEQ ID NO:10), a CDR2 sequence of IDWGDGGX;

where X is A or T (SEQ ID NO:11), a CDR3 sequence of AMARQSRVNLDVARYDY (SEQ ID NO:12).

As previously stated, the antibody or fragment thereof may be an sdAb of camelid origin or derived from a camelid V$_H$H, and thus may be based on camelid framework regions;

alternatively, the CDR described above may be grafted onto $V_{NAR}$, $V_HH$, $V_H$ or $V_L$ framework regions. In yet another alternative, the hypervariable loops described above may be grafted onto the framework regions of other types of antibody fragments (Fv, scFv, Fab) of any source (for example, mouse or human) or proteins of similar size and nature onto which CDR can be grafted (for example, see Nicaise et al, 2004).

The present invention further encompasses an antibody or fragment thereof that is chimeric (or chimerized), veneered, or humanized. Chimeric antibodies or fragments thereof are constructs in which the native variable domain (of mouse or camelid origin) is linked to human constant domain(s) (see Gonzales et al 2005). Veneering or re-surfacing of antibodies involves replacing exposed residues in the framework region of the native antibody or fragment thereof with the amino acid residues in their human counterpart (Padlan, 1991; Gonzales et al 2005). Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In this process, one or more than one of the CDR defined herein may be fused or grafted to a human variable region ($V_H$, or $V_L$), to other human antibody (IgA, IgD, IgE, IgG, and IgM), to human antibody fragment framework regions (Fv, scFv, Fab), or to human proteins of similar size and nature onto which CDR can be grafted (Nicaise et al, 2004). In such a case, the conformation of said one or more than one hypervariable loop is likely preserved, and the affinity and specificity of the sdAb for its target (i.e., an epitope on brain endothelial cells, such as TMEM30A, or an IGF1R epitope) brain endothelial cells) is likely minimally affected. As is known by those of skill in the art, it may be necessary to incorporate certain native amino acid residues into the human framework in order to retain binding and specificity. Humanization by CDR grafting is known in the art (for example, see Tsurushita et al, 2005; Jones et al, 1986; Tempest et al, 1991; Riechmann et al, 1988; Queen et al, 1989; reviewed in Gonzales et al, 2005—see also references cited therein), and thus persons of skill would be amply familiar with methods of preparing such humanized antibody or fragments thereof.

The provided antibody or fragment thereof may be a humanized version of the FC5 antibody (described in WO 2002/057445) or an IGF1R antibody. FC5 (comprising a sequence of any one of SEQ ID NO: 13, SEQ ID NO: 14, SEQ ID NO: 15, SEQ ID NO: 16, SEQ ID NO: 17), and IGF1R (comprising a sequence of any one of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26) bind to the surface of receptor epitopes on brain endothelial cells and subsequently transmigrates the blood-brain barrier (BBB). FC5 has also been shown to act as a carrier to usher molecules of various sizes across the BBB (see for example, WO 2011/127580). The antigen mediating FC5 transmigration was tentatively identified as transmembrane domain protein 30A (TMEM30A; WO 2007/036021), which is enriched on the surface of brain endothelial cells.

For example, and without wishing to be limiting, the antibody or fragment thereof may comprise the sequence:

(SEQ ID NO: 13)
$X_1$VQLVX$_2$SGGGLVQPGGSLRLSCAASGFKITHYTMGWX$_3$RQAPGKX$_4$X$_6$

EX$_6$VSRITWGGDNTFYSNSVKGRFTISRDNSKNTX$_7$YLQMNSLRAEDTAV

YYCAAGSTSTATPLRVDYWGQGTLVTVSS, where $X_1$ = D or E, $X_2$ = A or E, $X_3$ = F or V, $X_4$ = E or G, $X_6$ = R or L, $X_6$ = F or W, $X_7$ = L or V, or a sequence substantially identical thereto;

(SEQ ID NO: 18)
$X_1$ VX$_2$LX$_3$ESGGGLVQX$_4$GGSLRLSCX$_5$ASEYPSNFYAMSWX$_6$RQAPGK

X$_7$X$_8$EX$_9$VX$_{10}$GVSRDGLTTLYADSVKGRFTX$_{11}$SRDNX$_{12}$KNTX$_{13}$X$_{14}$

LQMNSX$_{15}$X$_{16}$AEDTAVYYCAIVITGVWNKVDVNSRSYHYWGQGTX$_{17}$VT

VSS,, where $X_1$ is E or Q; $X_2$ is K or Q; $X_3$ is V or

E; $X_4$ is A or P; $X_5$ is V or A; $X_6$ is F or V; $X_7$ is

E or G; $X_8$ is R or L; $X_9$ is F or W; $X_{10}$ is A or S;

$X_{11}$ is M or I; $X_{12}$ is A or S; $X_{13}$ is V or L; $X_{14}$ is D or Y; $X_{15}$ is V or L; $X_{16}$ is K or R; and $X_{17}$ is Q or L; or a sequence substantially identical thereto;

(SEQ ID NO: 21)
$X_1$VX$_2$LX$_3$ESGGGLVQX$_4$GGSLRLSCX$_5$X$_6$SGGTVSPTAMGWX$_7$RQAPGK

X$_8$X$_9$EX$_{10}$VX$_{11}$HITWSRGTTRX$_{12}$ASSVKX$_{13}$RFTISRDX$_{14}$X$_{15}$KNT

X$_{16}$YLQMNSLX$_{17}$X$_{18}$EDTAVYYCAASTFLRILPEESAYTYWGQGT X$_{19}$

VTVSS,, where $X_1$ is E or Q; $X_2$ is K or Q; $X_3$ is V or E; $X_4$ is A or P; $X_5$ is A or E; $X_6$ is V or A; $X_7$ is V or F; $X_8$ is G or E; $X_9$ is L or R; $X_{10}$ is F or W; $X_{11}$ is G or S; $X_{12}$ is V or Y; $X_{13}$ is D or G;

$X_{14}$ is N or S; $X_{15}$ is A or S; $X_{16}$ is L or V; $X_{17}$ is K or R; $X_{18}$ is A or S; and $X_{19}$ is L or Q; or a sequence substantially identical thereto;

(SEQ ID NO: 24)
$X_1$VX$_2$LX$_3$ESGGGLVQX$_4$GGSLRLSCAASGRTIDNYAMAWX$_5$RQAPGKX$_6$

X$_7$EX$_8$VX$_9$TIDWGDGGX$_{10}$RYANSVKGRFTISRDNX$_{11}$KX$_{12}$TX$_{13}$YLQM

NX$_{14}$LX$_{15}$X$_{16}$EDTAVYX$_{17}$CAMARQSRVNLDVARYDY WGQGTX$_{18}$VTV

SS, where $X_1$ is E or Q; $X_2$ is K or Q; $X_3$ is V or

E; $X_4$ is A or P; $X_5$ is V or S; $X_6$ is D or G; $X_7$ is

L or R; $X_8$ is F or W; $X_9$ is A or S; $X_{10}$ is A or T;

$X_{11}$ is A or S; $X_{12}$ is G or N; $X_{13}$ is M or L;

$X_{14}$ is N or R; $X_{15}$ is E or R; $X_{16}$ is P or A;

$X_{17}$ is S or Y; and $X_{18}$ is Q or L; or a sequence substantially identical thereto.

More specifically, and without wishing to be limiting in any manner, the antibody or fragment thereof may comprise a sequence selected from any one of:

(SEQ ID NO: 14)
DVQLQASGGGLVQAGGSLRLSCAASGFKITHYTMGWFRQAPGKEREFVSR

ITWGGDNTFYSNSVKGRFTISRDNAKNTVYLQMNSLKPEDTADYYCAAGS

TSTATPLRVDYWGKGTQVTVSS;

(SEQ ID NO: 15)
EVQLVESGGGLVQPGGSLRLSCAASGFKITHYTMGWVRQAPGKGLEWVSR

ITWGGDNTFYSNSVKGRFTISRDNSKNTLYLQMNSLRAEDTAVYYCAAGS

TSTATPLRVDYWGQGTLVTVSS;

(SEQ ID NO: 16)
EVQLVESGGGLVQPGGSLRLSCAASGFKITHYTMGWVRQAPGKGLEWVSR

ITWGGDNTFYSNSVKGRFTISRDNSKNTVYLQMNSLRAEDTAVYYCAAGS

TSTATPLRVDYWGQGTLVTVSS;

(SEQ ID NO: 17)
EVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSS;

(SEQ ID NO: 19)
QVKLEESGGGLVQAGGSLRLSCVASEYPSNFYAMSWFRQAPGKEREFVAG

VSRDGLTTLYADSVKGRFTMSRDNAKNTVDLQMNSVKAEDTAVYYCAIVI

TGVWNKVDVNSRSYHYWGQGTQVTVSS;

(SEQ ID NO: 20)
EVQLVESGGGLVQPGGSLRLSCAASEYPSNFYAMSWFRQAPGKEREFVSG

VSRDGLTTLYADSVKGRFTISRDNSKNTLYLQMNSLRAEDTAVYYCAIVI

TGVWNKVDVNSRSYHYWGQGTLVTVSS;

(SEQ ID NO: 22)
QVKLEESGGGLVQAGGSLRLSCEVSGGTVSPTAMGWFRQAPGKEREFVGH

ITWSRGTTRVASSVKDRFTISRDSAKNTVYLQMNSLKSEDTAVYYCAAST

FLRILPEESAYTYWGQGTQVTVSS;

(SEQ ID NO: 23)
QVQLVESGGGLVQPGGSLRLSCAVSGGTVSPTAMGWFRQAPGKGLEFVGH

ITWSRGTTRYASSVKGRFTISRDNSKNTVYLQMNSLRAEDTAVYYCAAST

FLRILPEESAYTYWGQGTLVTVSS (SEQ ID NO: 25)
QVKLEESGGGLVQAGGSLRLSCAASGRTIDNYAMAWSRQAPGKDREFVAT

IDWGDGGARYANSVKGRFTISRDNAKGTMYLQMNNLEPEDTAVYSCAMAR

QSRVNLDVARYDYWGQGTQVTVSS;

(SEQ ID NO: 26)
QVQLVESGGGLVQPGGSLRLSCAASGRTIDNYAMAWVRQAPGKGLEWVAT

IDWGDGGTRYANSVKGRFTISRDNSKNTMYLQMNSLRAEDTAVYYCAMAR

QSRVNLDVARYDYWGQGTLVTVSS;

and
a sequence substantially identical thereto. The antibody or fragment thereof may be a single-domain antibody.

A substantially identical sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions of the sdAb while maintaining the CDR sequences listed above and the overall structure of the CDR of the antibody or fragment; thus the specificity and binding of the antibody are maintained.

A substantially equivalent sequence may comprise one or more conservative amino acid mutations; wherein the mutant peptide is substantially equivalent with respect to peptide stability and bio-manufacturability. Substantially equivalent may refer to equivalent with respect to fusion molecule stability; for example, the lack of a degradation product, or a low molecular weight band, as seen in SDS PAGE (reducing and non-reducing conditions). It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially equivalent" polypeptides.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 90% identical; in another example, the substantially identical sequences may be at least 90, 91, 92, 93, 94, 95, 96, 97, 98, 99, or 100% identical, or any percentage therebetween, at the amino acid level to sequences described herein. Importantly, the substantially identical sequences retain the activity and specificity of the reference sequence. In a non-limiting embodiment, the difference in sequence identity may be due to conservative amino acid mutation(s). In a non-limiting example, the present invention may be directed to an antibody or fragment thereof comprising a sequence at least 95%, 98%, or 99% identical to that of the antibodies described herein.

The antibody or fragment thereof in the compound of the present invention may be linked to an Fc domain, for example, but not limited to human Fc domains. The Fc domains may be selected from various classes including, but not limited to, IgG, IgM, or various subclasses including, but not limited to IgG1, IgG2, etc. In this approach, the Fc gene is inserted into a vector along with the sdAb gene to generate a sdAb-Fc fusion protein (Bell et al, 2010; Iqbal et al, 2010); the fusion protein is recombinantly expressed then purified. For example, and without wishing to be limiting in any manner, multivalent display formats may encompass chimeric formats of FC5-H3 and its mutational variants linked to an Fc domain. Such antibodies are easy to engineer and to produce, can greatly extend the serum half-life of sdAb (Bell et al., 2010).

The Fc domain in the compound as just described may be any suitable Fc fragment known in the art. The Fc fragment may be from any suitable source; for example, the Fc may be of mouse or human origin. Other preferred Fc or Fc fragment embodiments may modulate, modify or suppress an immunological effector function (Shields 2001). Other highly preferred Fc fragment embodiments may mediate clearance of the fusion peptide from the brain (Caram-Salas N 2011). In a specific, non-limiting example, the Fc may be the mouse Fc2a fragment or human Fc1 fragment (Bell et al, 2010; Iqbal et al, 2010). In a specific, non-limiting example, the multimerized construct may comprise the isolated or purified antibody or fragment as described herein and an Fc of sequence of SEQ ID NO:39; SEQ ID NO:40; SEQ ID NO:41. Accordingly, the BBB-Fc-ABP fusion proteins provided herein may form dimers via the Fc to provide a bivalent, bifunctional BBB-Fc-ABP.

The compound of the present invention comprises an antibody or fragment thereof linked to a polypeptide that binds β-amyloid. The linker may be any polypeptide, comprising neutral or hydrophilic amino acids, of suitable length. In a non-limiting example, the length is preferably less than 12 amino acids, and the polypeptide is GGGSGGGS (SEQ ID NO: 58). Other chemical linkers may be employed using non-peptidic forms such as amide or ester linkages in a correct orientation. For example, SEQ ID NO: 53 provides a fusion protein comprising any suitable linker, wherein any fusion protein of the present invention, i.e. SEQ ID NO: 42-52 may comprise any suitable linker as exemplified in SEQ ID NO: 53. The polypeptide that binds β-amyloid (Aβ) may bind pathologically relevant β-amyloids, such as $A\beta_{1-42}$ aggregates, which are implicated in AD pathology; the polypeptide may bind Aβ with high affinity (in the nM range), inhibit Aβ binding to cellular proteins and $A\beta_{1-42}$-induced cell toxicity in vitro, and binds amyloid deposits in AD transgenic mice brain as well as in the brains from AD patients in vitro. The polypeptide in the compound of the present invention does not bind the reverse peptide $A\beta_{42-1}$.

In a compound provided herein, the polypeptide that binds β-amyloid may comprise a sequence selected from the group consisting of: (SEQ ID NO:27); (SEQ ID NO:28); (SEQ ID NO:29); (SEQ ID NO:30); (SEQ ID NO:31); (SEQ ID NO:32); (SEQ ID NO:33); (SEQ ID NO:34); (SEQ ID NO:35); (SEQ ID NO:36); (SEQ ID NO:37); (SEQ ID NO:38); and a sequence substantially identical thereto. A "substantially identical" sequence is as described above.

Accordingly, the present invention provides a polypeptide that binds β-amyloid and variants thereof (i.e. ABP and ABP variants). The ABP variant may comprise a sequence having SEQ ID NO: 31, for example, the ABP variant provided may comprise a sequence selected from the group consisting of: SEQ ID NO: 31 to SEQ ID NO:38 or a sequence substantially equivalent thereto.

Accordingly, there is provided ABP polypeptide sequences comprising specific systematic and methodical modifications based on detailed biophysical characterization of the ABP. The specific and methodically directed modifications to the ABP polypeptide comprise the novel and unobvious ABP variants of the present invention, as provided in SEQ ID NO:31.

The peptide provided herein may comprise an ABP comprising a sequence that may be selected from the group consisting of SEQ ID NO: 27-SEQ ID NO: 38, and a sequence substantially equivalent thereto.

Figure 14:
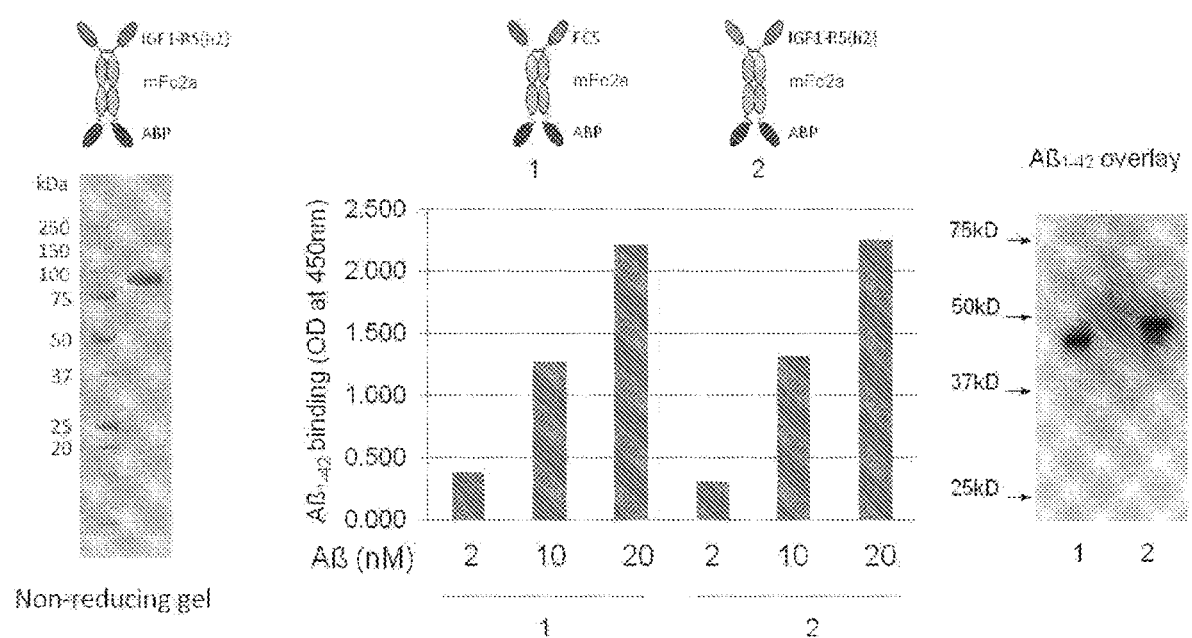
FIG. 14: shows the generation of ABP fusion molecule with a different BBB carrier. To assess the versatility of ABP fusion molecule, ABP was successfully fused with another humanized BBB carrier IGF1R5 (H2). As shown, the bi-functionality of the molecule was retained, ABP's ability to bind Aß oligomer (ELISA and overlay assays) and also IGF1R5's ability deliver ABP across BBB model in vitro (data not shown). This clearly indicates that ABP can be fused to different BBB-crossing single-domain antibodies to be delivered to the brain.

The peptide provided herein may comprise an ABP variant, for example, an ABP comprising a sequence that may be selected from any one of SEQ ID NO: 32 to SEQ ID NO:38, or any equivalent sequence to SEQ ID NO:31. A construct comprising an ABP or an ABP variant, as provided herein, exhibits advantageous improvement in compound stability and bio-manufacturability (as can be seen in FIG. 14).

The fusion proteins and compounds provided herein, exhibit improved therapeutic efficacy. More specifically, the compounds provided comprise specifically modified ABP that allows the generation of stable BBB-Fc-ABP fusion molecule for enhanced bio-manufacturability (production in human mammalian expression system). The specific modifications to ABP provided herein were systematic and methodical modifications based on detailed biophysical characterization of the ABP. The modified ABP provided herein, may comprise, for example, a sequence selected from SEQ ID NO: 32-SEQ ID NO: 38, and a sequence substantially equivalent thereto, such as SEQ ID NO: 31. The compounds provided herein advantageously exhibit improved stability and bio-manufacturability, and a most significant increase in the efficacy of reducing Aß levels in brain; wherein a 50% amyloid reduction was observed within 24 hr of treatment with a construct of the present invention.

By the term "linked", also referred to herein as "conjugated", it is meant that two moieties are joined directly or indirectly (e.g., via a linker), covalently or non-covalently (e.g., adsorption, ionic interaction). A covalent linkage may be achieved through a chemical cross-linking reaction, or through fusion using recombinant DNA methodology combined with any peptide expression system, such as bacteria, yeast or mammalian cell-based systems. When conjugating the antibody or fragment thereof to the polypeptide binding Aβ or Fc, a suitable linker may be used. For example, a suitable linker may be any polypeptide, comprising neutral or hydrophilic amino acids, of suitable length that allows for the conjugation of the components of the BBB-Fc-ABP protein fusion. For example, the linker that allows the components of the fusion protein (for example, in SEQ ID NO: 42-52) to be according linked, and is not limited to the GGGGSGGGGS (SEQ ID NO: 56) or (GGGS)$_n$ (SEQ ID NO: 57) linker highlighted therein and may be any suitable linker (i.e. as in the non-limited fusion protein of SEQ ID NO: 53). In a non-limiting example, the length is preferably less than 12 amino acids, and the polypeptide may be GGGSGGGS (SEQ ID NO: 58). Other chemical linkers may be employed using non-peptidic forms such as amide or ester linkages in a correct orientation. One of skill in the present art would be well aware of linkers or method of linking an antibody or fragment thereof to a polypeptide. Methods for linking an antibody or fragment thereof to a polypeptide or Fc are well-known to a person of skill in the art.

The compound provided herein comprises an antibody or fragment thereof, a polypeptide that binds β-amyloid, and an Fc fragment, linked to provide a construct (also referred to herein as a compound or fusion molecule), wherein the construct comprises a fusion protein and dimers thereof. The antibody or fragment thereof may be linked to a polypeptide that binds β-amyloid via an Fc fragment, or a suitable linker.

The antibody or fragment thereof comprises a sequence selected from any one of: SEQ ID NO:14, SEQ ID NO:14, SEQ ID NO: 15, SEQ ID NO:16, SEQ ID NO:17, SEQ ID NO: 19, SEQ ID NO: 20, SEQ ID NO: 22, SEQ ID NO 23, SEQ ID NO:25, SEQ ID NO:26, and a sequence substantially identical thereto. The antibody or fragment thereof transmigrates the blood brain barrier. The antibody or fragment may be a sdAb; wherein the sdAb may be humanized.

The polypeptide that binds β-amyloid comprises a sequence selected from the group consisting of: SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, and a sequence substantially identical thereto, and preferably a sequence comprising SEQ ID NO: 31.

The Fc fragment comprises a sequence selected from any one of SEQ ID NO:39, SEQ ID NO:40, SEQ ID NO:41, and a sequence substantially identical thereto. The Fc fragment of the present invention may be any suitable Fc fragment with attenuated effector function. The Fc fragment provided in the fusion protein allows for the formation of dimeric structures; wherein for example a single-chain fusion protein comprising a sequence selected from the group consisting of SEQ ID NO: 42 to SEQ ID NO: 53 may form dimeric structures conjugated via the Fc fragment therein.

Accordingly, a compound or construct of the present invention may comprise a sequence selected from the group consisting of SEQ ID NO:42, SEQ ID NO:43, SEQ ID NO:44 SEQ ID NO:45, SEQ ID NO:46, SEQ ID NO:47, SEQ ID NO:48, SEQ ID NO: 49, SEQ ID NO: 50, SEQ ID NO: 51, SEQ ID NO: 52, SEQ ID NO: 53 and a sequence substantially identical thereto, or dimeric structures thereof.

The present invention provides fusion proteins comprising a BBB-crossing single-domain antibody (BBB), an Fc fragment (Fc) and an amyloid-binding peptide (ABP), wherein each moiety may be linked to provide fusion molecules, as illustrated in FIG. 1. For example, in a non-limiting embodiment of the represent invention, the BBB may linked to the N-terminus of the Fc and the ABP linked to the C-terminus of the Fc fragment (FIG. 1A). FIG. 1 shows the corresponding dimers of the single-chain fusion protein comprising BBB-Fc-ABP. The 3 components (i.e. BBB, Fc, and ABP) are depicted in various configurations, as illustrated in FIGS. 1A, 1B, 1C, and 1D. In a specific, non-limiting example of the compound of the present invention, the polypeptide that binds β-amyloid may comprise the sequence SEQ ID NO: 31. In an embodiment the ABP variant comprises the sequence: GTFGTGGASAQAS-LASKDKTPKSKSKKGGSTQLKSRVKNI (SEQ ID NO: 36) referred to herein as ABP(6G) and a sequence substantially equivalent thereto.

The antibody or fragment thereof may comprise the sequence

```
                                          (SEQ ID NO: 17)
EVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSS referred to herein as

FC5-H3.
```

The antibody or fragment thereof may further comprise the sequence of a human Fc, such as

```
                                          (SEQ ID NO: 40)
AEPKSSDKTHTCPPCPAPELLGGPSVFLFPPKPKDTLMISRTPEVTCVVV

DVSHEGPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSL SPG, also referred to herein as hFc1X7.
```

Without wishing to be limiting in any manner, the compound of the present invention may comprise the sequence:

```
                                          (SEQ ID NO: 47)
EVQLVESGGGLVQPGGSLRLSCAASGFKITHYTMGWFRQAPGKGLEFVSR

ITWGGDNTFYSNSVKGRFTISRDNSKNTVYLQMNSLRAEDTAVYYCAAGS

TSTATPLRVDYWGQGTLVTVSSAEPKSSDKTHTCPPCPAPELLGGPSVFL

FPPKPKDTLMISRTPEVTCVVVDVSHEGPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPGGGGSGGGGSGTFGTGGASAQASLASKDKTPKSKSKKGGSTQLKSRV

KNI, also referred to herein as

FC5-H3-hFc1X7-ABP(6G).
```

Table Summary of some representative BBB-Fc-ABP fusion protein constructs.

| BBB | Fc | ABP |
|---|---|---|
| FC5 (SEQ ID NO: 14) | mFc2a (SEQ ID NO: 39) | ABP (SEQ ID NO: 30) |
| FC5(H3) (SEQ ID NO: 17) | mFc2a (SEQ ID NO: 39) | ABP (SEQ ID NO: 30) |
| FC5(H3) (SEQ ID NO: 17) | hFc1x7 (SEQ ID NO: 40) | ABP (SEQ ID NO: 30) |
| FC5(H3) (SEQ ID NO: 17) | hFc1x7 (SEQ ID NO: 40) | ABP(G) SEQ ID NO: 32 |

| BBB | Fc | ABP |
|---|---|---|
| FC5(H3) (SEQ ID NO: 17) | hFc1x7 (SEQ ID NO: 40) | ABP(GG-G) SEQ ID NO: 35 |
| FC5(H3) (SEQ ID NO: 17) | hFc1x7 (SEQ ID NO: 40) | ABP(6G) SEQ ID NO: 36) |
| FC5(H3) (SEQ ID NO: 17) | hFc1X0 (SEQ ID NO: 41) | ABP(GG-G) SEQ ID NO: 35 |
| FC5(H3) (SEQ ID NO: 17) | hFc1x7 (SEQ ID NO: 40) | ABP(trc) SEQ ID NO: 38) |
| IGF1R-5(H2) (SEQ ID NO: 26) | mFc2a (SEQ ID NO: 39) | ABP (SEQ ID NO: 30) |

It is noted that in the above-table, the BBB-Fc-ABP fusion protein constructs may also comprise a linker (L) wherein the BBB-Fc-ABP construct is a BBB-Fc-L-ABP fusion protein of the present invention, wherein L may be GGGSGGGGS (SEQ ID NO: 55) or any suitable linker, as exemplified in the consensus linker sequence in SEQ ID NO:53.

The compound of the present invention, as provided in the fusion protein of SEQ ID NO:47 also referred to herein as FC5-H3-hFc1×7-L-ABP(6G), may comprise variations in each of the components comprised therein, for example, ABP may be ABP (GG-G), as provided in SEQ ID NO: 46. The linker sequence provided therein (as highlighted for example, in SEQ ID NO:42 to SEQ ID NO: 53) may be any linker that allows for the linking of the BBB-Fc-ABP fusion protein. The compound of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, His$_5$, or His$_6$), or a combination thereof. In another example, the additional sequence may be a biotin recognition site such as that described by Cronan et al (WO 95/04069) or Voges et al (WO/2004/076670). As is also known to those of skill in the art, linker sequences may be used in conjunction with the additional sequences or tags, or may serve as a detection/purification tag.

The present invention also encompasses nucleic acid sequences encoding the compounds as described herein. Given the degeneracy of the genetic code, a number of nucleotide sequences would have the effect of encoding the polypeptide, as would be readily understood by a skilled artisan. The nucleic acid sequence may be codon-optimized for expression in various micro-organisms. The present invention also encompasses vectors comprising the nucleic acids as just described. Furthermore, the invention encompasses cells comprising the nucleic acid and/or vector as described.

The present invention further encompasses a composition comprising one or more than one compound as described herein and a pharmaceutically acceptable diluent, excipient, or carrier. The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form or powder form (for example, but limited to lyophilised or encapsulated). For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. It would be within the competency of a person of skill in the art to prepare suitable compositions comprising the present compounds.

A method of treating Alzheimer's disease is also provided, in which a compound or composition of the present invention is administered to a subject in need thereof. Any appropriate route of administration may be utilized, including but not limited to intravenous, intraperitoneal, parenteral, intracranial, intramuscular, subcutaneous, oral, or nasal. The optimal dose for administration and route of administrations are generally determined experimentally.

A method of reducing toxic ß-amyloid levels in the cerebrospinal fluid (CSF) and brain parenchyma of subjects having increased ß-amyloid levels is provided. More specifically, toxic ß-amyloid levels in the cerebrospinal fluid (CSF) and brain parenchyma of subjects is reduced as early as 24 hours of a single parenteral administration of the composition of the present invention.

The present invention will be further illustrated in the following examples. However, it is to be understood that these examples are for illustrative purposes only and should not be used to limit the scope of the present invention in any manner.

Example 1: Construction of the BBB-Fc-L-ABP Fusion Molecules

Fusion molecules comprising:
a) the FC5 sdAb (SEQ ID NO:14), a murine Fc (SEQ ID NO:39) and ABP (SEQ ID NO: 30),
b) a humanized version of FC5 (FC5-H3; SEQ ID NO: 17), a human Fc (SEQ ID NO: 40) and ABP (SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38),
c) a humanized version of IGF1R-5 sdAb (IGF1R-5-H2; SEQ ID NO: 26), a murine Fc (SEQ ID NO:39) and ABP (SEQ ID NO: 30)

were prepared. A schematic of the fusion protein construct is shown in FIG. 1. The fusion protein comprises a BBB-crossing single-domain antibody, an Fc fragment and an amyloid-binding peptide.

Example 2: Production of BBB-Fc-L-ABP Fusion Molecules

The constructs FC5-mFc-ABP and humanized FC5(H3)-hFc-ABP described in Example 1 were expressed in CHO cells, and the expressed compounds were purified on MabSelect Sure affinity columns Constructs comprising FC5 variants FC5 and FC5-H3 V$_H$H fused to N-terminal of mouse or human Fc antibody fragment fused to ABP variants at their C-terminus as described in example 1 were prepared, expressed, and purified.

The FC5-Fc-ABP variant DNAs (DNA synthesis suppliers) were cloned into mammalian expression vector pTT5

(Durocher 2002). Polyplexes for a final concentration of 1 mg of DNA per liter of cells were pre-formed by mixing a combination of plasmid vector (80%), pTT-AKTdd (15%, activated mutant of Protein Kinase B), and pTTo-GFP (5%, to monitor transfection efficiency) with PEI MAX solution (Polysciences cat no 24765). The PEI:DNA ratio was 4:1 (W:W), both prepared in supplemented F17 medium (4 mM Glutamine, 0.1% Kolliphor). The mixture was incubated for 5 minutes at room temperature prior to addition to the cell culture. The volume of the DNA/PEI polyplexe represent 10% of final culture volume (e.i. 100 ml per 1 L culture). Twenty four hours post-transfection, the cultures were fed with tryptone N1 at a final concentration of 1% (with 40% w/v solution, Organotechnie) and 0.5 mM valproic acid (200 mM solution). The transfection/production were monitored for cell density and viability as well as for productivity titer (mg of Fc per L) and were harvested (supernatant) by centrifugation when the cell viability reach a minimum of 65%. Clarified cell culture medium was filtered through a 0.45 µm membrane prior to its application on a column packed with 5 ml of protein-A MabSelect SuRe resin (GE Healthcare). After loading, the column was washed with 5 volumes of phosphate-buffered saline pH 7.1 (PBS) and the antibody was eluted with 100 mM sodium citrate buffer pH 3.0. Fractions containing the eluted antibody were pooled and a buffer exchange was performed by loading on a desalting Econo-Pac column (BioRad) equilibrated in PBS. Desalted antibody was then sterile-filtered by passing through a Millex GP (Millipore) filter unit (0.22 µm) and aliquoted.

SDS-PAGE and Aß overlay: Protein samples, prepared in Laemmli sample buffer (heated at 70° C. for non-reducing and at 95° C. for reducing gels, BME or DTT), were separated by SDS-PAGE on 12% Tris-Tricine gels or TGX4-15% gels (BioRad). Gels were either stained with Coomassie blue or the proteins were transferred to PVDF or nitrocellulose membranes for Western blot/Aß overlay assay. The immunoblots were blocked with non-fat dry milk and then exposed to Aß preparations for 45 min at room temperature (50-100 nM) and the bound Aß was detected using 6E10 antibody as described previously (Chakravarthy et al. 2013).

ELISA: Aß-binding assays were carried out as described by Chakravarthy et al (2013). Maxisorp 96-well ELISA plates (Nunc) were coated with (100-500 ng/well) either free ABP (synthetic) or various FC5-ABP constructs overnight at 4° C. in PBS. The wells were blocked with 1% BSA in TBS-T for 30 min and then incubated with $Aß_{1-42}$ preparations consisting predominantly of either monomer and dimers (Mo) or higher oligomers (Oli) in TBS-T at RT for 45 min with gentle agitation. Following three TBS-T washes, bound Aß was detected by incubating HRP-conjugated Aß-specific antibody (6E10 or 4G8) for 90 min at RT in TBS-T. The bound antibody was detected with Sure-Blue™ TMB reagent kit (KPL) by colorimetric measurement at 450 nm according to manufacturer's instructions.

Figure 2A:
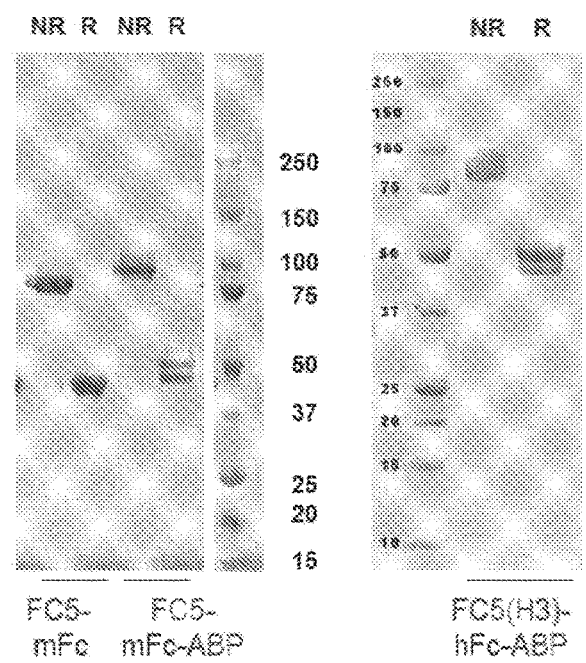
As shown in FIG. 2A, a Coomassie blue stained gel after separation of FC5 fusion molecules by SDS-PAGE (NR— non-reducing and R— reducing conditions) showing successful production of recombinant fusion molecule.
Figure 2B:
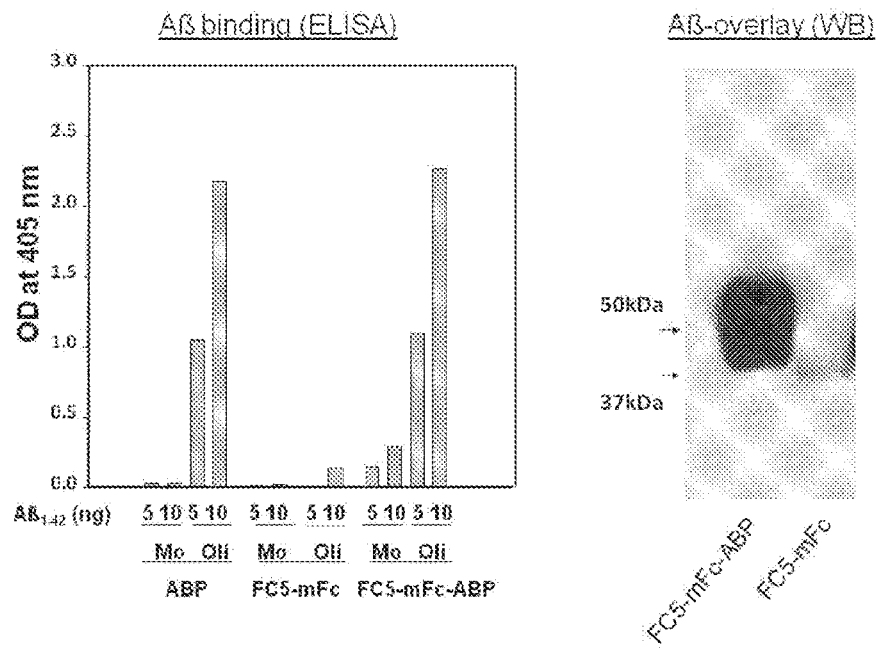
FIG. 2B and FIG. 2C: Aβ-oligomer binding of free ABP and BBB-Fc-ABP fusion protein by ELISA and Western blot (WB) Overlay assay. Free or fused ABP was immobilized on ELISA plate and exposed to Aβ. Bound Aβ was detected with Aβ-specific antibody 6E10 or 4G8. The fusion molecules were also separated by SDS-PAGE, transferred to PVDF paper and exposed to Aβ. Bound Aβ was detected with specific antibody as above. Results show that ABP retained its Aβ oligomer binding ability after fusion with the BBB carrier. Mo: Aβ monomers; Oli: Aβ Oligomers
Figure 3:
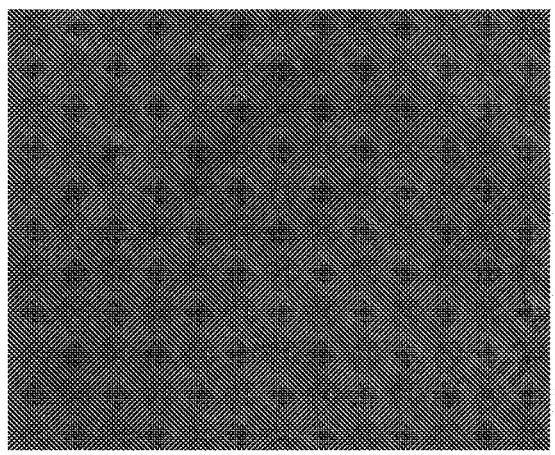
FIG. 3: shows an immunohistofluorescence assay of the binding of FC5-Fc-ABP to amyloid deposits in AD-Tg mice (B6.Cg-Tg, Jackson Lab). ABP retains the ability to bind naturally produced Aβ aggregates in AD-Tg mouse brain as shown by immunohistofluorescence assay. Brain sections from wild type and AD-transgenic mice were incubated with IR 800-labelled FC5-mFc-ABP and the bound fusion molecule was visualized under fluorescence microscope. Selective binding (bright spots) were seen in brain sections from AD-Tg mice that produce Aβ deposits and not in brain sections from wild type mice that does not produce amyloid deposits.
Figure 3:
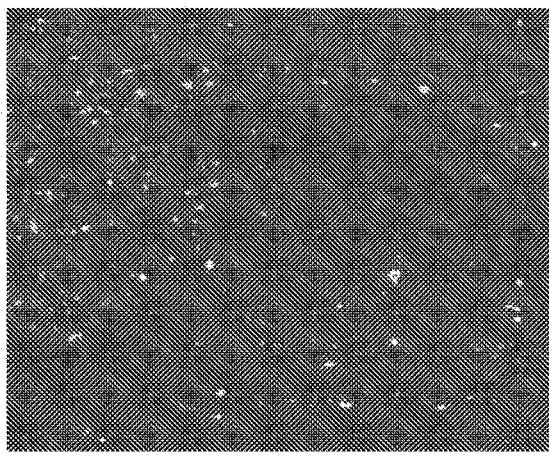

A Coomassie blue stained gel after separation of FC5 fusion molecules by SDS-PAGE (NR—non-reducing and R—reducing conditions) indicating successful production of recombinant fusion molecule is shown in FIG. 2A. Aß-oligomer binding of free ABP and FC5-Fc-ABP fusion protein by ELISA and Western blot (WB) Overlay assay is shown in FIGS. 2B and C. Free or fused ABP was immobilized on ELISA plate by coating samples in phosphate buffered saline (PBS) overnight at 4° C. and exposed to Aß preparations as described by Chakravarthy et al., 2013. Bound Aß was detected with Aß-specific antibody 6E10 or 4G8 (Chakravarthy et al., 2013). The fusion molecules were also separated by SDS-PAGE, transferred to PVDF paper and exposed to Aß oligomers. Bound Aß was detected with specific antibody as above. Results show that ABP retained its Aß oligomer binding ability after fusion with the BBB carrier. Mo: Aß monomers; Oli: Aß Oligomers Example 3: Binding of BBB-Fc-L-ABP Fusion Molecules to Aa Deposits in AD-Tg Mice (B6.Cg-Tg, Jackson Lab) In Vitro The constructs produced in Example 2 were submitted to immunohistofluorescence assay to evaluate whether the FC5-Fc-ABP fusion molecules retained the ability to bind naturally-produced amyloid deposits in mouse brain as described (Chakravarthy et al., 2014). Frozen hemi-brains from wild type (Wt) and AD transgenic (AD-Tg) mice were embedded in OCT and 10-µm sections were prepared using a Jung CM 3000 cryostat and stored at −80° C. Tissue sections were thawed and OCT peeled from sections with a razor blade and then incubated with Dako protein blocking reagent for 30 min at room temperature. Blocking agent was removed and sections were gently washed in TBS. IR 800-labelled FC5-mFc-ABP (1:250 dilution of 5.0 µg/µl solution) in antibody diluent was added and incubated for 1 h at room temperature. Sections were then washed twice with TBS, rinsed in Milli Q water, excess rinse solution removed and sections were cover-slipped with Dako Fluorescent Mounting Media. Sections visualized under fluorescence microscope (FIG. 3). Selective binding (bright spots) was seen in brain sections from AD-Tg mice that produce Aß deposits and not in brain sections from Wt mice that does not produce amyloid deposits, indicating that ABP in the FC5-Fc-ABP construct retains the ability to bind naturally produced Aß aggregates in AD-Tg mouse brain. In the BBB-Fc-ABP constructs provided, the BBB may be FC5 or an anti-IGF1R antibody.

Example 4: BBB Transmigration of FC5-Fc-L-ABP Fusion Molecules In Vitro

Figure 4:
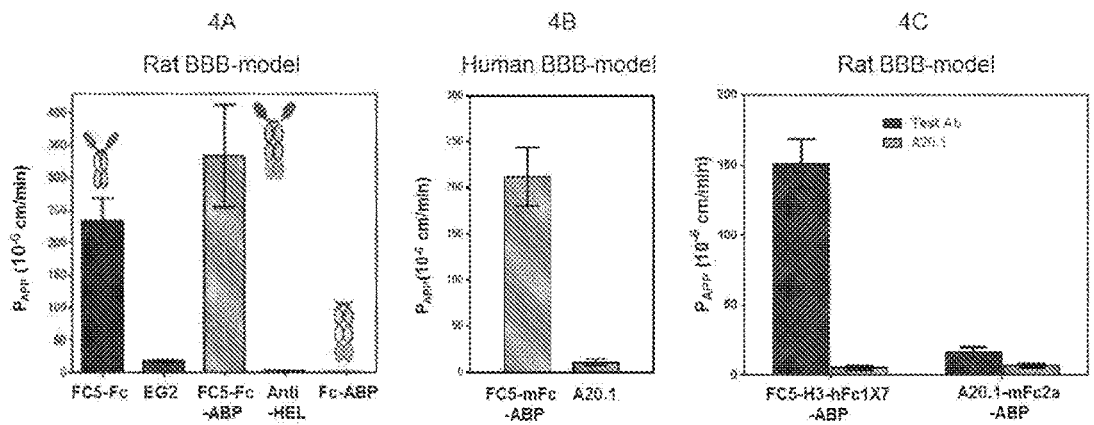
FIG. 4: shows BBB permeability of FC5 is retained after fusion with ABP in vitro. Blood brain barrier crossing of FC5-ABP fusion molecules was assessed in in vitro BBB models from rat and human. Fusion molecules crossing BBB were detected by nanoLC-MRM method (FIG. 4A, FIG. 4B and FIG. 4C) and by Western blot analysis using Fc-specific antibody (FIG. 4D, done in triplicate). FC5-mFc-ABP crossed the BBB as effectively as FC5-mFc, whereas Fc-ABP without the BBB carrier moiety FC5 did not traverse across the brain endothelial cell monolayer. As expected, control single domain antibodies EG2 and A20.1, or control full IgG (anti-HEL) did not cross the blood brain barrier. Similar results were obtained with humanized FC5-H3-hFc-ABP fusion protein (FIG. 4C and FIG. 4D).
Figure 4:
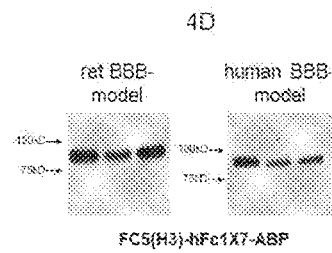

BBB-crossing of FC5-Fc-ABP fusion molecules was assessed in in vitro BBB models from rat and human (FIG. 4). Fusion molecules crossing BBB were screened in in vitro BBB permeability assay, using a single-time point for Papp determination. The quantification of variants was done by MRM-ILIS (FIGS. 4A, 4B and 4C).

SV40-immortalized Adult Rat Brain (SV-ARBEC) and Human Brain Endothelial Cells (HBEC) were used to generate an in vitro blood-brain barrier (BBB) model as described (Garberg et al., 2005; Haqqani et al., 2013). Sv-ARBEC (80,000 cells/membrane) were seeded on a 0.1 mg/mL rat tail collagen type I-coated tissue culture inserts (pore size-1 µm; surface area 0.9 $cm^2$, Falcon) in 1 ml of growth medium. The bottom chamber of the insert assembly contained 2 ml of growth medium supplemented with the immortalized neonatal rat astrocytes-conditioned medium in a 1:1 (v/v) ratio. Equimolar amounts (5.6 µM) of positive (FC5 constructs) or negative controls (A20.1, a *Clostridium difficile* toxin A binding $V_HH$; and EG2, an EGFR binding $V_HH$), and Fc-ABP from Example 1 were tested for their ability to cross the rat or human in vitro BBB model. Following exposure of equimolar amounts of the sdAb to the luminal side of the BBB, samples were taken after 15, 30 and 60 min from the abluminal side. The sdAb content of each sample was then quantified by mass spectrometry (multiple reaction monitoring-isotype labeled internal standards; MRM-ILIS) (FIG. 4A, 4B, 4C).

MRM-ILIS: The methods are all as described in Haqqani et al. (2013). Briefly, to develop the SRM (selected reaction monitoring also known as multiple reaction monitoring (MRM)) assay for $V_HH$, each $V_HH$ was first analyzed by nanoLC-MS/MS using data-dependent acquisition to identify all ionizible peptides. For each peptide, the 3 to 5 most intense fragment ions were chosen. An initial SRM assay was developed to monitor these fragments at attomole amounts of the digest (about 100-300 amol). Fragments that showed reproducible intensity ratios at low amounts (i.e., had Pearson r2≥0.95 compared to higher amounts) were considered stable and were chosen for the final SRM assay. To further optimize the assay, elution times for each peptide were also included, with care taken to not choose peptides that have close m/z (mass-to-charge ratio) and elution times.

A typical multiplexed SRM analysis of $V_HH$ in cell media or body fluids (serum or cerebrospinal fluid (CSF)) involved spiking known amount of ILIS (0.1-10 nM) followed by injecting 100-400 ng of CSF or cultured media proteins (0.3-1 µL) or about 50-100 ng of serum proteins (1-3 nanoliters) into the nanoLC-MS system. The precursor m/z of each target peptide ion was selected in the ion trap (and the remaining unrelated ions were discarded) at the specified elution time for the target, followed by collision induced dissociation (CID) fragmentation, and selection of only the desired fragment ions in the ion trap for monitoring by the detector. For quantification analysis, raw files generated by the LTQ (ThermoFisher) were converted to the standard mass spectrometry data format mzXML and intensities were extracted using an in-house software called Q-MRM (Quantitative-MRM; see Haqqani et al. 2013), which is a modified version of MatchRx software. For each $V_HH$, extracted-ion chromatograms were generated for each of its fragment ion that consisted of combined intensities within 0.25 Da of the fragment m/z over the entire elution time. To obtain a final intensity value for each fragment, all intensities within 0.5 min of the expected retention times were summed. A $V_HH$ was defined as detectable in a sample if the fragments of at least one of its peptides showed the expected intensity ratios, i.e., the final intensity values showed a strong Pearson correlation r≥0.95 and p<0.05 compared with the final intensities values of its corresponding pure $V_HH$.

Samples containing mixtures of $V_HH$ (media, serum, CSF) were reduced, alkylated and trypsin-digested as previously described (Haqqani et al., 2012; Gergov et al., 2003). The digests (tryptic peptides) were acidified with acetic acid (5% final concentration) and analyzed on a reversed-phase nanoAcquity UPLC (Waters, Milford, Mass.) coupled to LTQ XL ETD or LTQ Orbitrap ETD mass spectrometer (ThermoFisher, Waltham, Mass.). The desired aliquot of the sample was injected and loaded onto a 300 µm I.D.×0.5 mm 3 µm PepMaps C18 trap (ThermoFisher) then eluted onto a 100 µm I.D.×10 cm 1.7 µm BEH130C18 nanoLC column (Waters) using a gradient from 0%-20% acetonitrile (in 0.1% formic) in 1 minute, 20%-46% in 16 min, and 46%-95% in 1 min at a flow rate of 400 nL/min. The eluted peptides were ionized into the mass spectrometer by electrospray ionization (ESI) for MS/MS and SRM analysis using CID for fragmentation of the peptide ions. The CID was performed with helium as collision gas at normalized collision energy of 35% and 30 ms of activation time. Ion injection times into linear ion trap were adjusted by the instrument using an automatic gain control (AGC) target value of $6 \times 10^3$ and a maximum accumulation time of 200 ms.

Determination of the apparent permeability coefficient: Quantified values can be directly plotted or the $P_{app}$ (apparent permeability coefficient) values can be determined with the given formula [Qr/dt=cumulative amount in the receiver compartment versus time; A=area of the cell monolayer; C0=initial concentration of the dosing solution] and plotted. The $P_{app}$ value is commonly used to determine the ability of a molecule to cross the BBB. $P_{app}$ values are a measure of the specific permeability of the compound across brain endothelial monolayer.

The specific peptides used for detection and quantification of FC5 constructs are shown in Table 1 below.

TABLE 1

| Type | Tryptic MRM peptide | SEQ ID NO | Protein |
|---|---|---|---|
| FC5 peptide | ITWGGDNTFYSNSVK + ILIS | 59 + 66 | FC5-mFc-ABP |
| mFc peptide | NTEPVLDSDGSYFMYSK | 60 | FC5-mFc-ABP, host IgGs |
| ABP peptide | ASAQASLASK | 61 | FC5-mFc-ABP |
| IGF1R5-H2 peptide | GLEWVATIDWGDGGTR | 62 | IGF1R5-H2-mFc-ABP |
| IGF1R5-H2 peptide | ADETAVYYCAMAR | 63 | IGF1R5-H2-mFc-ABP |
| Aß | LVEFAEDVGSNK | 64 | Host APP, Aß1-42 or Aß1-40 |
| Alubmin | APQVSTPTLVEAAR | 65 | Host albumin |

The samples were also analyzed by Western blot analysis using Fc-specific antibody (FIG. 4D, done in triplicate) as described in Example 2. FC5-mFc-ABP crossed the blood brain barrier as effectively as FC5-mFc, whereas Fc-ABP without the BBB carrier moiety FC5 did not traverse across the brain endothelial cell monolayer. As expected, control single domain antibodies EG2 and A20.1, or control full IgG (anti-HEL) did not cross the blood brain barrier. Similar results were obtained with humanized FC5(H3)-hFc-ABP fusion protein (FIG. 4C and FIG. 4D). Similar results were obtained with IGF1R5-mFc-ABP ABP (FIGS. 17 A and B).

Example 5: BBB Transmigration and Pharmacokinetics of FC5-Fc-L-ABP Fusion Molecules In Vivo The ability of the constructs of Example 2 to transmigrate the blood brain barrier into the brain, specifically into the cerebrospinal fluid (CSF), was evaluated in vivo, as well as to quantify the construct presence in CSF and serum. FC5-mFc-ABP was administered intravenously into rats via tail vein at the indicated doses (2.5, 6.25, 12.5, and 25 mg/kg).

Serum and CSF were serially collected. FC5-Fc-ABP levels were quantified using nanoLC-MRM method.

The technique used for multiple sampling of cisterna magna CSF was developed at NRC by modification of previously described methods (Huang et al., 1995; Kornhuber et al., 1986)). All animals were purchased from Charles River Laboratories International, Inc. (Wilmington, Mass., USA). Animals were housed in groups of three in a 12 h light/dark cycle at a temperature of 24° C., a relative humidity of 50±5%, and were allowed free access to food and water. All animal procedures were approved by the NRC's Animal Care Committee and were in compliance with the Canadian Council of Animal Care guidelines. Male Wistar rats aged 8-10 weeks (weight range, 230-250 g) were used in all studies.

In all experiments, test antibodies (FC5 Fc-fusions) were administered intravenously into tail vein in equimolar doses (7 mg/kg). CSF sample collections were made from cisterna magna by needle puncture up to five times over 96 hours. For sample collection rats were briefly and lightly anesthetized with 3% isoflurane, placed in a stereotaxic frame with the head rotated downward at a 45° angle. A 2-cm midline incision between the ears beginning at the occipital crest was made and muscles separated to expose dura mater covering cisternae magna. A 27G butterfly needle (QiuckMedical, Cat #SV27EL) with tubing attached to 1 ml syringe was used to puncture dura and aspirate the ~20 µl of CSF. The CSF was then transferred into the sample glass vial (Waters, Cat #186000384c) and placed in −80° C. freezer until further analysis.

Blood samples were collected from the tail vein in a commercially available tube (BD microtainer, Cat #365956). After clotting at room temperature for 15-30 minutes, the clot was removed by centrifuging at 1100 rcf (3422 rpm) for 10 min; serum was then transferred into a clean glass vial (Waters, Cat #186000384c), frozen on dry ice and stored at −80° C. until further analysis. At the end of collection, rats were sacrificed by cardiac puncture. Blood and CSF PK analyses were performed using WinLin 6.0 program.

Serum and CSF samples were analyzed by mass spectrometry and nanoLC-SRM based quantification as described in Example 4 using peptide signatures shown in Table 1.

CSF collection is a delicate procedure during which CSF can be easily contaminated with blood. Since the amounts of $V_HH$ s were expected to be much smaller in the CSF (<0.1%) than blood, even a slight contamination with blood could seriously compromise the value of an individual CSF sample. It was therefore necessary to develop stringent exclusion criteria for blood-contaminated CSF samples. To evaluate blood-CSF albumin ratio, a nanoLC-SRM method was developed for quantifying albumin levels in plasma and CSF. An albumin peptide APQVSTPTLVEAAR (SEQ ID NO: 65) was selected based on its unique retention time and m/z value (Mol Pharm) in order to have minimum interference with other peptide peaks in the multiplex assay. The intensity of the peptide was quantified in both CSF and plasma samples using SRM as described above. The albumin ratio was calculated as follows for each rat:

Albumin Ratio=Intensity per nL of plasma analyzed/ Intensity per nL of CSF analyzed A ratio of 1500 and below was considered as blood contaminated.

Figure 5:
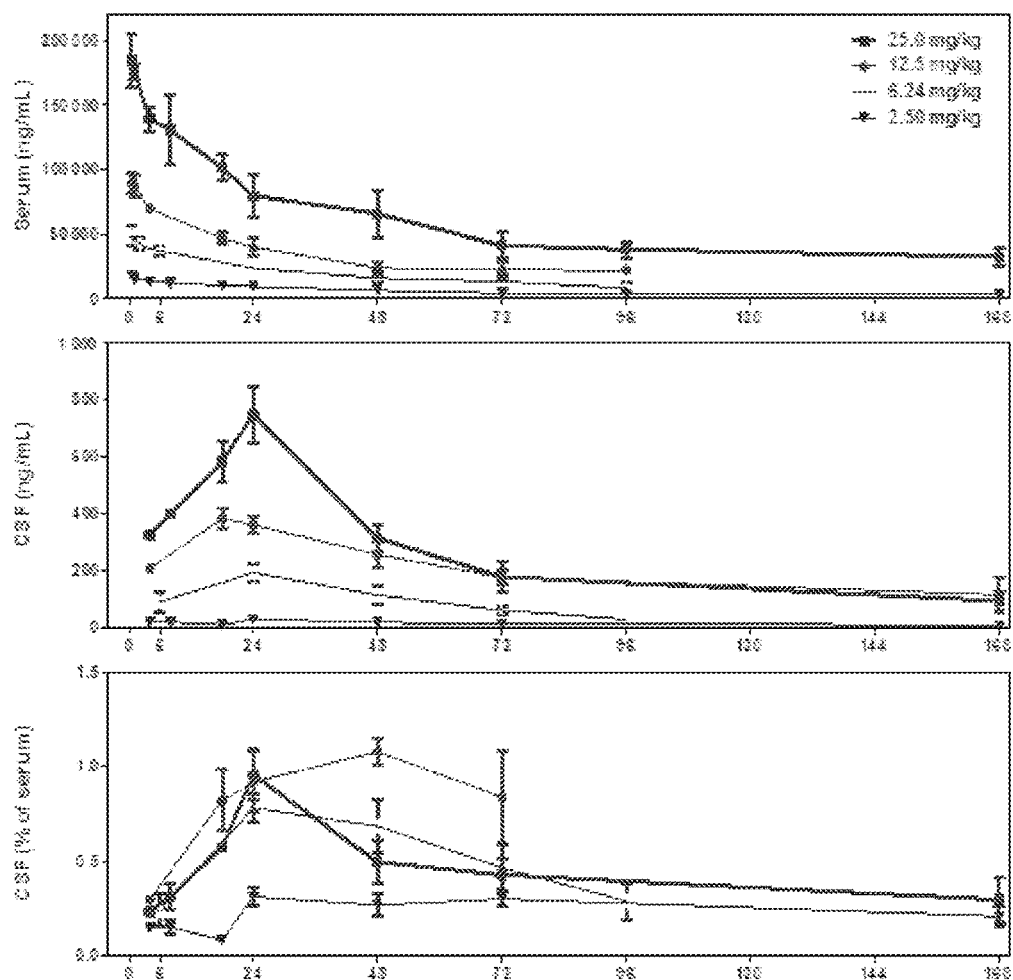
FIG. 5: shows serum and CSF pharmacokinetics of FC5-Fc-ABP in vivo. FC5-mFc-ABP was administered intravenously into rats via tail vein injection at the indicated doses (2.5, 6.25, 12.5, and 25 mg/kg). Serum and CSF were serially collected. FC5-Fc-ABP levels were quantified using nanoLC-MRM method.

As shown in FIG. 5, FC5-mFc-ABP appeared in the CSF in a time- and dose-dependent manner with Cmax between 12 and 24 h, indicating transport of ABP by FC5 into brain and CSF compartments in vivo (A). Serum PK parameters (FIG. 5 and Table 2 below) show that alpha- and beta-half-life of FC5-mFc-ABP is similar to that of a full IgG (a benchmark antibody containing rat Fc) and is substantially higher than that of ABP or FC5 or FC5-ABP without Fc.

TABLE 2

| Parameter | Estimate | Units | CV (%) |
|---|---|---|---|
| mAb | | | |
| V1 | 114.6 | mL/kg | 2.3 |
| V2 | 74.4 | mL/kg | 6.5 |
| CL | 0.664 | mL/(kg*hr) | 1.9 |
| CLd | 2.682 | mL/(kg*hr) | 41.8 |
| Alpha $T_{1/2}$ | 11.2055 | hr | 38.0 |
| Beta $T_{1/2}$ | 205.279 | hr | 2.2 |
| Vss | 189.0 | mL/kg | 1.4 |
| FC5mFc-ABP (FC5 domain) | | | |
| V1 | 144.5 | mL/kg | 2.2 |
| V2 | 218.4 | mL/kg | 27.2 |
| CL | 1.056 | mL/(kg*hr) | 26.5 |
| CLd | 3.789 | mL/(kg*hr) | 10.6 |
| Alpha $T_{1/2}$ | 14.36 | hr | 14.3 |
| Beta $T_{1/2}$ | 263.8 | hr | 41.3 |
| Vss | 362.9 | mL/kg | 16.3 |

Figure 6:
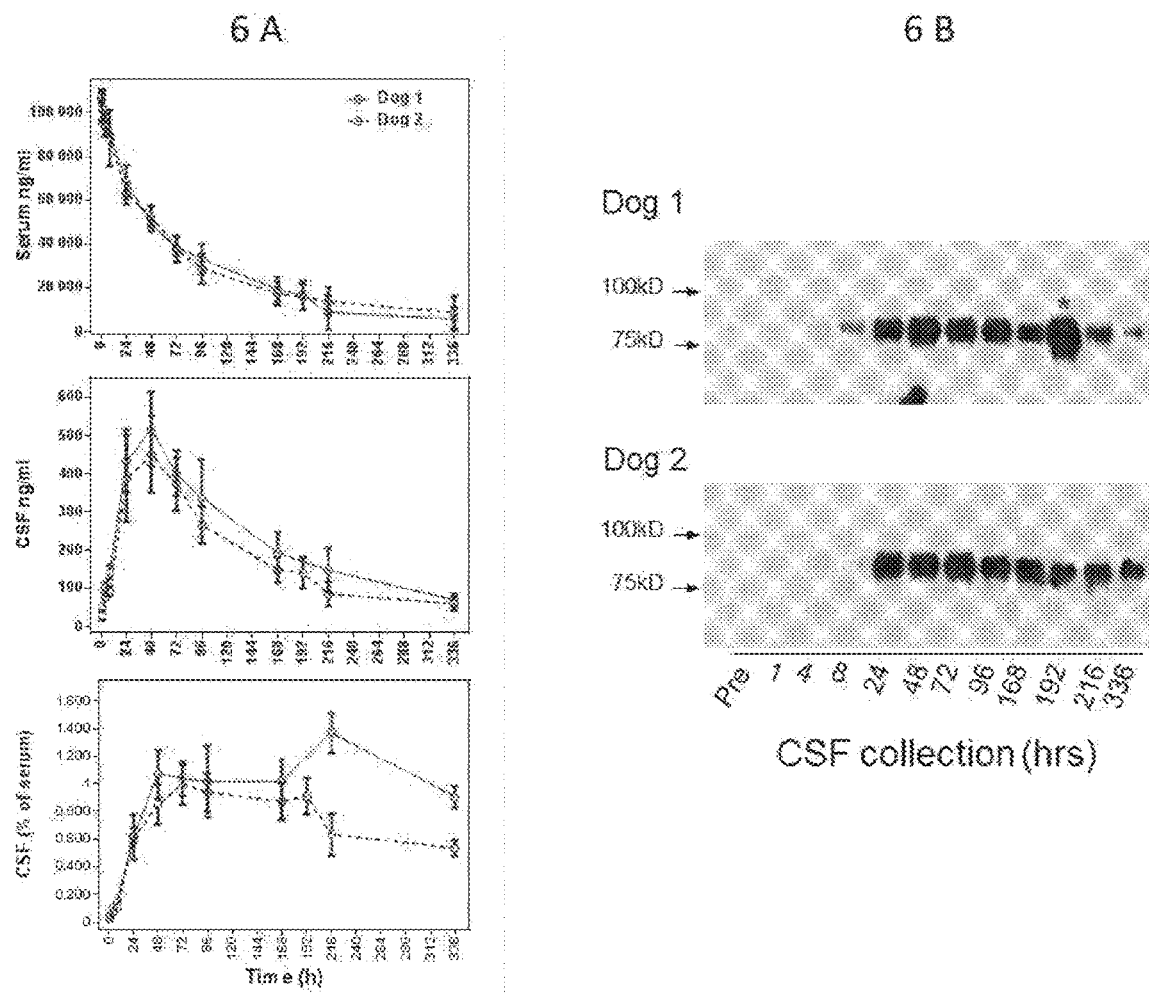
FIG. 6: shows serum and CSF PK profile of FC5-mFc-ABP in beagle dog. FC5-mFc-ABP was administered by intravenous injection to 10-12-year old beagle dogs and serum and CSF were serially collected and analyzed by nanoLC-MRM (FIG. 6A) and by Western blot using Fc-specific antibody (FIG. 6B). Asterisks indicates blood-contaminated sample (not shown in MRM analyses). As can be seen, FC5-mFc-ABP appeared in the CSF in a time-dependent manner indicating transport of ABP by FC5 across dog blood brain barrier in vivo. The PK parameters and CSF exposure were analyzed by WinNonlin software and are shown in Table 2 below.

Dose range: 2.5 mg/kg, 6 mg/kg, 12 mg/kg, 25 mg/kg,

Serum half life (both distribution phase and terminal) are similar between 'benchmark mAb' and FC5mFc-cargo Example 6: Delivery of FC5-ABP Construct to the Brain in Non-Rodent Larger Animal Serum and CSF PK profile of FC5-mFc-ABP was assessed in beagle dog. FC5-mFc-ABP was administered by intravenous injection to 10-12-year old beagle dogs and serum and CSF were serially collected and analyzed by nanoLC-MRM (left panel) and by Western blot using Fc-specific antibody (FIG. 6B) as described above in Example 5. Asterisks indicates blood-contaminated sample (not shown in MRM analyses). As can be seen, FC5-mFc-ABP appeared in the CSF in a time-dependent manner indicating transport of ABP by FC5 across dog blood brain barrier in vivo, confirming the translational nature of the BBB carrier. The PK parameters and CSF exposure were analyzed by WinNonlin software and are shown in Table 3 below.

TABLE 3

| | | Dog 1 | | Dog 2 | |
|---|---|---|---|---|---|
| Parameter | Unit | Mean Estimate | SD | Mean Estimate | SD |
| $t_{1/2}$ | h | 96 | 21 | 89 | 21 |
| AUC 0-t | ng/ml * h | 8.80E+06 | 1.99E+06 | 8.84E+06 | 2.16E+06 |
| AUC 0-inf_obs | ng/ml * h | 1.01E+07 | 2.21E+06 | 1.04E+07 | 2.76E+06 |
| Cl_obs | ml/h/kg | 1.54 | 0.36 | 1.53 | 0.48 |
| Vss_obs | ml/h/kg | 193 | 7 | 205 | 10 |
| Alpha half life | h | 19 | 10 | 13 | 8.5 |
| Beta half life | h | 114 | 37 | 166 | 151 |
| $AUC_{0-t,csf}/AUC_{0-t,serum}$ | % | 0.88 | 0.09 | 0.52 | 0.04 |

Example 7: BBB Permeability

Figure 7:
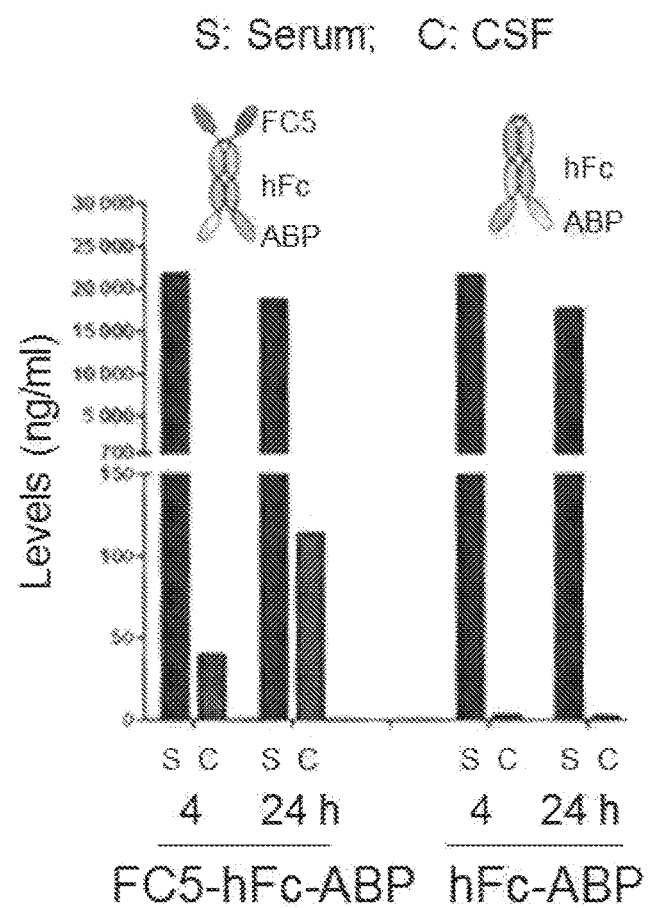
FIG. 7: shows BBB permeability and CSF appearance of FC5 fused with human Fc (hFc) and chemically linked to ABP (FC5-hFc-ABP) in vivo (rat model). FC5-hFc was linked with ABP-cystamide using a heterobifunctional cross-linker sulfo-SMCC (sulfosuccinimidyl 4-[N-maleimidomethyl] cyclohexane-1-carboxylate) according manufacturer's instructions (ThermoFisher Scientific). Chemically conjugated molecule was administered intravenously into rats via tail vein at 6.25 mg/kg and serum and CSF samples were collected at 4 and 24 hrs and analyzed by nanoLC-MRM. FC5-hFc-ABP appears in the CSF in a time-dependent manner in contrast to Fc-ABP without the BBB carrier. It should be noted that in this chemically linked construct, C-terminus of ABP is linked to Fc fragment (random region) and N-terminus is free, unlike in the fusion construct, wherein it is N-terminus of ABP that is fused to C-terminus of Fc and C-terminus of ABP is free. This reversal in the orientation of ABP did not affect its Aß-binding ability and transport across the blood brain barrier.

BBB permeability and CSF appearance of FC5 fused with human Fc (hFc) and chemically linked to ABP (FC5-hFc- ABP) in vivo (rat model). FC5-hFc was linked with ABP-cystamide using a heterobifunctional cross-linker sulfo-SMCC (sulfosuccinimidyl 4-[N-maleimidomethyl]cyclohexane-1-carboxylate) according manufacturer's instructions (ThermoFisher Scientific). Chemically conjugated molecule was administered intravenously into rats via tail vein at 6.25 mg/kg and serum and CSF samples were collected at 4 and 24 hrs and analyzed as described in FIG. 5. FC5-hFc-ABP appears in the CSF in a time-dependent manner, however Fc-ABP without the BBB carrier does not, confirming FC5-mediated transport of ABP across the blood brain barrier, and as illustrated in FIG. 7.

Example 8: Delivery of BBB-Fc-L-ABP Construct to the Brain

The ability of the FC5-Fc-ABP constructs of Example 2 to transmigrate the blood brain barrier and penetrate the brain parenchyma in vivo was assessed in mice.

Figure 8A:
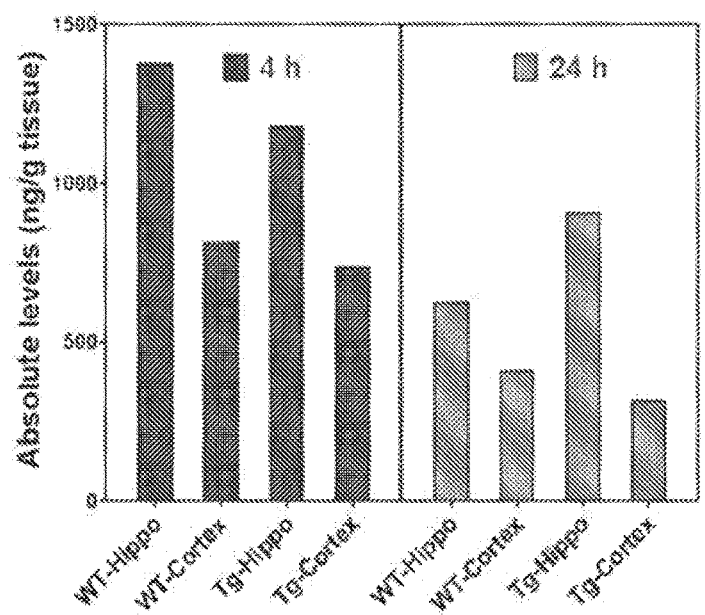
FIG. 8: shows levels of FC5-mFc-ABP measured in various brain regions (cortex and hippocampus) after intravenous injection in mice. 15 mg/kg dose of FC5-mFc-ABP was injected intravenously into the tail vein of either wild type (WT) or AD-transgenic (AD-Tg, B6.Cg-Tg, Jackson Lab) mice and brains were collected at 4 and 24 hrs after intra-cardiac saline perfusion. Hippocampal and cortical tissues were dissected and analyzed by nanoLC-MRM (FIG. 8A) and by Western blot using Fc-specific antibodies (FIG. 8B). Specific peptides belonging to all the three components of the fusion molecule (BBB, in this example FC5, Fc and ABP) were detected by MRM in both cortex and hippocampus, indicating that FC5 carrier successfully delivered ABP to the target areas of the brain. Measured levels ranged between 750-1400 ng/g brain tissue at different time points, compared to ~50 ng/g tissue typically measured for control single-domain antibody A20.1 fused to Fc, or Fc fragment alone. This was further confirmed by Western blot analysis probing for Fc and ABP in tissue extracts (FIG. 8B). No protein signal of the fusion molecule was detected in animals receiving just saline by Western blot. There was a dose-dependent increase in FC5-mFc-ABP levels detected by Western blot in the target regions of the brain.
Figure 8B:
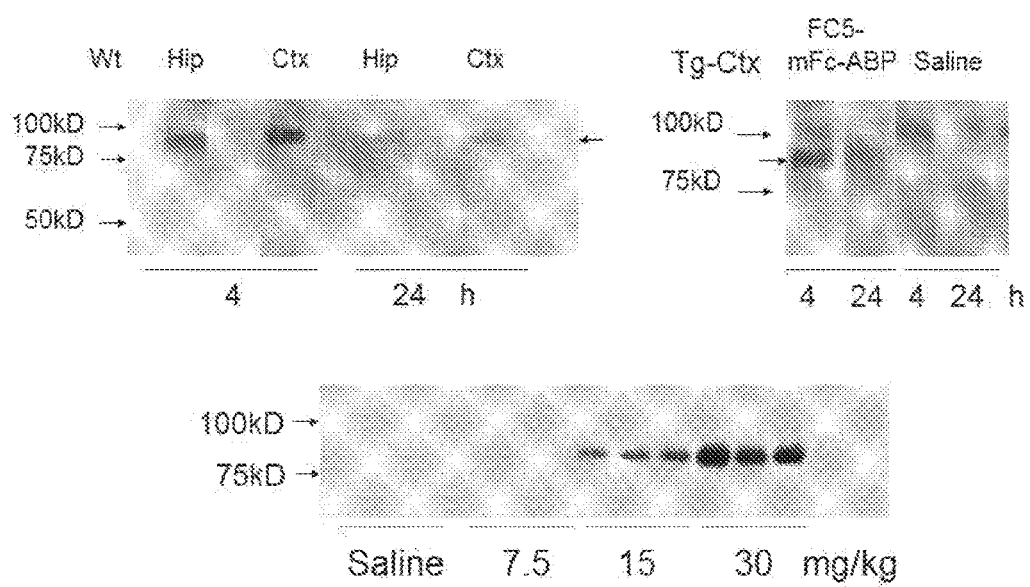

FC5-mFc-L-ABP was administered by intravenous injection via tail vein at either 15 mg/kg to wild type (WT) and AD-transgenic (AD-Tg, B6.Cg-Tg, Jackson Lab) mice (FIGS. 8A and 8B) or at 7.5, 15 and 30 mg/kg to AD-Tg mice, and circulated for 4 and 24h. Mice were then thoroughly perfused with 10 ml of heparinized (100 U/ml) saline at a rate of 1 ml/min via the left common carotid artery to facilitate specific perfusion of the brain. Brains were then removed, and hippocampal and cortical tissues were dissected and immediately frozen and stored at −80° C. until use. Frozen tissue was homogenized in ice-cold homogenization buffer containing 50 mM Tris-HCl pH 8, 150 mM NaCl and protease inhibitor cocktail (Sigma-Aldrich, Oakville, ON) using Dounce homogenizer (10-12 stroke at 4° C.). Samples were then sonicated three times for 10 s each at 4° C. and insoluble material was removed (10,000×g for 10 min at 4° C.). The supernatant was analyzed for protein content, and about 0.5 µg of protein was used for SRM analysis (FIG. 8A) using methods described in Example 4 and peptide signatures shown in Table 1. Samples were also analysed by Western blot using mFc-specific antibodies (FIGS. 8B and 8C). Specific "signature" peptides belonging to all the three components of the fusion molecule (FC5, Fc and ABP) were detected by MRM in both cortex and hippocampus, indicating that FC5 carrier successfully delivered ABP to the target areas of the brain (only data from FC5 peptide is shown in FIG. 8A). Measured levels ranged between 750-1400 ng/g brain tissue at different time points, compared to ~50 ng/g tissue typically measured for control single-domain antibody A20.1 fused to Fc, or Fc fragment alone. This was further confirmed by Western blot analysis probing for Fc and ABP in tissue extracts (8B and 8C). No protein signal of the fusion molecule was detected in animals receiving just saline by Western blot. There was a dose-dependent increase in FC5-mFc-ABP levels detected by Western blot in the target regions of the brain (FIG. 8C). These results clearly indicate that FC5 successfully delivers ABP to the target regions of the brain (i.e., the hippocampus and cortex) in wild type (WT) and AD-Tg mice.

Example 9: Clearance of Aβ from Mouse Brain

To evaluate the efficacy of ABP on the amyloid burden in Tg mice, the results of treatment with ABP alone or FC5-ABP construct were compared.

Figure 9A:
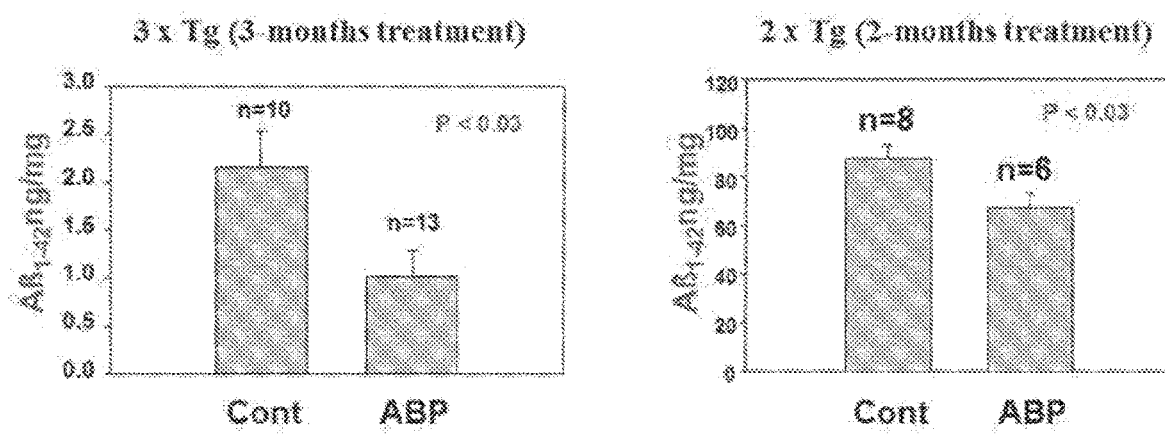
FIG. 9: shows the effect of ABP on Aß levels in transgenic (Tg) mice: Comparison between treatment with ABP alone (FIG. 9A) or ABP fused with BBB carrier FC5 (FIG. 9B and FIG. 9C). Two different AD Tg mouse models, triple transgenic (3×Tg-AD, sv129/C57BL6 mice harboring PS1M146V, $APP_{Swe}$ and tauP301L transgenes, Dr. F. M. LaFerla, University of California) and double transgenic (B6.Cg-Tg, harboring PSEN1dE9 and $APP_{Swe}$ transgenes, Jackson Lab) were used; mice were dosed subcutaneously (sc) with 300 nmol/kg of free ABP every second day over a 3-month or a 2-month period, respectively. At the end of the treatment period, Aß levels in the brain were measured by ELISA. The treatment with ABP alone resulted in 25-50% reduction in brain Aß after 2-3 months of multiple treatments (every second day) (FIG. 9A). The FC5-mFc-ABP construct was injected intravenously into double-transgenic AD mice (B6.Cg-Tg, 15 mg/kg; equivalent of 220 nmol/kg) and brain Aß levels were measured by both ELISA and nanoLC-MRM 24 h after injection. Unexpectedly, about 50% amyloid reduction was observed within 24 hr of treatment with FC5-mFc-ABP (FIG. 9B), indicating that efficient brain delivery of ABP by FC5, suitably linked to Fc, dramatically increased the efficacy of ABP in reducing brain Aß levels. CSF analysis also indicated a significant decrease in $Aß_{1-42}$ levels within 24 hrs following FC5-mFc-ABP treatment (FIG. 9C). The signature peptide or epitope of Aß detected by MRM or ELISA analyses is remote/different from the Aß epitope recognized by ABP (therefore, not interfering with its quantification by either ELISA or MRM).
Figure 9B:
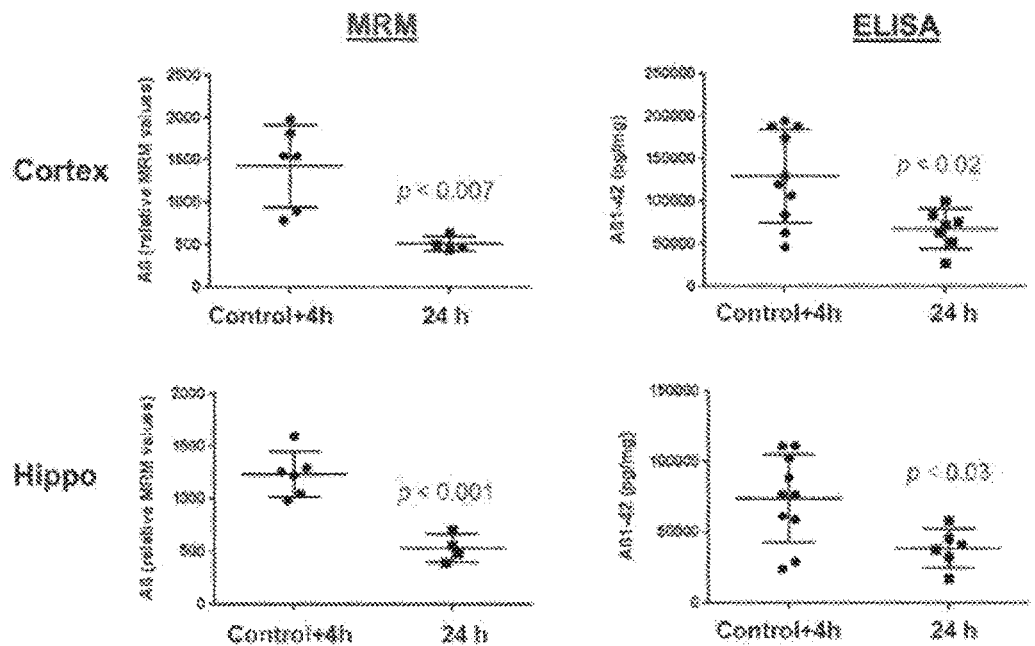
Figure 9C:
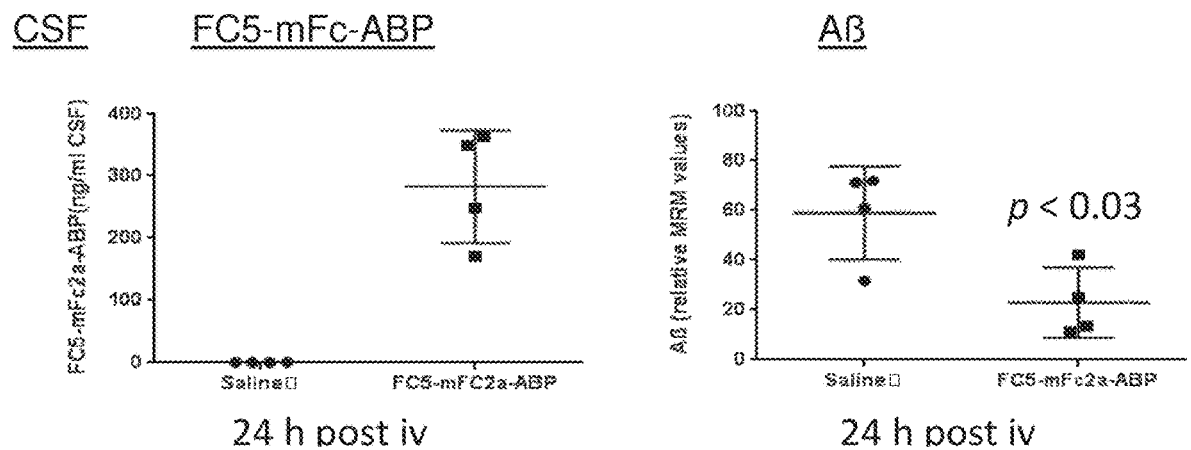

Comparison between treatment with ABP alone (FIG. 9A) or ABP fused with BBB carrier FC5 (FIGS. 9B and 9C). Two different AD Tg mouse models, triple transgenic (3×Tg-AD, sv129/C57BL6 mice harboring PS1M146V, APP$_{Swe}$ and tauP301L transgenes, Dr. F. M. LaFerla, University of California) and double transgenic (B6.Cg-Tg, harboring PSEN1dE9 and APP$_{Swe}$ transgenes, Jackson Lab) were used; mice were dosed subcutaneously (sc) with 300 nmol/kg of free ABP every second day over a 3-month or a 2-month period, respectively. At the end of the treatment period, Aβ levels in the brain were measured by ELISA using a commercial assay kit (InVitrogen, KHB3544) according to manufacturer's assay procedure. The treatment with ABP alone resulted in 25-50% reduction in brain Aβ after 2-3 months of multiple treatments (every second day) (9A). The FC5-mFc-ABP construct was injected intravenously into double-transgenic AD mice (B6.Cg-Tg, 15 mg/kg; equivalent of 220 nmol/kg) and brain Aβ levels were measured by both ELISA and nanoLC-MRM 24 h after injection as described above in Example 8. Unexpectedly, about 50% amyloid reduction was observed within 24 hr of treatment with FC5-mFc-ABP (FIG. 9B), indicating that efficient brain delivery of ABP by FC5 dramatically increased the efficacy of ABP in reducing brain Aβ levels. CSF analysis also indicated a significant decrease in Aβ$_{1-42}$ levels within 24 hrs following FC5-mFc-ABP treatment (FIG. 9C). The Aβ peptide sequence detected by MRM (SEQ: LVFFAEDVGSNK (SEQ ID NO: 64), Table 1/ELISA analyses is remote/different from the Aβ epitope recognized by ABP (therefore, not interfering with its quantification by either ELISA or MRM).

Figure 10:
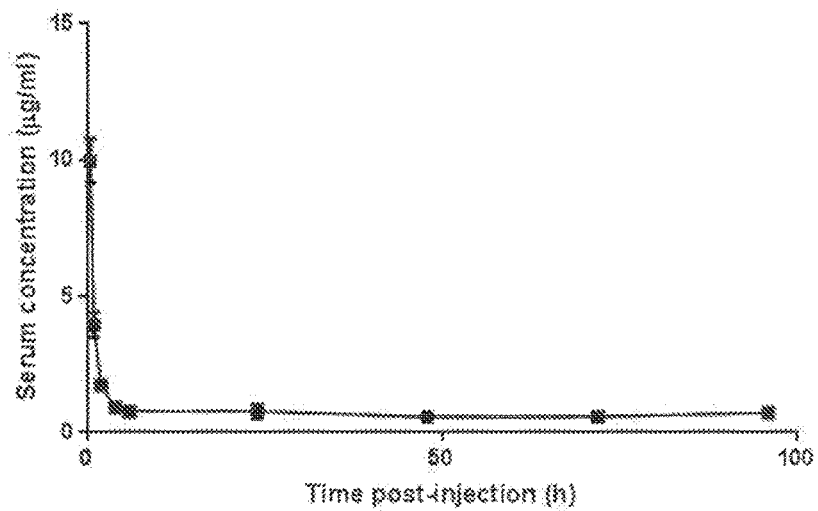
FIG. 10: shows an example of enhanced serum half-life of FC5-Fc-ABP construct compared to FC5-ABP (i.e. without Fc component): FC5-ABP and FC5-Fc-ABP were injected into rats via tail vein and serial serum samples were collected at various time points and analyzed by direct ELISA with FC5-specific antibody. As can be seen in FIG. 10 A, FC5-ABP construct was rapidly cleared in the serum (less than 1 hr) compared to FC5-Fc-ABP (FIG. 10 B), indicating substantial increase in the serum stability of the molecule comprising the Fc fragment.
Figure 10:
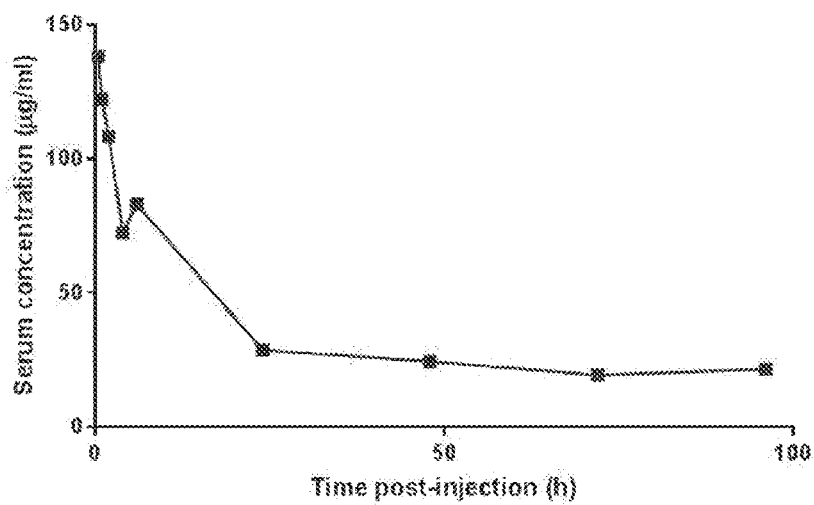

Example 10: Introduction of Fc Component into FC5-ABP Construct Enhances its Serum Half-Life FC5-ABP (FC5 SEQ ID NO 17; and ABP SEQ ID NO 36) and FC5-hFc-ABP (FC5 SEQ ID NO 17; hFc 1×7 SEQ ID NO 40 and ABP SEQ ID NO 36] constructs were produced in CHO cells as described in Example 2. Serum PK was determined as described in Example 5. FC5-ABP and FC5-Fc-ABP constructs were administered intravenously into rat tail vein at 15 mg/kg. Serum was serially collected and FC5-ABP and FC5-Fc-ABP levels were quantified by direct ELISA using FC5- and ABP-specific antibodies. Serum samples were diluted (1:5,000) in phosphate-buffered saline (PBS) and applied to Maxisorb plates and incubated overnight at 4° C. ELISA plates were washed 3×100 µl PBS and blocked with 1% BSA in TBST for 30 min at room temperature (RT). Blocking solution was removed and the plates were incubated with HRP-conjugated FC5 monoclonal antibody (90 min). Following incubation and wash, 100 µl SureBlue reagent was added and incubated in the dark at RT for 10-15 min. At the end of reaction, 100 µl 1M HCl was added and the developed colour was read at 450 nm in a plate reader. As shown in FIG. 10, FC5-ABP without Fc was very rapidly cleared in the serum (within an hr) compared to FC5-ABP construct containing Fc component (FC5-Fc-ABP). This assay was also repeated with ABP-specific antibody with similar results. After sample application, ELISA plates were incubated first with ABP rabbit polyclonal antibody (90 min), followed by HRP-conjugated rabbit secondary antibody (30 min) and the bound antibody was detected as described above (data not shown).

Example 11: Clearance of Aβ from Rat Brain

Figure 11A:
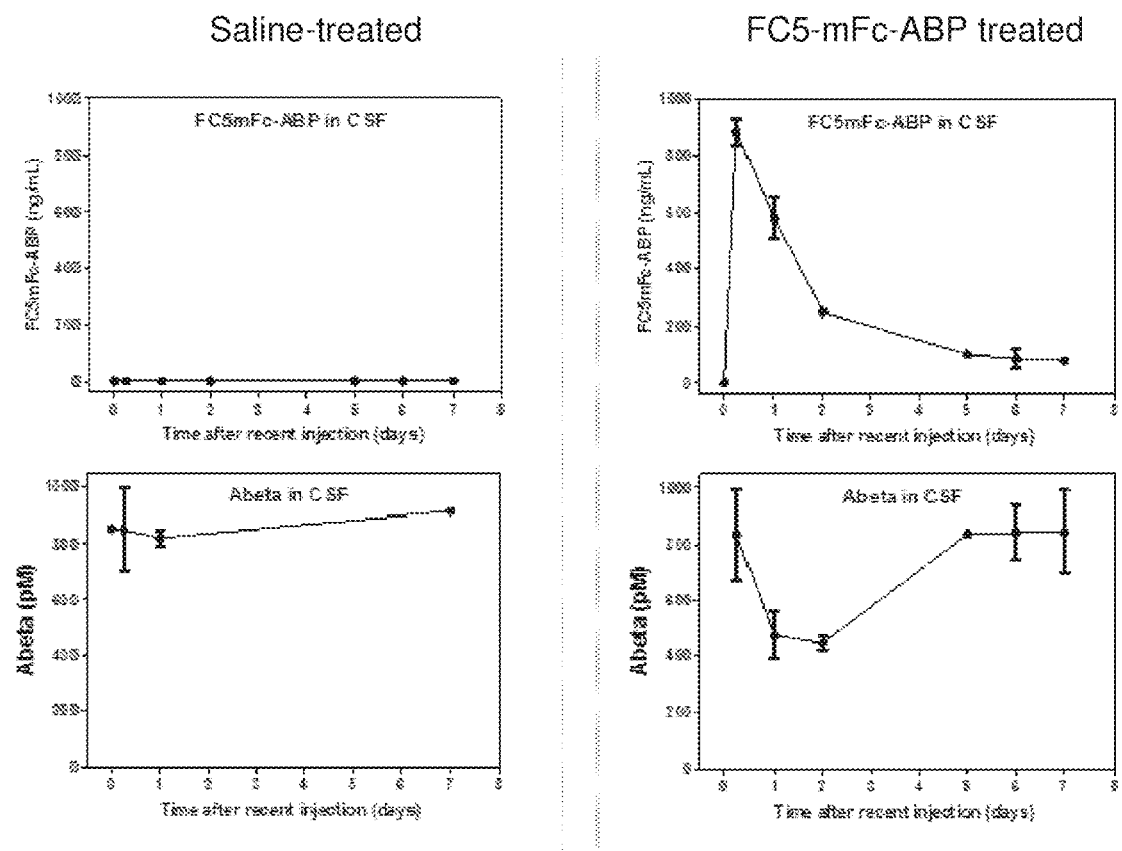
FIG. 11: shows the effect of FC5-mFc-ABP on brain amyloid burden in Tg rats: AD-Tg rats were dosed with either saline or FC5-mFc-ABP via tail vein every week over a period of four weeks (loading dose of 30 mg/kg and subsequent four weekly doses of 15 mg/kg). CSF levels of FC5-mFc-ABP and Aß were analyzed by nanoLC MRM (FIG. 11A and FIG. 11B). Before and after four weeks of treatment, brain Aß levels were determined by PET scan using a specific Aß-binding agent [18F] NAV4694. Following tracer injection, 60 min Dynamic images were acquired, transmission scans were obtained, images were reconstructed and Binding Potential ($BP_{ND}$) parametric maps were generated. FC5-mFc-ABP reduced CSF Aß level in rats within 24 hrs (FIG. 11A and FIG. 11B). An inverse relationship between the CSF levels of FC5-mFc-ABP and Aß was observed, as in Tg rats, suggesting target engagement and rapid clearance of Aß by ABP delivered to the brain and CSF by FC5 (FIG. 11B). This was further corroborated by PET scan which clearly indicated a significant reduction (30-50%) of rat brain Aß levels following four weeks of treatment with FC5-mFc-ABP (FIG. 11C).
Figure 11B:
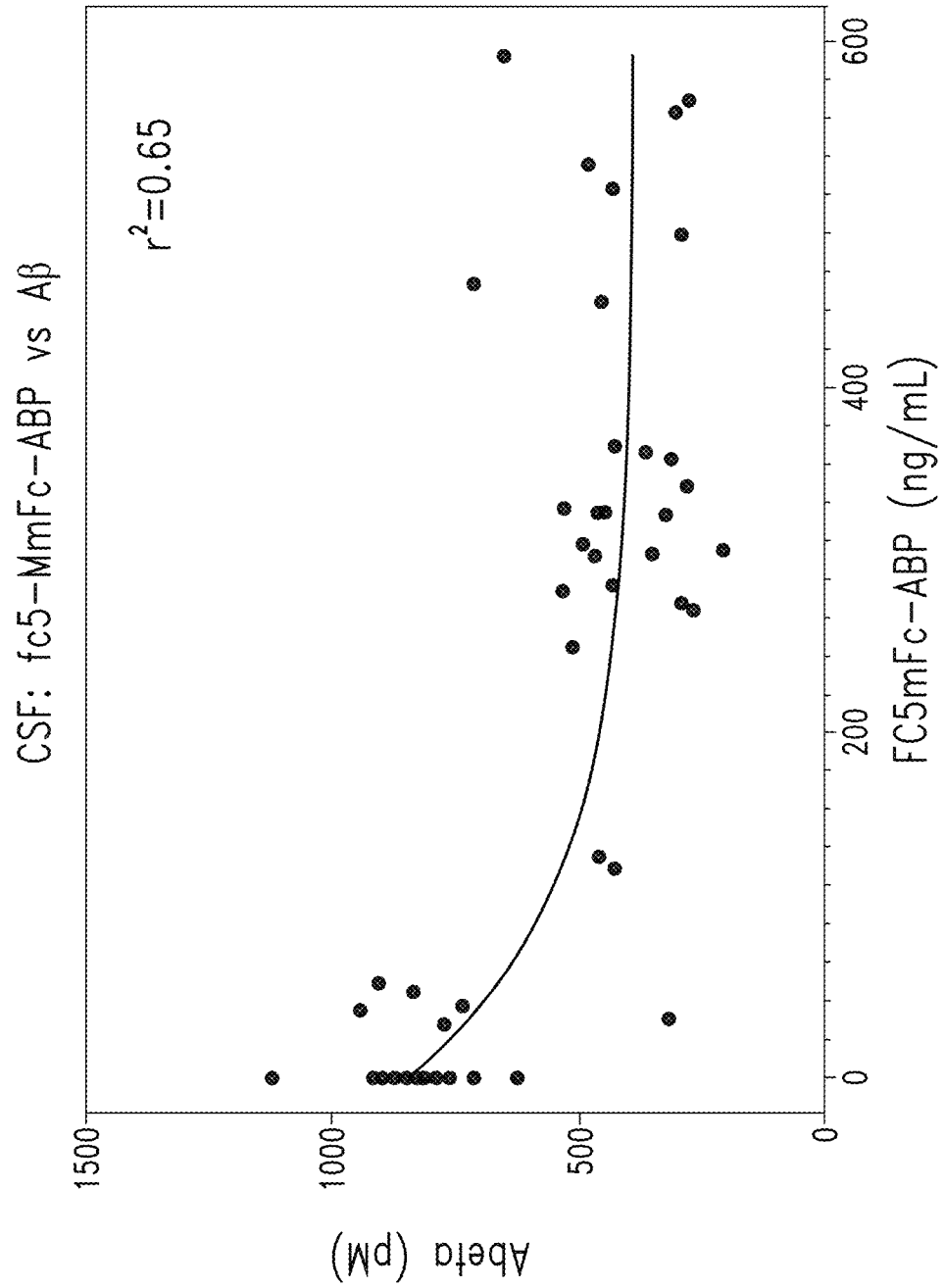
Figure 11C:
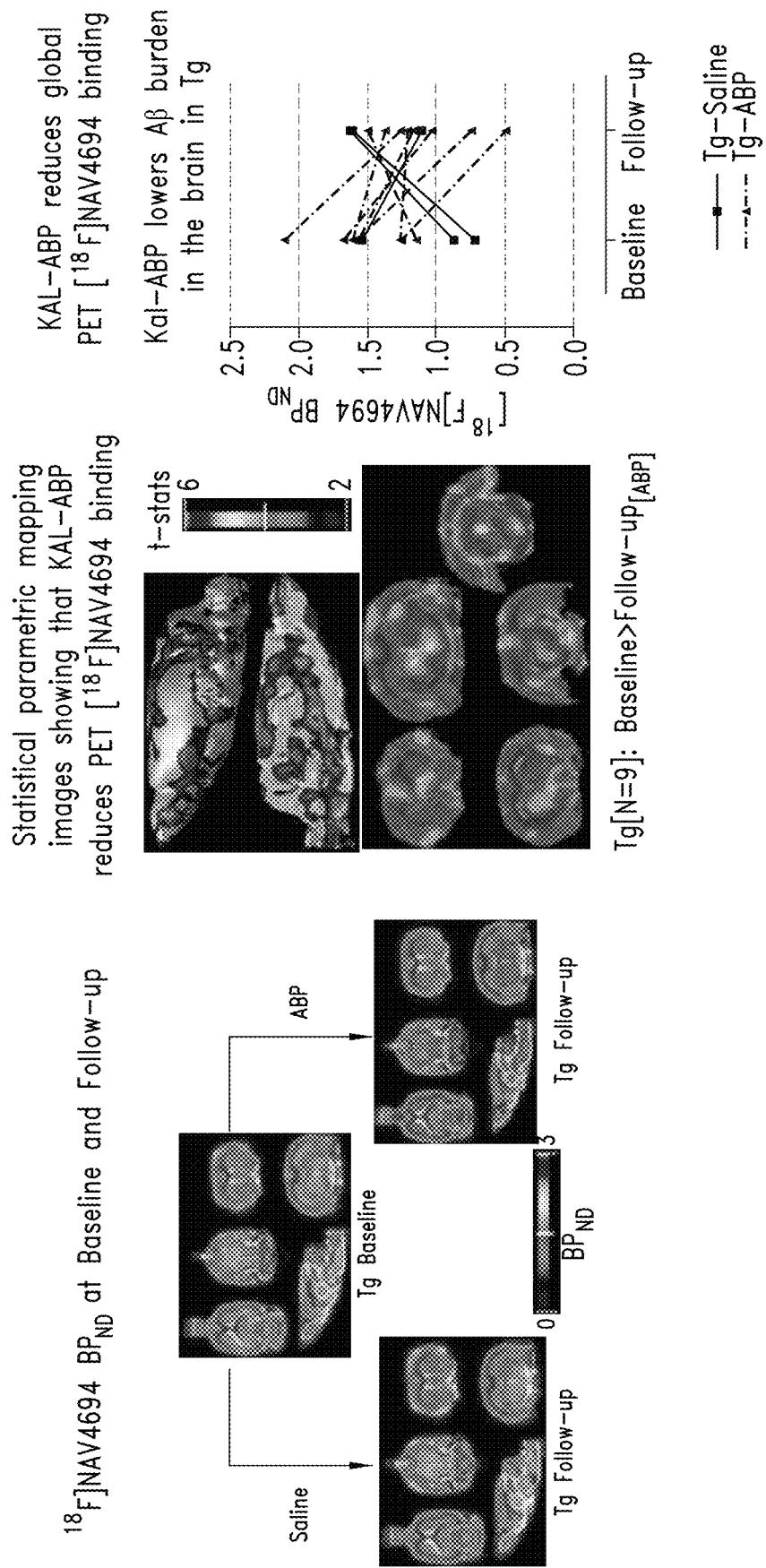

AD-Tg rats were dosed with either saline or FC5-mFc-ABP via tail vein every week over a period of four weeks (loading dose of 30 mg/kg and subsequent four weekly doses of 15 mg/kg). CSF levels of FC5-mFc-ABP and Aβ were analyzed by nanoLC MRM. Before and after four weeks of treatment, brain Aß levels were determined by PET scan using a specific Aß-binding agent [18F] NAV4694. FC5-mFc-ABP reduced CSF Aß level in rats within 24 hrs. An inverse relationship between the CSF levels of FC5-mFc-ABP and Aß was observed, as in Tg mice, suggesting target engagement and rapid clearance of Aß by ABP delivered to the brain and CSF by FC5 (FIG. 11A and FIG. 11B). This was further corroborated by PET scan which clearly indicated a significant reduction (30-50%) of rat brain Aß levels following four weeks of treatment with FC5-mFc-ABP (FIG. 11C).

Example 12: Increased Hippocampal Volume and Improved Neuronal Connectivity

Figure 12A:
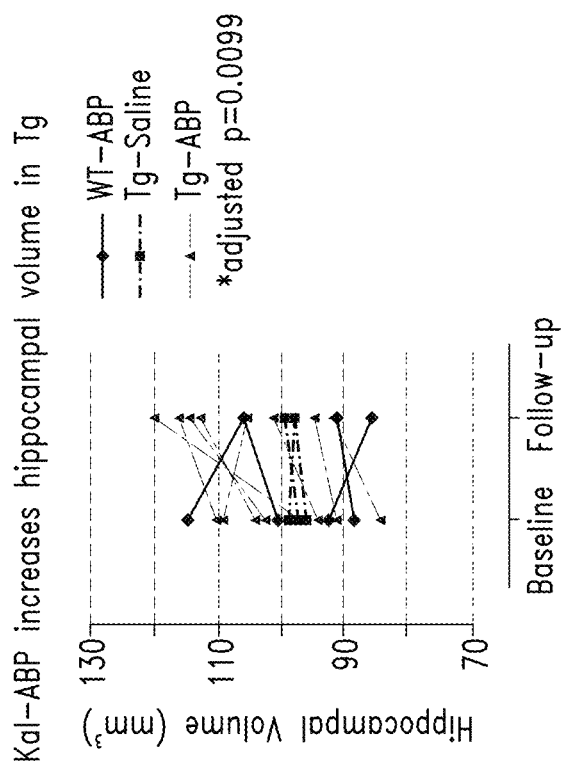
FIG. 12: shows volumetric Magnetic Resonance Imaging (MRI, using Fast Imaging with Steady-state Precession) and functional MRI (fMRI) of Tg rats before and after treatment with saline or FC5-mFc-ABP.
As shown in FIG. 12B, group comparison after four weeks of treatment showed that the ABP-treated Tg rats (Tg-ABP) had greater Anterior Cingulate Cortex (ACC) connectivity compared to saline-treated Tg rats (Tg-Sal).

In the experiment described in Example 11, saline- and FC5-mFc-ABP-treated Tg mice were subjected volumetric and functional Magnetic Resonance Imaging (MRI) before after the treatment. Volumetric MRI (FIG. 12A) showed an increased hippocampal volume in ABP-treated Tg mice compared to saline-treated controls suggesting that ABP treatment arrested hippocampal atrophy. Functional MRI (FIG. 12B) showed improved connectivity in anterior cingulated cortex in ABP-treated Tg mice compared to saline-treated controls suggesting restoration of neuronal connectivity. This data confirms the significance, efficacy and superior therapeutic advantages now provided.

Figure 13A:
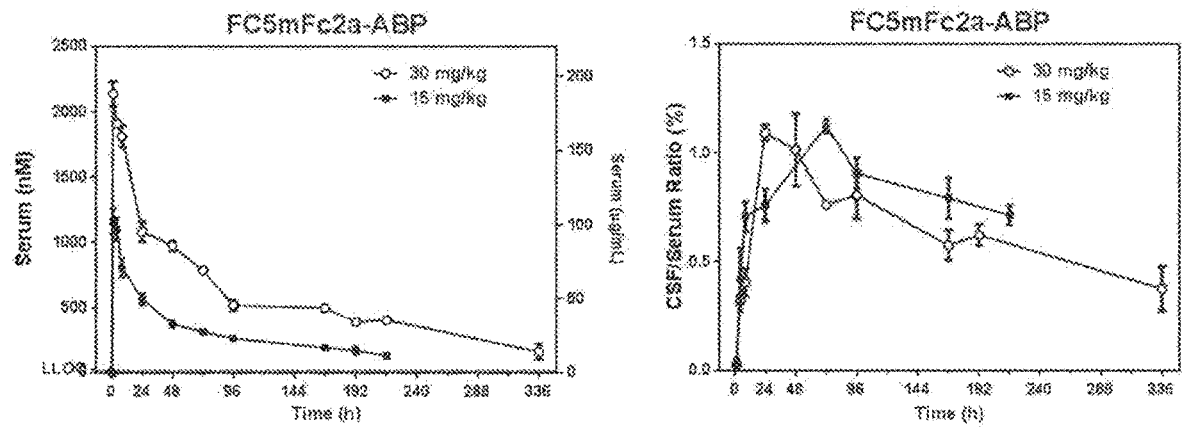
FIG. 13: shows time- and dose-dependent appearance of FC5-mFc-ABP in the CSF of beagle dog and a decrease in CSF Aß levels as seen Tg mice (FIG. 9C) and Tg rats (FIGS. 11A and B). FC5-mFc-ABP was administered by intravenous injection to 10-12-year old beagle dogs at 15 mg/kg and 30 mg/kg and serum and CSF were serially collected and analyzed by nanoLC-MRM for FC5-mFc-ABP and Aß levels. As can be seen, FC5-mFc-ABP appeared in the CSF in a time- and dose-dependent manner. Importantly, as seen in Tg mice and Tg rats, there was a significant decrease in CSF Aß levels within 24 hrs after the FC5-mFc2a-ABP injection, suggesting translational nature of FC5 carrier in larger animals and also cross-species efficacy of ABP in reducing CNS Aß burden.
Figure 13:
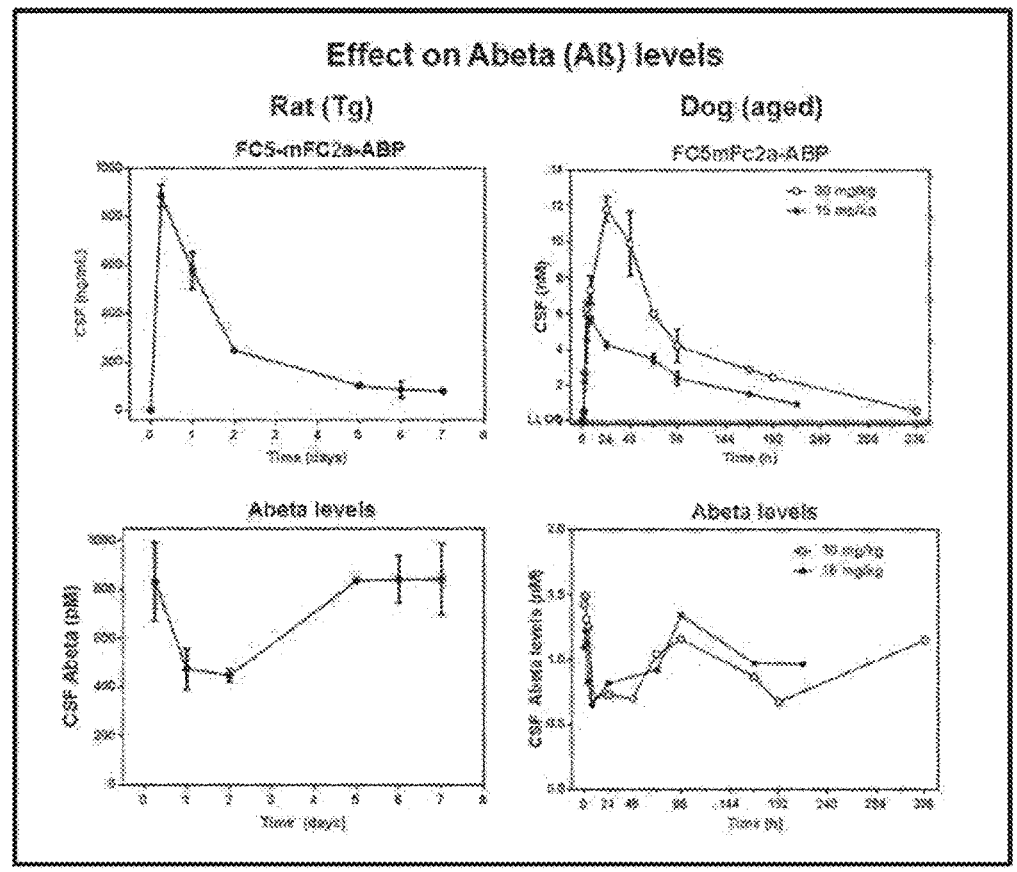

Example 13: FC5-mFc2a-ABP Treatment Shows Decreased Levels of CSF Aß in Dogs As described in Example 6, serum and CSF PK profile of FC5-mFc-ABP was assessed in beagle dog with two dose (15 mg/kg and 30 mg/kg. In addition to measuring serum and CSF levels of FC5-mFc2a-ABP by nanoLC-MRM, CSF levels of Aß was also measured by nanoLC-MRM as described in Example 9. As can be seen, FC5-mFc-ABP appeared in the CSF in a dose- and time-dependent manner (FIG. 13B). Most importantly, as seen Tg mice and Tg rat, there was a significant decrease in CSF Aß level that was inversely proportional to CSF FC5-mFc2a-ABP levels.

Example 14: Generation of ABP Fusion Molecule with a Different BBB Carrier

Figure 12A:
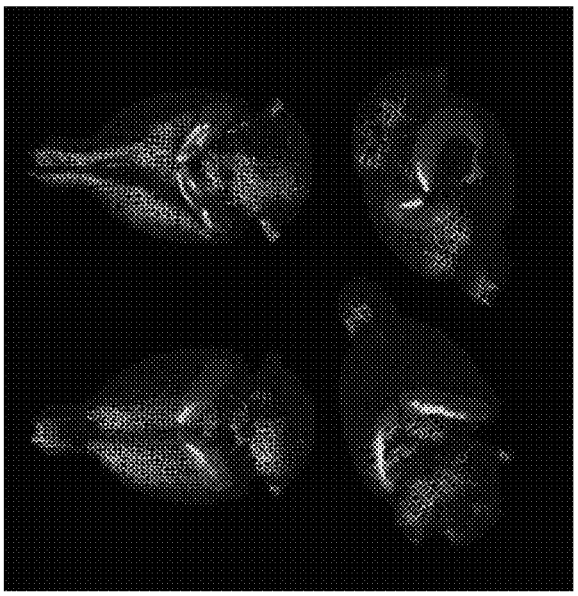
Figure 12B:
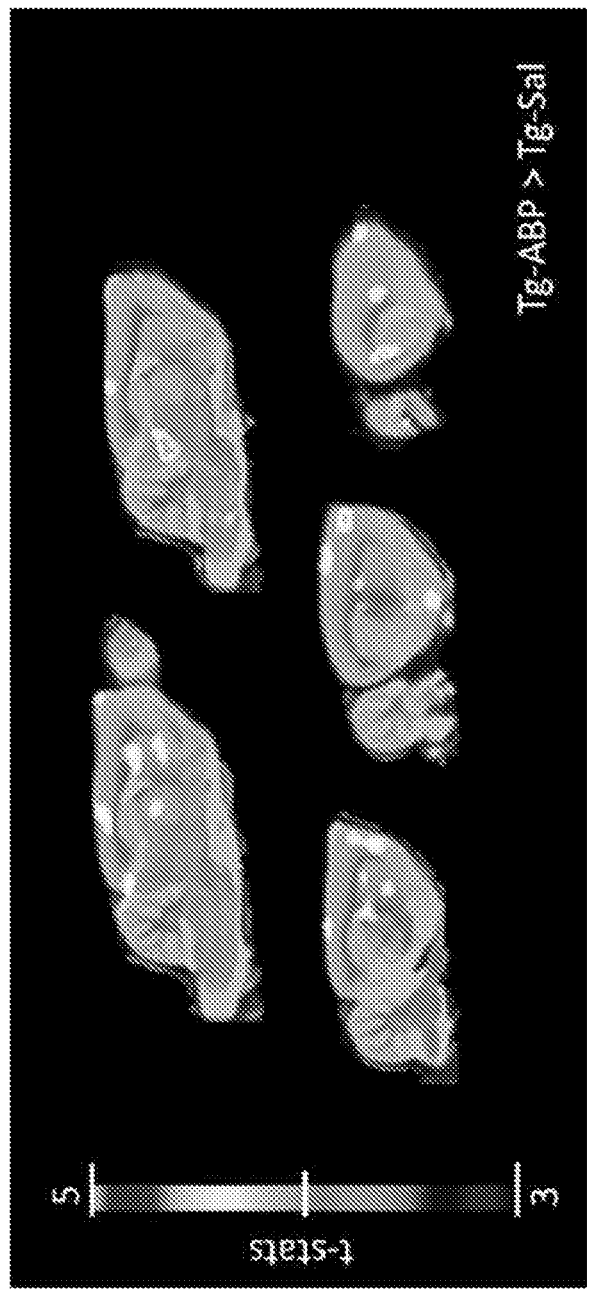

To assess the versatility of ABP fusion molecule, ABP was successfully fused with another humanized BBB carrier IGF1R5 (H2). As shown in FIG. 12, the bi-functionality of the molecule was retained, ABP's ability to bind Aß oligomer (ELISA and overlay assays) and also IGF1R5's ability deliver ABP across BBB model in vitro (data not shown). This clearly indicates that ABP can be fused to different BBB-crossing single-domain antibodies to be delivered to the brain.

Figure 15A:
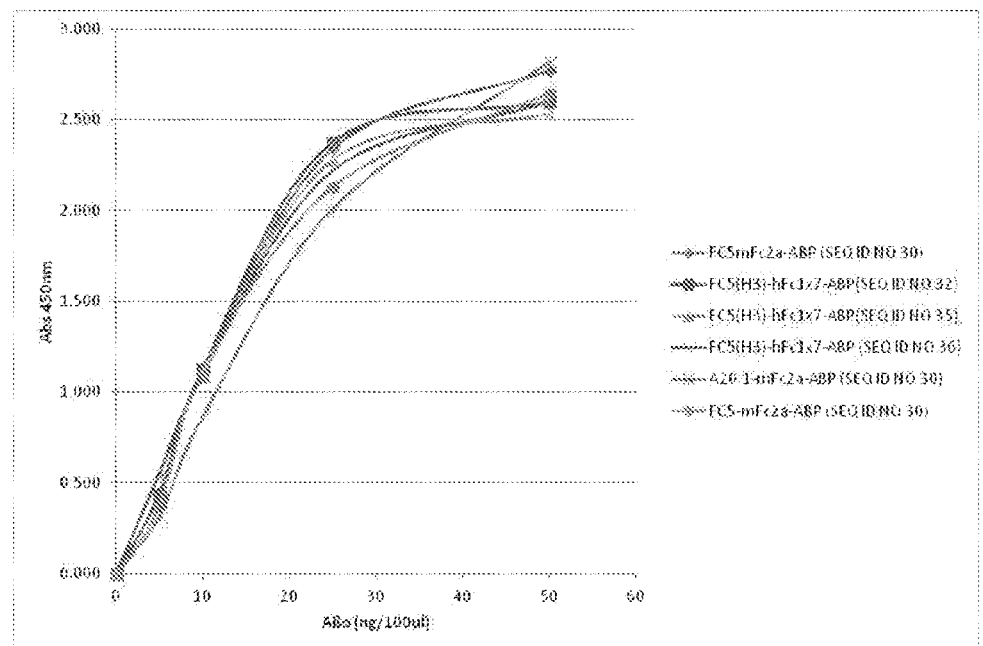
FIG. 15: shows Aß oligomer binding by different single-domain antibody-Fc-ABP constructs (FIGS. 15A, 15B and 15C). In some of these constructs, ABP has been modified by site-specific mutations or removal of C-terminus portion of the molecules as indicated in the SEQ ID NOs. All constructs retained similar potency in binding Aß oligomers by ELISA method.
Figure 15B:
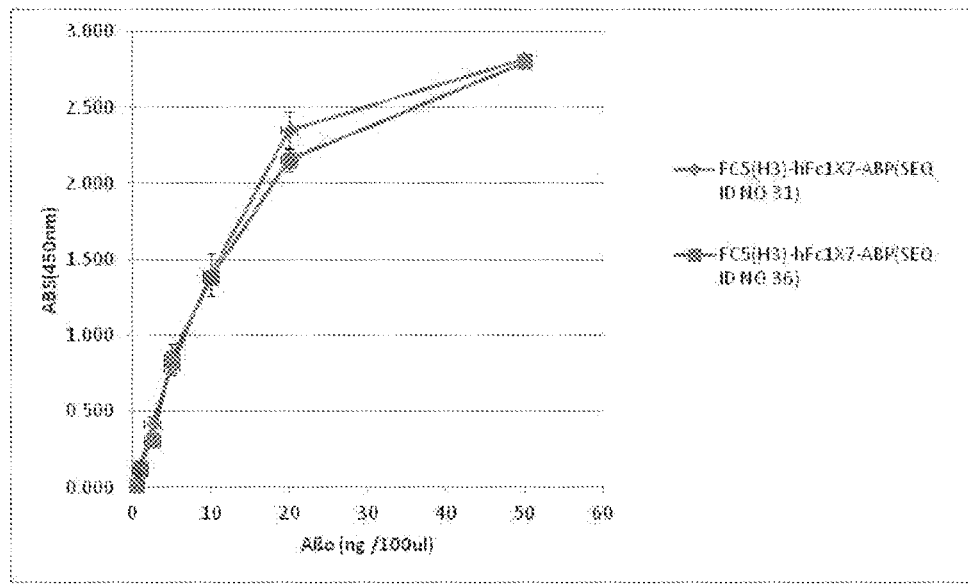
Figure 15C:
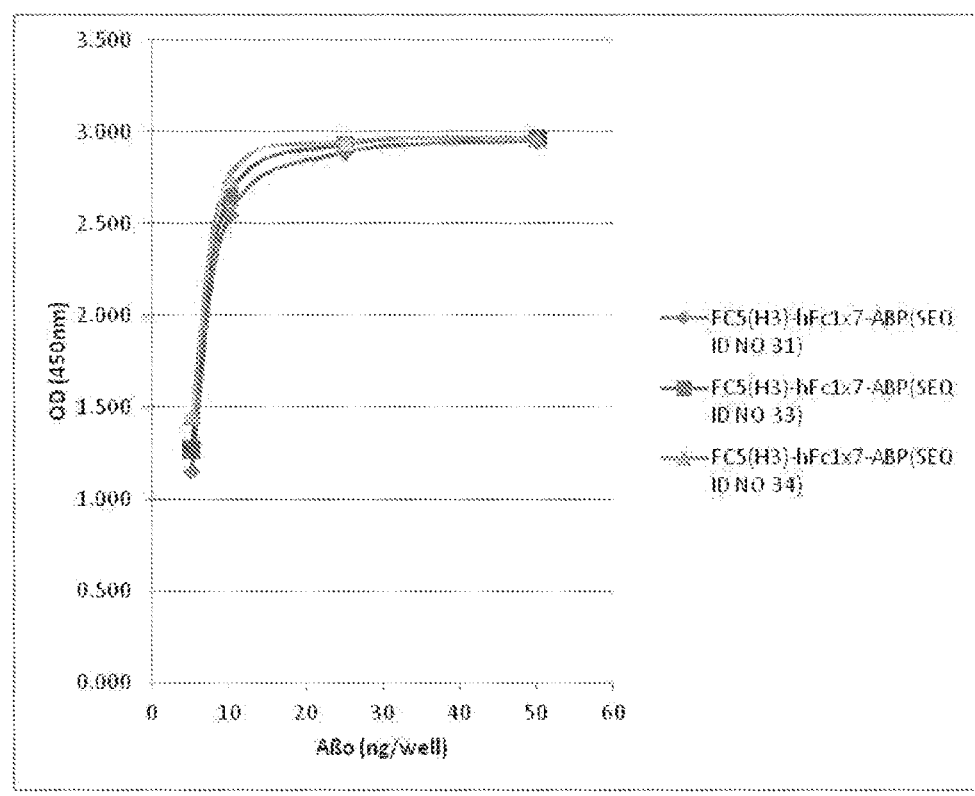
Figure 16:
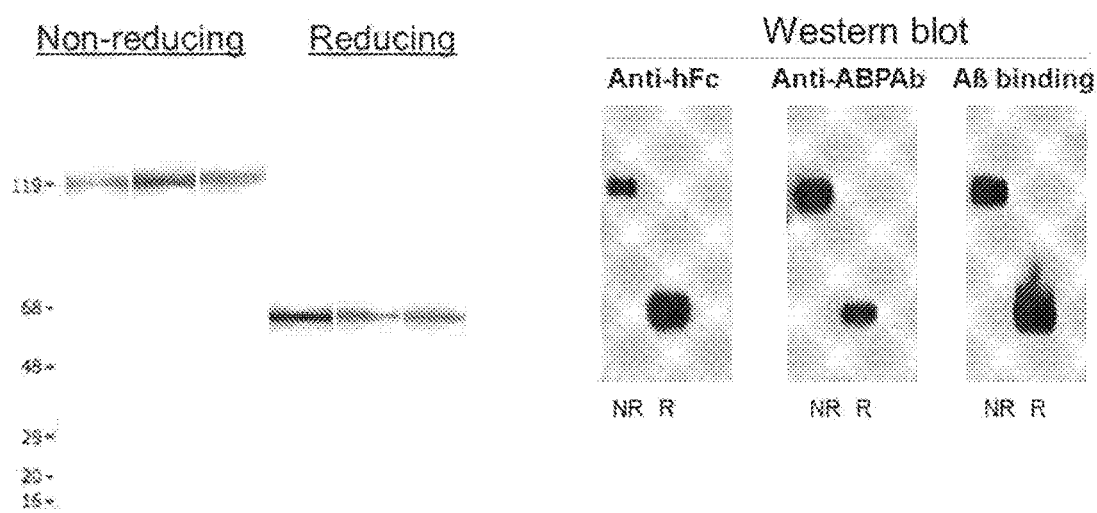
FIG. 16: shows the production of FC5-hFc1×7-ABP with specific mutations to improve stability and bio-manufacturability. FC5-hFc1×7-ABP carrying specific mutation (such as the ABP of SEQ ID NO: 35 or SEQ ID NO: 36) were produced in CHO cells and separated on SDS-PGE under reducing (R) and non-reducing (NR) conditions and stained with Coomassie blue as described in FIG. 2. Separated protein transferred to nitrocellulose membrane and immunoblotted with either FC5-specific or hFc-specific or ABP-specific antibodies. In another set, Aß-binding of ABP in the fusion molecule was also tested by overlay assay. Bound Aß was detected with Aß-specific antibody 6E10. As can be seen, the methodic modification of ABP with specific mutation substantially enhanced the stability of the molecule generated, as indicated by single protein band under reducing and non-reducing conditions.
Figure 16:
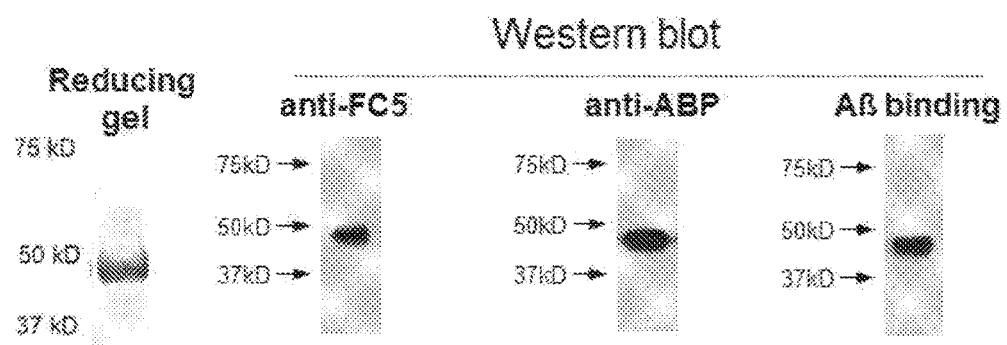

Example 15: Aß Oligomer Binding by Different BBB-Crossing Single-Domain Antibody-Fc-ABP Constructs Various FC5-Fc-ABP constructs with modified ABPs (site-specific mutations or removal of C-terminus portion of the molecule as indicated by SEQ ID Nos shown in Table1. and FIG. 15) are provided. As shown in FIG. 15, all constructs retained similar potency in binding Aß oligomers by ELISA method.

Figure 2C:
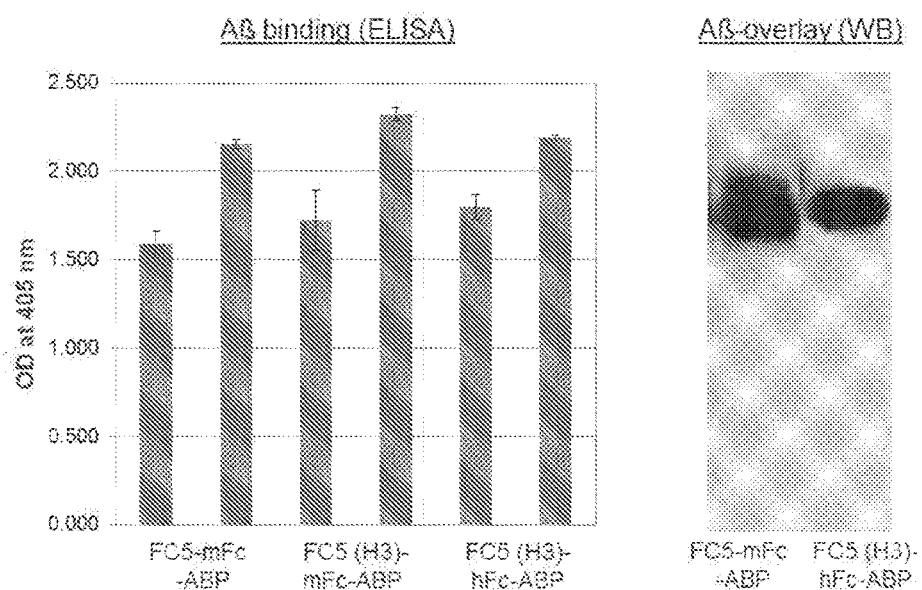

Example 16: Production of FC5-hFc1×7-L-ABP with Specific Mutations to Improve Stability and Bio-Manufacturability FC5-hFc1×7-L-ABP carrying specific mutations (ABP, SEQ ID NO 35; ABP, SEQ ID NO 36) were produced in CHO cells and separated on SDS-PGE under reducing (R) and non-reducing (NR) conditions and stained with Coomassie, blue as described in FIG. 2. Separated protein transferred to nitrocellulose membrane and immunoblotted with FC5-specific, hFc-specific and ABP-specific antibodies. In another set, Aß-binding of ABP in the fusion molecule was also tested by overlay assay. Bound Aß was detected with Aß-specific antibody 6E10. As can be seen, systematic modification of ABP with specific mutations (as shown here, for example, ABP SEQ ID NO: 35 and, ABP SEQ ID NO: 36) substantially enhanced the stability of the molecule generated, as is clearly indicated herein, for example, by a single protein band under reducing and non-reducing conditions (compare with other ABP constructs of FIG. 2A, wherein double protein bands can be seen). This substantial enhancement in the stability of the fusion molecule advantageously facilitates the bio-manufacturability of a homogeneous molecule.

Figure 17A:
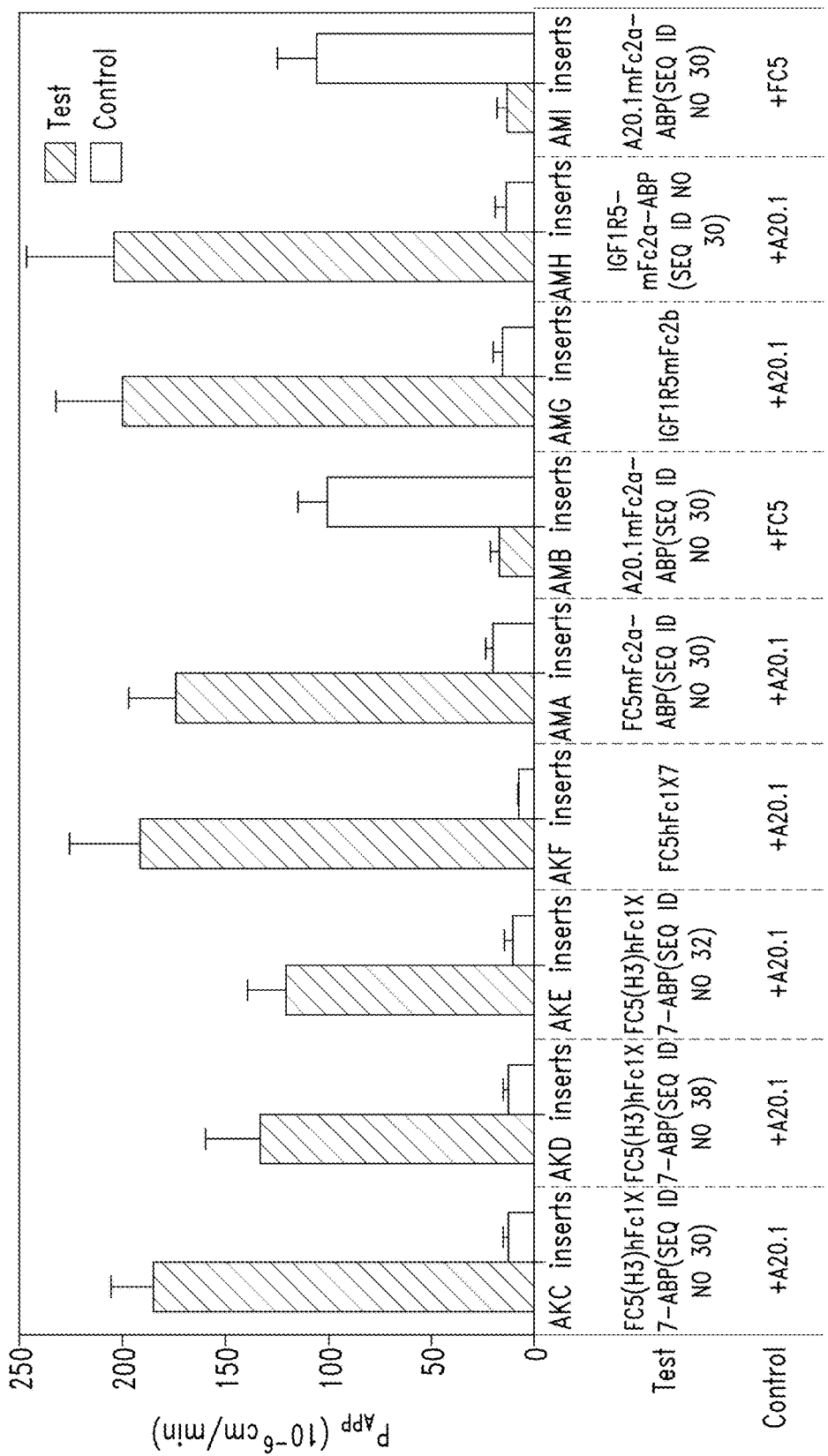
FIG. 17: shows blood brain barrier permeability of various FC5-Fc-ABP constructs and IGF1R5-Fc-ABP construct in vitro. BBB-crossing was assessed in in vitro rat BBB model as described in FIG. 4 and molecules crossing blood brain barrier were detected by nanoLC-MRM method. All ABP variants fused to humanized FC5 and IGF1R carriers crossed the blood brain barrier effectively. As expected, A20.1, a non-BBB permeable sdAb did not cross blood brain barrier, likewise ABP fused to A20.1 did not cross BBB (FIG. 17A).
In FIG. 17B, it is shown that "finger-print" peptides for all the three components of the fusion molecule, FC5, Fc and ABP were detected by nanoLC-MRM, thereby indicating the transmigration of the intact FC5, Fc and ABP across the BBB.
Figure 17B:
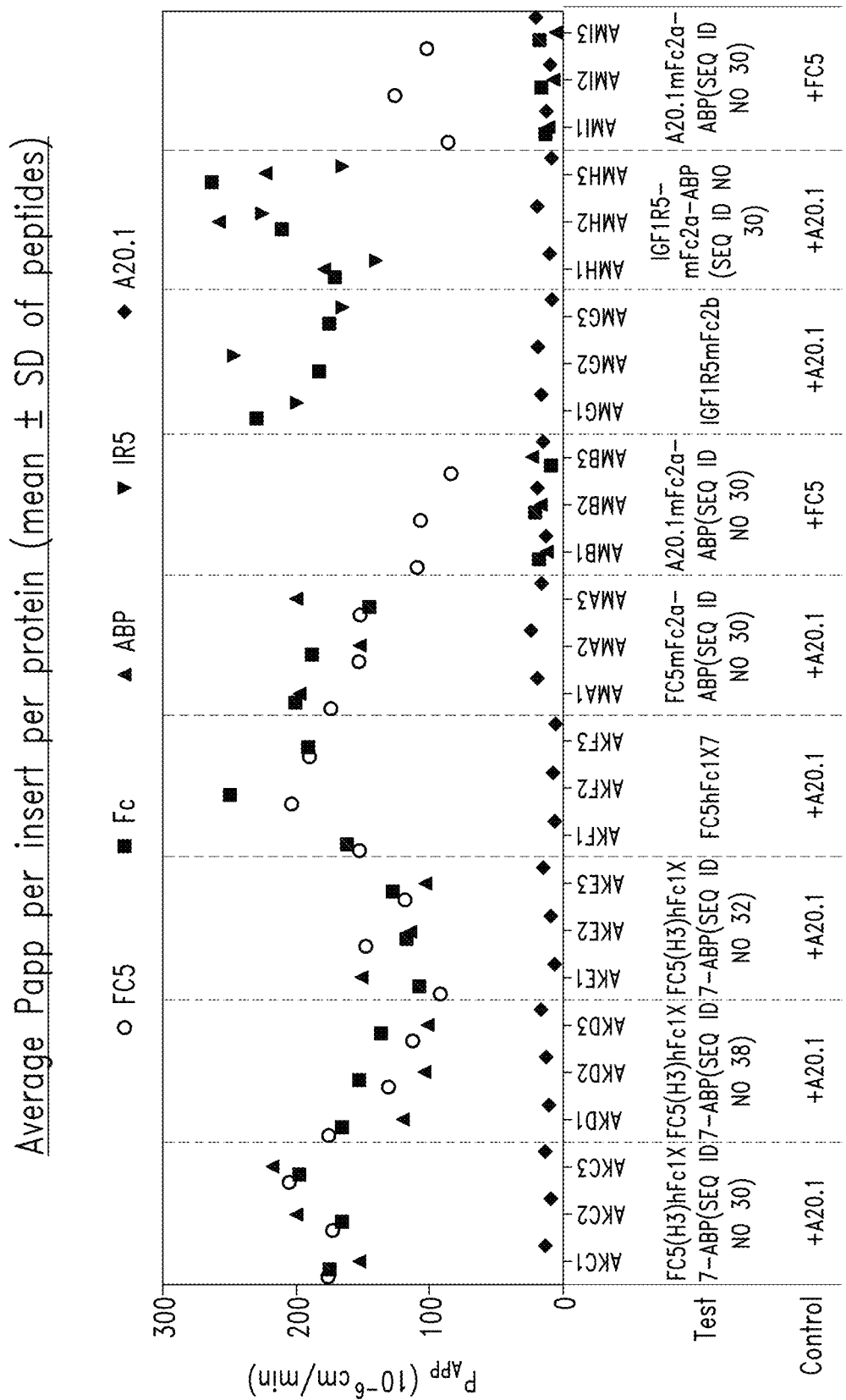

Example 17: BBB Permeability of Various FC5-Fc-L-ABP Constructs and IGF1R5-Fc-ABP Construct In Vitro BBB-crossing was assessed in in vitro rat BBB model as described in FIG. 4 and molecules crossing the blood brain barrier were detected by nanoLC-MRM method. All ABP variants fused to humanized FC5 and IGF1R carriers crossed the BBB effectively. As expected, A20.1, a non-BBB permeable sdAb did not cross BBB, and likewise, ABP fused to A20.1 did not permeate the BBB (FIG. 17A). In FIG. 17B, it is shown that "finger-print" peptides for all the three components of the fusion molecule, FC5, Fc and ABP were detected by nanoLC-MRM.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

Example 18: Humanized FC5-Fc-ABP Construct [FC5(H3)-hFc-ABP (with ABP SEQ ID NO: 35 and ABP SEQ ID NO: 36)] Crosses In Vitro Rat Blood Brain Barrier Intact Blood brain barrier-crossing of humanized FC5-ABP fusion molecules were assessed as described in Example 4. Fusion molecules crossing the blood brain barrier were analyzed by Western blot and ELISA methods. Immunoblots were probed with hFc-specific-, and ABP-specific antibodies. Both the antibodies recognized the molecule crossing the BBB (bottom chamber) and the molecular size was identical to that of FC5-ABP fusion construct that was applied to in vitro BBB (top chamber) indicating that the molecule that crossed the BBB remained intact. This was substantiated by sandwich ELISA assay where in the BBB-crossed molecule was captured with FC5-specific antibody and the captured molecule was detected with ABP antibody.

Example 19: Humanized FC5-Fc-ABP Construct (FC5(H3)-hFc-L-ABP (with ABP SEQ ID NO: 35 and ABP SEQ ID NO: 36)] is Transported Across the BBB In Vivo and Delivered to the Brain Intact by FC5

Blood brain barrier-crossing and brain delivery of humanized FC5-ABP fusion molecule in mice was assessed as described in Example 8. Four hrs following intravenous administration of the molecule and intracardiac perfusion, brain was removed and the cortices were extracted in RIPA buffer and the presence of injected FC5-ABP fusion molecule was detected by Western blot probed with ABP-specific antibody and by sandwich ELISA by capturing the molecule with FC5-specific antibody and detecting with ABP-specific antibody. Western blot revealed the presence of full-length FC5-ABP construct in the cortex. This was substantiated by sandwich ELISA which revealed the intact nature of the molecule as indicated by the ability to capture the molecule by FC5-specific antibody and detect the captured molecule with ABP-specific antibody.

Example 20: Ex-Vivo (A) and In Vivo (B) Binding of Humanized FC5-Fc-ABP Construct (FC5(H3)-hFc-ABP (ABP SEQ ID NO 361 (Target Engagement)

Immunohistochemistry was carried out as described in Example 3. Brain sections from AD-transgenic mice were incubated with FC5(H3)-hFc1×7-ABP (ABP, SEQ ID NO: 36) and the bound fusion molecule was visualized with HRP-conjugated FC5-specific antibody. As a negative control, sections were incubated with either no construct, or FC5-hFc construct without fused ABP. Briefly, Formalin-fixed 40 μm free-floating sections containing cortex and hippocampus from APP/PS1 transgenic mouse were subjected to antigen retrieval in 10 mM sodium citrate buffer (pH 9) at 80° C. for 30 minutes then cooled to room temperature. Sections were rinsed in PBS, treated with 3% $H_2O_2$ in PBS for 30 minutes to block endogenous peroxidase, then rinsed again. Following a one hour incubation in Dako serum free protein block containing 0.3% triton X-100, sections were incubated with FC5(H3)-hFc1×7-ABP or the molar equivalent of FC5-hFc1×7 in Dako diluent containing 0.3% triton X-100 for 90 minutes at room temperature. After thoroughly rinsing in PBS, the sections were incubated with anti-FC5-HRP in Dako diluent for 60 minutes at room temperature, rinsed again, and then developed using Vector Immpact DAB following the kit directions. The sections were placed on Superfrost plus slides, allowed to air dry overnight, then rehydrated, counterstained with methyl green, dipped in acetone/0.05% acetic acid (v/v) and dehydrated, cleared and coverslipped with Permount. Selective binding (black spots) was seen with FC5(H3)-hFc1×7-ABP construct but not with FC5(H3)-hFc1×7 without ABP, indicating ABP-dependent binding of Aβ deposits (target engagement) in the brain. No binding was seen in brain sections from wild type mice that does not produce amyloid deposits (data not shown).

Similar binding of Aβ deposits were detected following intra-hippocampal injection of FC5(H3)-hFc-ABP construct into AD transgenic mice (B). Four hours after intra-hippocampal injection, Tg mice were perfused and the brains were removed and sectioned. FC5(H3)-hFc-ABP binding to Aβ deposits (shiny white dots) were visualised with ABP-specific polyclonal antibody. Brain sections were first incubated with ABP-specific monoclonal antibody followed by Alexa-647 conjugated anti rabbit-Fc secondary antibody

Figure 18:
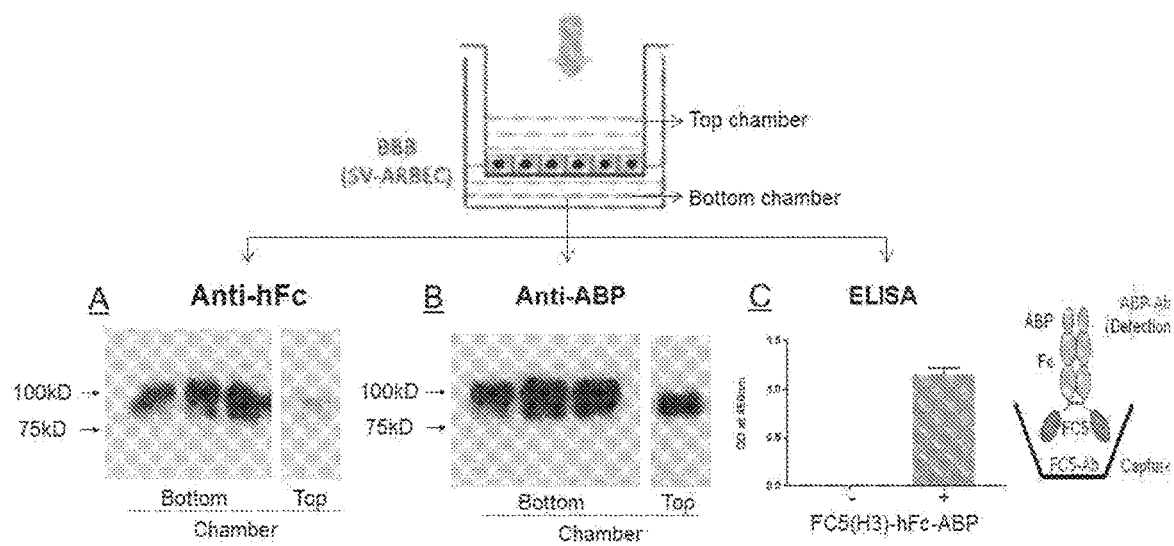
FIG. 18: shows humanized FC5(H3)-hFc1×7-ABP construct (ABP, SEQ ID NO: 35 and SEQ ID NO: 36) are transported across in vitro blood-brain barrier intact by FC5. Blood brain barrier-crossing was assessed in in vitro rat BBB model as described for FIG. 4 and molecule crossing BBB was detected by Western blot and ELISA assays.
Figure 18:
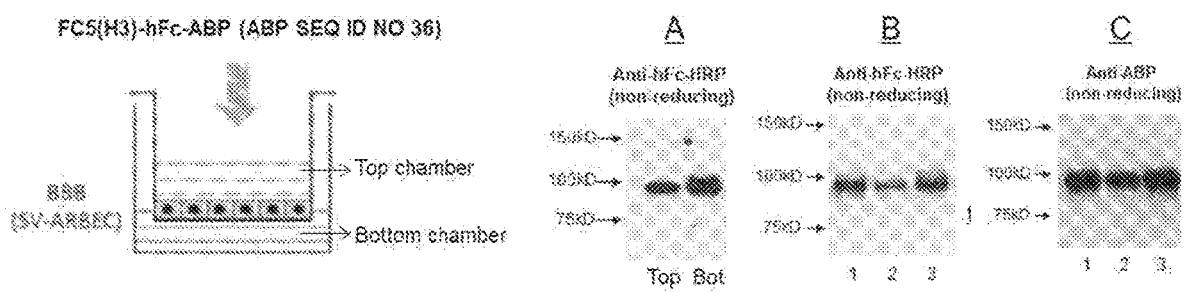
Figure 19:
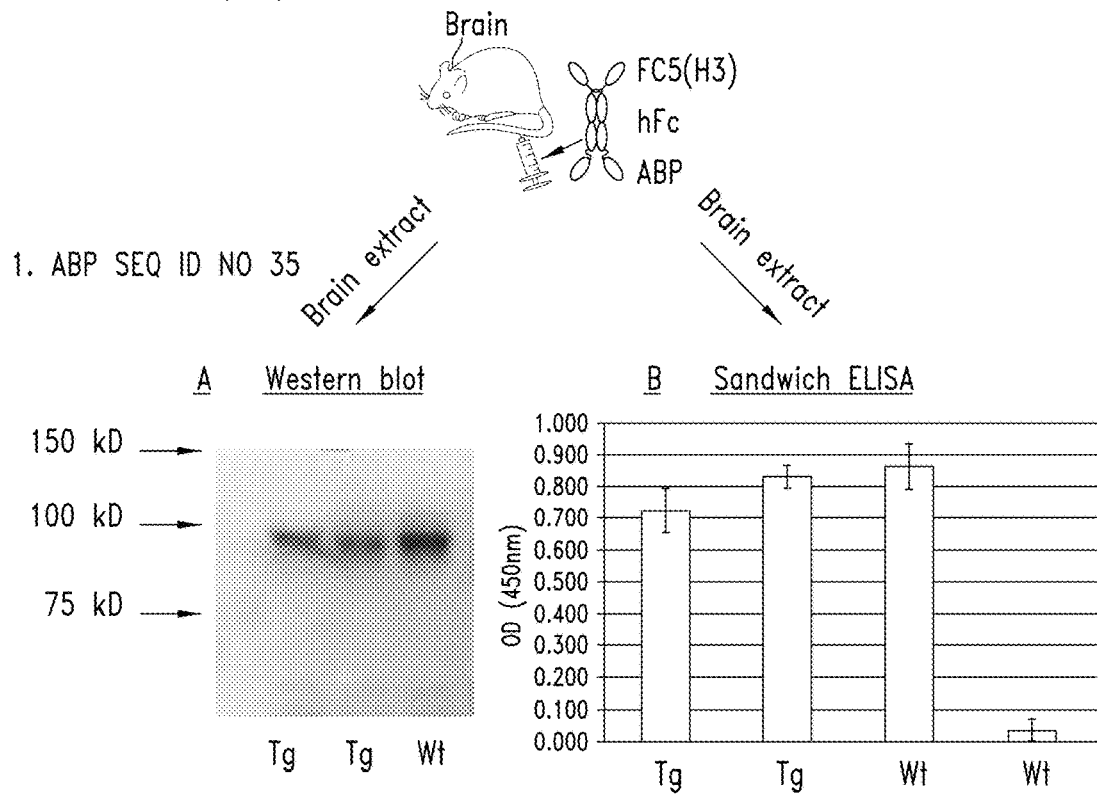
FIG. 19: shows humanized FC5(H3)-hFc1×7-ABP constructs (ABP, SEQ ID NO: 35 and SEQ ID NO: 36) are transported across in vivo blood-brain barrier and delivered to the brain intact by FC5. The FC5-ABP fusion molecule was administered intravenously into wild type and AD-Tg mice via tail vein and brains were collected following intra-cardiac perfusion as described for FIG. 8. Brain cortex was homogenized and extracted in RIPA buffer and the extract was subjected to Western blot and sandwich ELISA analysis as described for FIG. 18.
Figure 19:
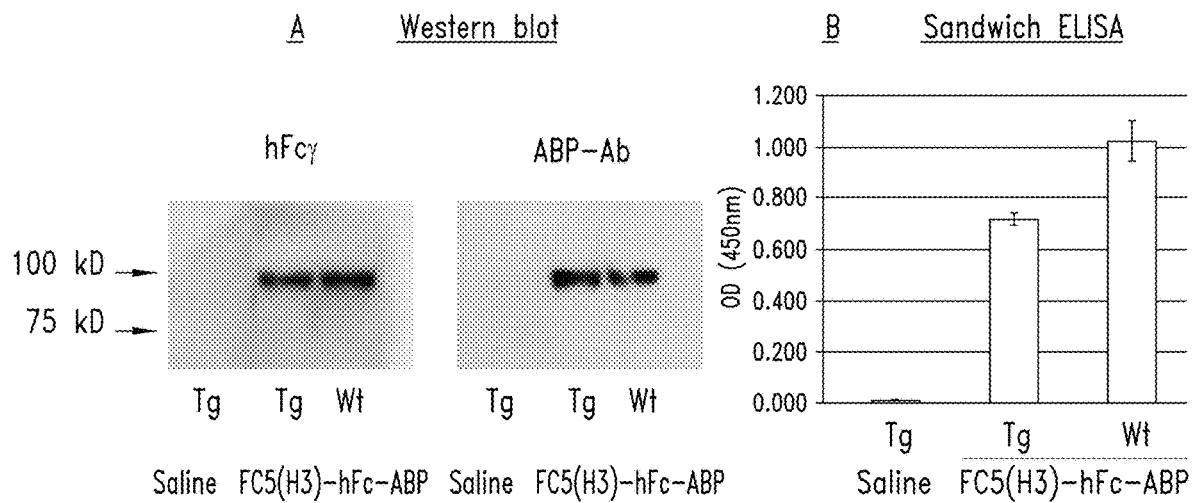
Figure 20:
FIG. 20: shows immunohistochemical analysis of ex-vivo binding (A) and in vivo binding (B) of FC5(H3)-hFc1×7-ABP (ABP, SEQ ID NO: 36) to endogenous Aß deposits in AD-Tg mouse brain (B6.Cg-Tg, Jackson Lab). Brain sections from AD-transgenic mice were incubated with FC5 (H3)-hFc1×7-ABP (ABP, SEQ ID NO: 36) and the bound fusion molecule was visualized with HRP-conjugated FC5-specific antibody. Selective binding (black spots) was seen with FC5(H3)-hFc1×7-ABP construct but not with FC5 (H3)-hFc1×7 without ABP (A), indicating ABP-dependent binding of Aß deposits (target engagement) in the brain. No binding was seen in brain sections from wild type mice that does not produce amyloid deposits (data not shown). Similar binding of Aß deposits were detected (using ABP-specific antibody) following intra-hippocampal injection (4 hrs post-injection) of FC5(H3)-hFc-ABP construct into AD transgenic mice (B).
Figure 20:
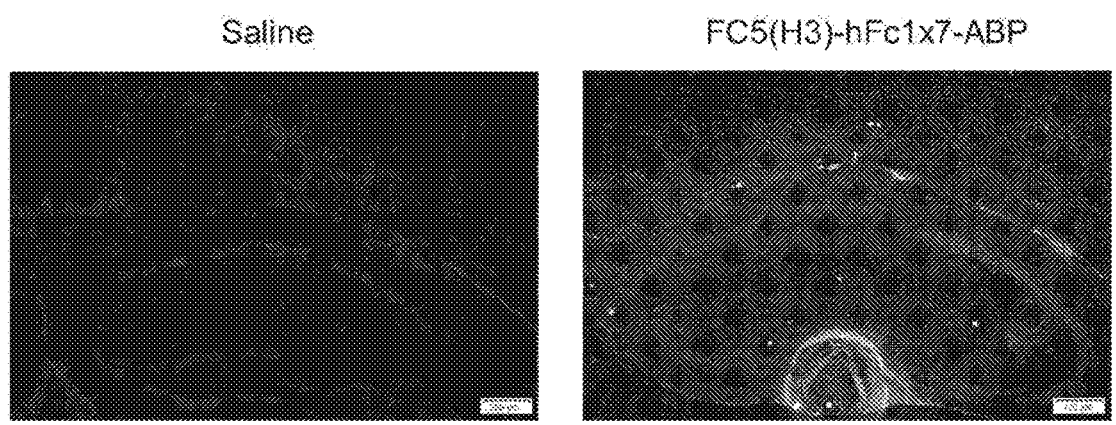
Figure 21:
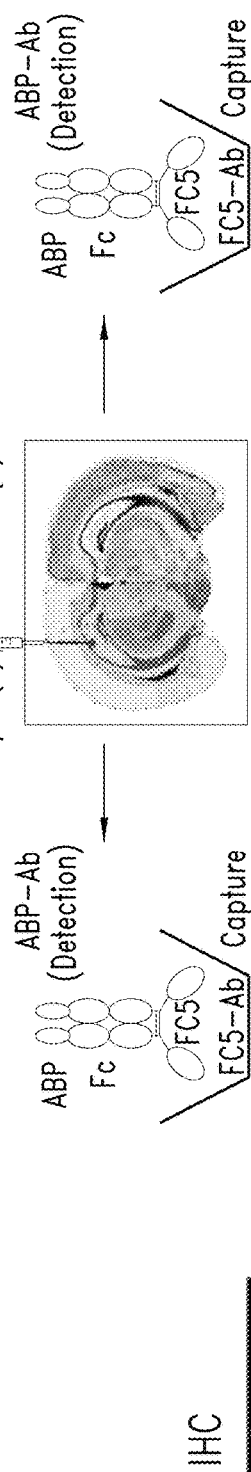
FIG. 21: shows target engagement by FC5(H3)-hFc1×7-ABP (ABP, SEQ ID NO: 32) in vivo.
Figure 21:
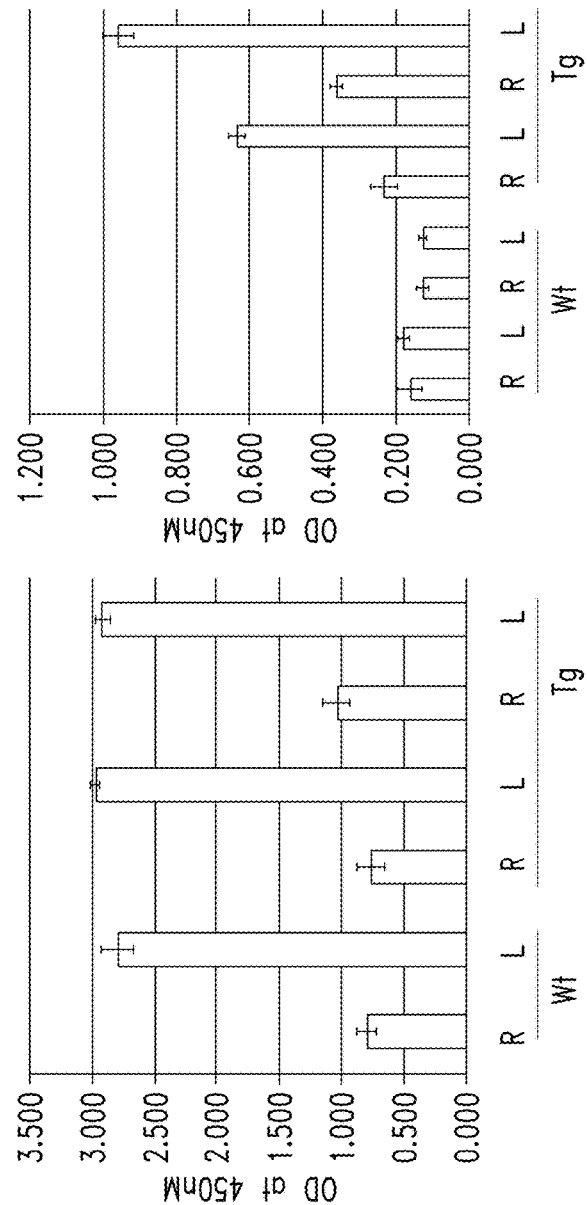
Figure 21:
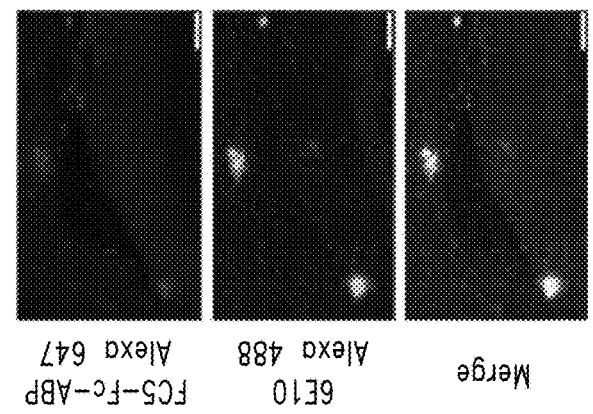

Example 21: Target Engagement by Humanized FC5-Fc-ABP Construct (FC5(H3)-hFc-ABP (SEQ ID NO: 46) In Vivo Fluorophore-labelled (FIG. 18A) or naïve FC5-ABP (FIG. 18B) fusion molecule was microinjected into the hippocampal region of wild-type (Wt) and AD-Tg (Tg) mice. 30 min after microinjection of fluorophore-labelled FC5-ABP fusion molecule, brains were removed, sectioned and observed under fluorescence microscope. As shown in 21A, injected molecule bound to Aβ deposits as confirmed by its co-localization with Aβ-specific antibody. In a parallel study, four hrs after intra-hippocampal injection of naïve FC5-ABP fusion molecule, hippocampal formation from injected (ips) and non-injected (con) regions were collected and homogenized in Tris-buffered saline. Hippocampal extracts were subjected to sandwich ELISA with FC5 antibody as capturing antibody and either ABP or Aβ-specific antibody as detection antibody. As shown in 21B, microinjected FC5-ABP molecule remained intact and ABP was able to engage and bind the target Aβ in vivo as indicated by the presence of Aβ in the pulled-down complex detected by Aβ-specific antibody.

Figure 22A:
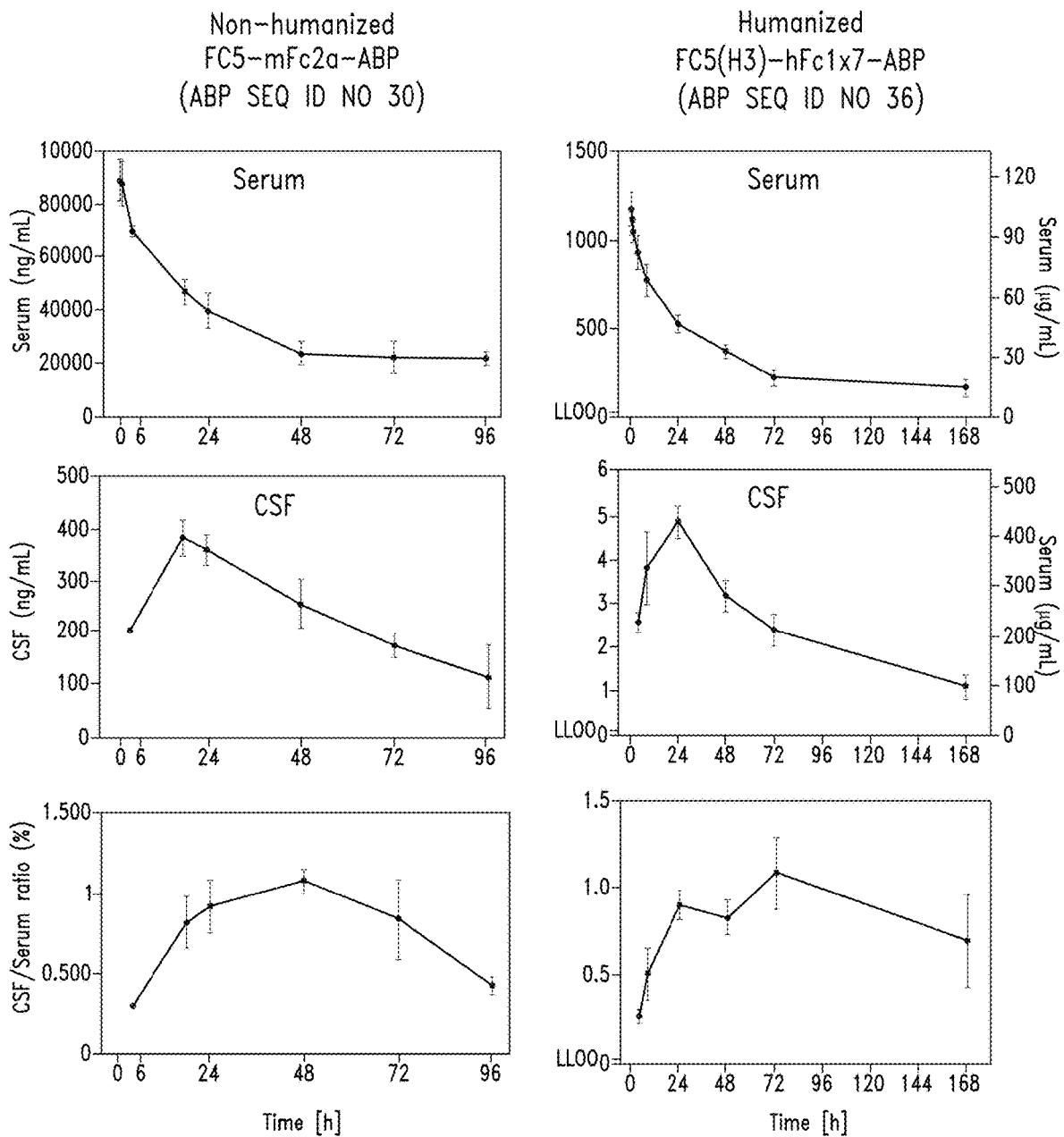
FIG. 22: shows PK, PD comparison between non-humanized and humanized FC5-Fc-ABP constructs. FC5-mFc2a-ABP or FC5(H3)-hFc1×7-ABP was administered intravenously into rats via tail vein injection at 15 mg/kg as described for FIG. 5. Serum and CSF were serially collected. FC5-Fc-ABP levels were quantified using nanoLC-MRM method.
Figure 22:
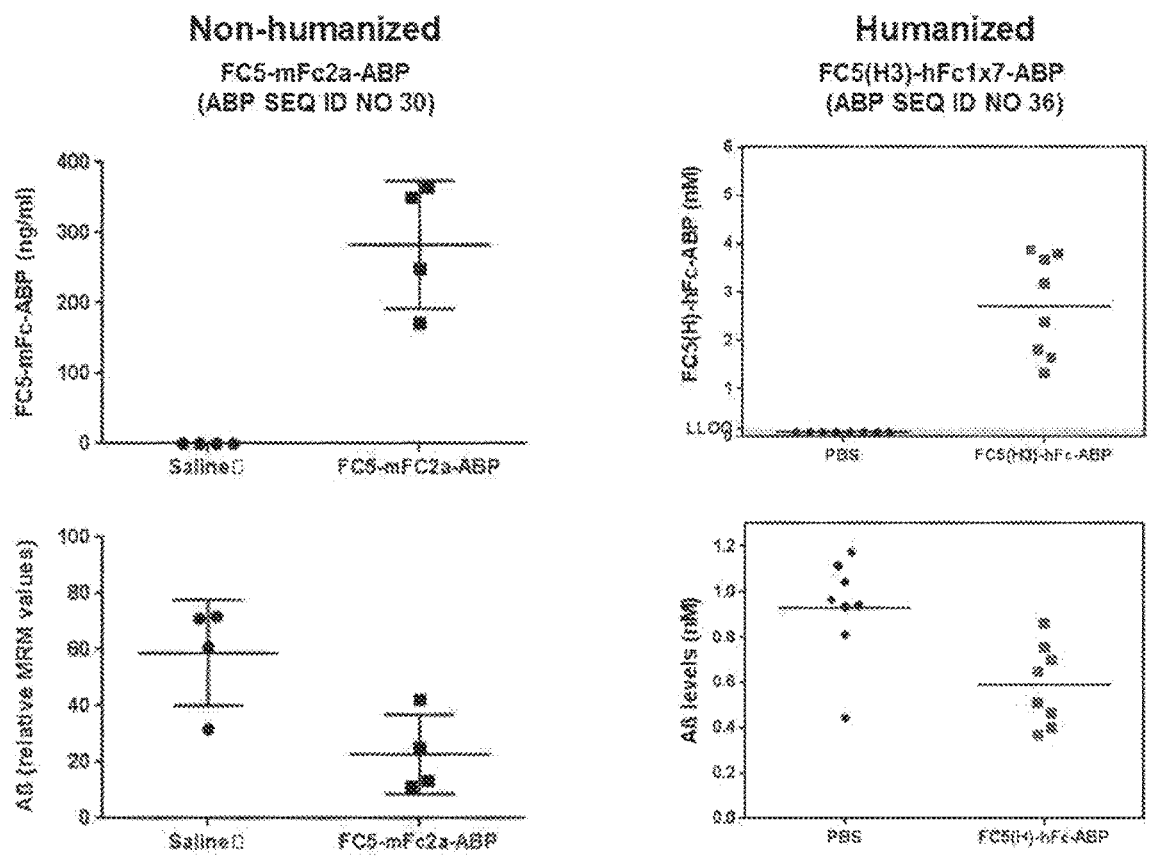

Example 22: PK/PD Comparison Between Non-Humanized and Humanized FC5-Fc-L-ABP Constructs FC5-mFc2a-ABP or FC5(H3)-hFc1×7-ABP was administered intravenously into rats via tail vein injection at 15 mg/kg as described for FIG. 5. Serum and CSF were serially collected. FC5-Fc-ABP levels were quantified using nanoLC-MRM method. As shown in FIG. 22 A, serum and CSF PK profile were very similar for non-humanized and humanized constructs. FC5-mFc2a-ABP or FC5(H3)-hFc1× 7-ABP was administered intravenously into Tg mice via tail vein injection at 15 mg/kg as described for FIG. 9B. FC5-Fc-ABP and Aβ levels in the CSF were measured by nanoLC-MRM as described in FIG. 9B. As shown in FIG. 22 B, the levels of non-humanized and humanized FC5-Fc-ABP in the CSF were similar, and most importantly, changes (decrease) in CSF Aβ levels were also very similar, indicating that humanization of FC5-Fc-ABP construct did not affect the PK and PD profile of the fusion construct.

Sequences

| SEQ ID NO: | Sequence | Description |
|---|---|---|
| 1 | GFKITHYTMG | CDR1 FC5 |
| 2 | RITWGGDNTFYSNSVKG | CDR2 FC5 |
| 3 | GSTSTATPLRVDY | CDR3 FC5 |
| 4 | EYPSNFYA | CDR1 IGF1R-3 |
| 5 | VSRDGLTT | CDR2 IGF1R-3 |
| 6 | AIVITGVWNKVDVNSRSYHY | CDR3 IGF1R-3 |
| 7 | GGTVSPTA | CDR1 IGF1R-4 |
| 8 | ITWSRGTT | CDR2 IGF1R-4 |
| 9 | AASTFLRILPEESAYTY | CDR3 IGF1R-4 |
| 10 | GRTIDNYA | CDR1 IGF1R-5 |
| 11 | IDWGDGGX; where X is A or T | CDR2 IGF1R-5 |
| 12 | AMARQSRVNLDVARYDY | CDR3 IGF1R-5 |
| 13 | $X_1$VQLV$X_2$SGGGLVQPGGSLRLSCAASGFKITHYTMGW$X_3$RQAPGK$X_4$ $X_5$E$X_6$VSRITWGGDNTFYSNSVKGRFTISRDNSKNT$X_7$YLQMNSLRAED TAVYYCAAGSTSTATPLRVDYWGQGTLVTVSS, where $X_1$ = D or E, $X_2$ = A or E, $X_3$ = F or V, $X_4$ = E or G, $X_5$ = R or L, $X_6$ = F or W, $X_7$ = L or V; | Humanized FC5 consensus |
| 14 | DVQLQASGGGLVQAGGSLRLSCAASGFKITHYTMGWFRQAPGKERE FVSRITWGGDNTFYSNSVKGRFTISRDNAKNTVYLQMNSLKPEDTADY YCAAGSTSTATPLRVDYWGKGTQVTVSS | FC5 |
| 15 | EVQLVESGGGLVQPGGSLRLSCAASGFKITHYTMGWVRQAPGKGLE WVSRITWGGDNTFYSNSVKGRFTISRDNSKNTLYLQMNSLRAEDTAV YYCAAGSTSTATPLRVDYWGQGTLVTVSS | FC5-H1 |
| 16 | EVQLVESGGGLVQPGGSLRLSCAASGFKITHYTMGVVRQAPGKGLE WVSRITWGGDNTFYSNSVKGRFTISRDNSKNTVYLQMNSLRAEDTAV YYCAAGSTSTATPLRVDYWGQGTLVTVSS | FC5-H2 |
| 17 | EVQLVESGGGLVQPGGSLRLSCAASGFKITHYTMGWFRQAPGKGLEF VSRITWGGDNTFYSNSVKGRFTISRDNSKNTVYLQMNSLRAEDTAVYY CAAGSTSTATPLRVDYWGQGTLVTVSS | FC5-H3 |
| 18 | $VX_1V X_2LX_3$ESGGGLVQ$X_4$GGSLRLSC$X_5$ASEYPSNFYAMSW$X_6$RQAPGK $X_7X_8EX_9VX_{10}$GVSRDGLTTLYADSVKGRFT$X_{11}$SRDN$X_{12}$KNT$X_{13}X_{14}$LQM NS$X_{15}X_{16}$AEDTAVYYCAIVITGVWNKVDVNSRSYHYWGQT$X_{17}$VTVSS, where $X_1$ is E or Q; $X_2$ is K or Q; $X_3$ is V or E; $X_4$ is A or P; $X_5$ is V or A; $X_6$ is F or V; $X_7$ is E or G; $X_8$ is R or L; $X_9$ is F or W; $X_{10}$ is A or S; $X_{11}$ is M or I; $X_{12}$ is A or S; $X_{13}$ is V or L; $X_{14}$ is D or Y; $X_{15}$ is V or L; $X_{16}$ is K or R; and $X_{17}$ is Q or L, | IGF1R-3 Consensus |
| 19 | QVKLEESGGGLVQAGGSLRLSCVASEYPSNFYAMSWFRQAPGKERE FVAGVSRDGLTTLYADSVKGRFTMSRDNAKNTVDLQMNSVKAEDTAV YYCAIVITGVWNKVDVNSRSYHYWGQGTQVTVSS | IGF1R-3 |
| 20 | EVQLVESGGGLVQPGGSLRLSCAASEYPSNFYAMSWFRQAPGKERE FVSGVSRDGLTTLYADSVKGRFTISRDNSKNTLYLQMNSLRAEDTAVY YCAIVITGVWNKVDVNSRSYHYWGQGTLVTVSS | IGF1R-3-H5 |
| 21 | $X_1VX_2LX_3$ESGGGLVQ$X_4$GGSLRLSC$X_5X_6$SGGTVSPTAMGW$X_7$RQAPG K$X_8X_9EX_{10}VX_{11}$HITWSRGTTR$X_{12}$ASSVK$X_{13}$RFTISRD$X_{14}X_{15}$KNT$X_{16}$YLQ MNSL$X_{17}X_{18}$EDTAVYYCAASTFLRILPEESAYTYWGQGT$X_{19}$VTVSS, where $X_1$ is E or Q; $X_2$ is K or Q; $X_3$ is V or E; $X_4$ is A or P; $X_5$ is A or E; $X_6$ is V or A; $X_7$ is V or F; $X_8$ is G or E; $X_9$ is L or R; $X_{10}$ is F or W; $X_{11}$ is G or S; $X_{12}$ is V or Y; $X_{13}$ is D or G; $X_{14}$ is N or S; $X_{15}$ is A or S; $X_{16}$ is L or V; $X_{17}$ is K or R; $X_{18}$ is A or S; and $X_{19}$ is L or Q, | IGF1R-4 Consensus |
| 22 | QVKLEESGGGLVQAGGSLRLSCEVSGGTVSPTAMGWFRQAPGKERE FVGHITWSRGTTRVASSVKDRFTISRDSAKNTVYLQMNSLKSEDTAVY YCAASTFLRILPEESAYTYWGQGTQVTVSS | IGF1R-4 |

| SEQ ID NO: | Sequence | Description |
|---|---|---|
| 23 | QVQLVESGGGLVQPGGSLRLSCAVSGGTVSPTAMGWFRQAPGKGLE FVGHITWSRGTTRYASSVKGRFTISRDNSKNTVYLQMNSLRAEDTAVY YCAASTFLRILPEESAYTYWGQGTLVTVSS | IGF1R-4-H3 |
| 24 | $X_1 V X_2 L X_3$ESGGGLVQ$X_4$GGSLRLSCAASGRTIDNYAMAW$X_5$RQAPGK$X_6$ $X_7 E X_8 V X_9$TIDWGDGG$X_{10}$RYANSVKGRFTISRDN$X_{11}$K$X_{12}$T$X_{13}$YLQMN$X_{14}$ L$X_{15} X_{16}$EDTAVY$X_{17}$CAMARQSRVNLDVARYDYWGQGT$X_{18}$VTVSS, where $X_1$ is E or Q; $X_2$ is K or Q; $X_3$ is V or E; $X_4$ is A or P; $X_5$ is V or S; $X_6$ is D or G; $X_7$ is L or R; $X_8$ is F or W; $X_9$ is A or S; $X_{10}$ is A or T; $X_{11}$ is A or S; $X_{12}$ is G or N; $X_{13}$ is M or L; $X_{14}$ is N or R; $X_{15}$ is E or R; $X_{16}$ is P or A; $X_{17}$ is S or Y; and $X_{18}$ is Q or L, | IGF1R-5 Consensus |
| 25 | QVKLEESGGGLVQAGGSLRLSCAASGRTIDNYAMAWSRQAPG KDREFVATIDWGDGGARYANSVKGRFTISRDNAKGTMYLQMN NLEPEDTAVYSCAMARQSRVNLDVARYDYWGQGTQVTVSS | IGF1R-5 |
| 26 | QVQLVESGGGLVQPGGSLRLSCAASGRTIDNYAMAWVRQAPG KGLEWVATIDWGDGGTRYANSVKGRFTISRDNSKNTMYLQMN SLRAEDTAVYYCAMARQSRVNLDVARYDYWGQGTLVTVSS | IGF1R-5-H2 |
| 27 | SGKTEYMAFPKPFESSSSIGAEKPRNKKLPEEEVESSRTPWLYEQEG EVEKPFIKTGFSVSVEKSTSSNRKNQLDTNGRRRQFDEESLESFSSMP DPVDPTTVTKTFKTRKASAQASLASKDKTPKSKSKKRNSTQLKSRVKN ITHARRILQQSNRNACNEAPETGSDFSMFEA | PK-4 |
| 28 | FSSMPDPVDPTTVTKTFKTRKASAQASLASKDKTPKSKSK | P4 peptide |
| 29 | KDKTPKSKSKKRNSTQLKSRVKNITHARRILQQSNRNACN | P5 peptide |
| 30 | KTFKTRKASAQASLASKDKTPKSKSKKRNSTQLKSRVKNI | P4-5 peptide (ABP) |
| 31 | $X_1$TF$X_2$T$X_3 X_4$ASAQASLASKDKTPKSKSKK$X_5 X_6$STQL$X_7$S$X_8$V$X_9$NI here $X_1$ = G or A, $X_2$ = G or V, $X_3$ = G or A, $X_4$ = G or A, $X_5$ = G or V, $X_6$ = G or V, $X_7$ = G or V, $X_8$ = G or A, $X_9$ = G or A (SEQ ID NO: 31) | ABP consensus |
| 32 | KTFKTRKASAQASLASKDKTPKSKSKKRGSTQLKSRVKNI | [ABP(G)] |
| 33 | KTFKTRKASAQASLASKDKTPKSKSKKGGSTQLKSRVKNI | [ABP(GG)] |
| 34 | KTFKTRGASAQASLASKDKTPKSKSKKRGSTQLKSRVKNI | [ABP(RG-G)] |
| 35 | KTFKTGGASAQASLASKDKTPKSKSKKRGSTQLKSRVKNI | [ABP(GG-G)] |
| 36 | GTFGTGGASAQASLASKDKTPKSKSKKGGSTQLKSRVKNI | [ABP(6G)] |
| 37 | KTFKTRKASAQASLASKDKTPKSKSKKGGSTVKNI | [ABP(GGspv)] |
| 38 | KTFKTRKASAQASLASKDKTPKSKSKKRG | [ABP(trc)] |
| 39 | ASEPRGPTIKPCPPCKCPAPNLLGGPSVFIFPPKIKDVLMISLSPIVTCV VVDVSEDDPDVQISWFVNNVEVHTAQTQTHREDYNSTLRVVSALPIQH QDWMSGKEFKCKVNNKDLPAPIERTISKPKGSVRAPQVYVLPPPEEE MTKKQVTLTCMVTDFMPEDIYVEVVTNNGKTELNYKNTEPVLDSDGSY FMYSKLRVEKKNWVERNSYSCSVVHEGLHNHHTTKSFSRTPG | Mouse Fc2a |
| 40 | AEPKSSDKTHTCPPCPAPELLGGPSVFLFPPKPKDTLMISRTPEVTCV VVDVSHEGPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPG | Human Fc1x7 |
| 41 | AEPKSCDKTHTCPPCPAPELLGGPSVFLFPPKPKDTLMISRTPEVTCV VVDVSHEGPEVKFNWHVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEGLHNHYTQK SLSLSPG | Human Fc1X0 |
| 42 | EVQLQASGGGLVQAGGSLRLSCAASGFKITHYTMGWFRQAPGKERE FVSRITWGGDNTFYSNSVKGRFTISRDNAKNTVYLQMNSLKPEDTADY YCAAGSTSTATPLRVDYWGKGTQVTVSSASEPRGPTIKPCPPCKCPA PNLLGGPSVFIFPPKIKDVLMISLSPIVTCVVVDVSEDDPDVQISWFVN | FC5-mFc2a-ABP |

| SEQ ID NO: | Sequence | Description |
|---|---|---|
| | NVEVHTAQTQTHREDYNSTLRVVSALPIQHQDWMSGKEFKCKVNNKD<br>LPAPIERTISKPKGSVRAPQVYVLPPPEEEMTKKQVTLTCMVTDFMPE<br>DIYVEWTNNGKTELNYKNTEPVLDSDGSYFMYSKLRVEKKNWVERNS<br>YSCSVVHEGLHNHHTTKSFSRTPGTGGGGSGGGGSKTFKTRKASAQ<br>ASLASKDKTPKSKSKKRNSTQLKSRVKNI | |
| 43 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSASEPRGPTIKPCPPCKCPAP<br>NLLGGPSVFIFPPKIKDVLMISLSPIVTCVVVDVSEDDPDVQISWFVNNV<br>EVHTAQTQTHREDYNSTLRVVSALPIQHQDWMSGKEFKCKVNNKDLP<br>APIERTISKPKGSVRAPQVYVLPPPEEEMTKKQVTLTCMVTDFMPEDIY<br>VEWTNNGKTELNYKNTEPVLDSDGSYFMYSKLRVEKKNWVERNSYS<br>CSVVHEGLHNHHTTKSFSRTPGTGGGGSGGGGSKTFKTRKASAQAS<br>LASKDKTPKSKSKKRNSTQLKSRVKNI | FC5-H3-mFc2a-<br>L-ABP |
| 44 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSAEPKSSDKTHTCPPCPAPEL<br>LGGPSVFLFPPKPKDTLMISRTPEVTCVVVDVSHEGPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSLSPGTGGGSGGGGSKTFKTRKASAQASLA<br>SKDKTPKSKSKKRNSTQLKSRVKNI | FC5-H3-<br>hFc1X7-L-ABP |
| 45 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSAEPKSSDKTHTCPPCPAPEL<br>LGGPSVFLFPPKPKDTLMISRTPEVTCVVVDVSHEGPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTC LVKGFYPSDIA<br>VEWESNGQPENNYKTTPPVLDSDGSFFLYSKLTVDKSRWQQGNVFS<br>CSVMHEALHNHYTQKSLSLSPGTGGGSGGGGSKTFKTRKASAQASLA<br>SKDKTPKSKSKKRGSTQLKSRVKNI | FC5-H3-<br>hFc1X7-L-<br>ABP(G) |
| 46 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSAEPKSSDKTHTCPPCPAPEL<br>LGGPSVFLFPPKPKDTLMISRTPEVTCVVVDVSHEGPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGTGGGSGGGGSKTFKTGG<br>ASAQASLASKDKTPKSKSKKRGSTQLKSRVKNI | FC5-H3-<br>hFc1X7-L-<br>ABP(GG-G) |
| 47 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSAEPKSSDKTHTCPPCPAPEL<br>LGGPSVFLFPPKPKDTLMISRTPEVTCVVVDVSHEGPEVKFNWYVDGV<br>EVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIA<br>VEWESNGQPENNYKTTPPVLDSDGSFFLYSKLTVDKSRWQQGNVFS<br>CSVMHEALHNHYTQKSLSLSPGTGGGSGGGGSGTFGTGGASAQASL<br>ASKDKTPKSKSKKGGSTQLKSRVKNI | FC5-H3-<br>hFc1X7-L-<br>ABP(6G) |
| 48 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSGGGGSGGGGSKTFKTGGAS<br>AQASLASKDKTPKSKSKKRGSTQLKSRVKNIGGGGSGGGGSAEPKSS<br>DKTHTCPPCPAPELLGGPSVFLFPPKPKDTLMISRTPEVTCVVVDVSH<br>EGPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKL<br>TVDKSRWQQGNVFSCSVMHEALHNHYTQKSLSLSPG | FC5(H3)-L-<br>ABP(GG-G)-L<br>hFc1X7 |
| 49 | EVQLVESGGGLVQPGGSLRLSCAASGFKITHYTMGWFRQAPGKGLEF<br>VSRITWGGDNTFYSNSVKGRFTISRDNSKNTVYLQMNSLRAEDTAVYY<br>CAAGSTSTATPLRVDYWGQGTLVTVSSAEPKSCDKTHTCPPCPAPEL<br>LGGPSVFLFPPKPKDTLMISRTPEVTCVVVDVSHEGPEVKFNWHVDG<br>VEVHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSDI<br>AVEWESNGQPENNYKTTPPVLDSDGSFFLYSKLTVDKSRWQQGNVF<br>SCSVMHEGLHNHYTQKSLSLSPGTGGGSGGGGSKTFKTGGASAQAS<br>LASKDKTPKSKSKKRGSTQLKSRVKNI | FC5-H3-<br>hFc1X0-L-<br>ABP(GG-G) |

-continued

| SEQ ID NO: | Sequence | Description |
|---|---|---|
| 50 | QVQLVESGGGLVQPGGSLRLSCAASGRTIDNYAMAWVRQAPGKGLE WVATIDWGDGGTRYANSVKGRFTISRDNSKNTMYLQMNSLRAEDTAV YYCAMARQSRVNLDVARYDYWGQGTLVTVSSAEPKSSDKTHTCPPC PAPELLGGPSVFLFPPKPKDTLMISRTPEVTCVVVDVSHEGPEVKFNW YVDGVEVHNAKTKPREEQYNSTYRVVSVLTVLHQDWLNGKEYKCKVS NKALPAPIEKTISKAKGQPREPQVYTLPPSRDELTKNQVSLTCLVKGFY PSDIAVEWESNGQPENNYKTTPPVLDSDGSFFLYSKLTVDKSRWQQG NVFSCSVMHEALHNHYTQKSLSLSPGTGGGSGGGGSKTFKTGGASA QASLASKDTPKSKSKKRGSTQLKSRVKNI | IGF1R5-H2-hFc1X7-L-ABP(GG-G) |
| 51 | KTFKTGGASAQASLASKDTPKSKSKKRGSTQLKSRVKNIGGGSGGG GSAEPKSSDKTHTCPPCPAPELLGGPSVFLFPPKPKDTLMISRTPEVT CVVVDVSHEGPEVKFNWYVDGVEVHNAKTKPREEQYNSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDGS FFLYSKLTVDKSRWQQGNVFSCSVMHEALHNHYTQKSLSLSPGQVQL VESGGGLVQPGGSLRLSCAASGRTIDNYAMAWVRQAPGKGLEWVATI DWGDGGTRYANSVKGRFTISRDNSKNTMYLQMNSLRAEDTAVYYCA MARQSRVNLDVARYDYWGQGTLVTVSS | ABP(GG-G)-L-hFc1X7-IGF1R5-H2 |
| 52 | AEPKSSDKTHTCPPCPAPELLGGPSVFLFPPKPKDTLMISRTPEVTCV VVDVSHEGPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSPGGGGSG GGGSKTFKTGGASAQASLASKDTPKSKSKKRGSTQLKSRVKNIGGG SGGGGSQVQLVESGGGLVQPGGSLRLSCAASGRTIDNYAMAWVRQA PGKGLEWVATIDWGDGGTRYANSVKGRFTISRDNSKNTMYLQMNSLR AEDTAVYYCAMARQSRVNLDVARYDYWGQGTLVTVSS | hFc1X7-L-ASP(GG-G)-L-IGF1R5-H2 |
| 53 | EVQLVESGGGLVQPGGSLRLSCAASGFKITHYTMGWFRQAPGKGLEF VSRITWGGDNTFYSNSVKGRFTISRDNSKNTVYLQMNSLRAEDTAVYY CAAGSTSTATPLRVDYWGQGTLVTVSSAEPKSSDKTHTCPPCPAPEL LGGPSVFLFPPKPKDTLMISRTPEVTCVVVDVSHEGPEVKFNWYVDGV EVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFS CSVMHEALHNHYTQKSLSLSPGT$X_1GX_2X_3GX_4X_5GX_6$, GTFGTGGASAQ ASLASKDTPKSKSKKGGSTQLKSRVKNI where $X_1$ = A or G., $X_2$ = A or G, $X_3$ = S or T, $X_4$ = G or V, $X_5$ = A or V, $X_6$ = S or T | FC5-H3-hFc1X7-L(consensus)-ABP(6G) |

REFERENCES

All patents, patent applications and publications referred to herein and throughout the application are hereby incorporated by reference.

Abbott N J (2013) Blood-brain barrier structure and function and the challenges for CNS drug delivery. J Inherit Metab Dis. 36(3):437-49.

Arbabi-Ghahroudi M, Desmyter A, Wyns L, Hamers R, and Muyldermans S (1997) Selection and identification of single domain antibody fragments from camel heavy-chain antibodies, FEBS Lett 414, 521-526

Barageb S H, Sonawane K D (2015) Amyloid cascade hypothesis: Pathogenesis and therapeutic strategies in Alzheimer's disease. Neuropeptides doi: 0.10 16/j.npep.20 15 0.06.008

Bard F et. al. (2000) Peripherally administered antibodies against amyloid beta-peptide enter the central nervous system and reduce pathology in a mouse model of Alzheimer disease Nat Med. 6, 916-919.

Bell A, Wang Z J, Arbabi-Ghahroudi M, Chang T A, Durocher Y, Trojahn U, Baardsnes J, Jaramillo M L, Li S, Baral T N, O'Connor-McCourt M, Mackenzie R, and Zhang J. (2010) Differential tumor-targeting abilities of three single-domain antibody formats. Cancer Lett. 289, 81-90.

Caram-Salas N, Boileau E, Farrington G K, Garber E, Brunette E, Abulrob A, Stanimirovic D. In vitro and in vivo methods for assessing FcRn-mediated reverse transcytosis across the blood-brain barrier. Methods Mol Biol. 2011; 763: 383-401.

Chakravarthy B, Michel Menard, Leslie Brown, Melissa Hewitt, Trevor Atkinson, and James Whitfield. (2013) A synthetic peptide corresponding to a region of the human pericentriolar material 1 (PCM-1) protein binds 13-amyloid (A/31-42) oligomers. J. Neurochem. 126, 415-424.

Chakravarthy B, Shingo Ito, Trevor Atkinson, Chantal Gaudet, Michel Menard, Leslie Brown, James Whitfield. (2014) Evidence that a synthetic amyloid-13 oligomer-binding peptide (ABP) targets amyloid-13 deposits in transgenic mouse rain and human Alzheimer's disease brain. Biochem. Biophys. Res. Commun. 445: 656-660.

Chothia C., and Lesk A. M. (1987) Canonical structures for the hypervariable regions of immunoglobulins. J. Mol. Biol. 196, 901-917.

Davies J., and L. Riechmann. (1996), Affinity improvement of single antibody VH domains: residues in all three hypervariable regions affect antigen binding. Immunotechnology 2, 169-179

DeLaGarza, V. W. (2003) Pharmacologic treatment of Alzheimer's disease: an update. Am Fam Physician. 68, 1365-72.

Dumoulin, M., Conrath, K., Van Meirhaighe, A., Meersman, F., Heremans, K., Frenken, L. G., Muyldermans, S., Wyns, L., and Matagne, A. (2002) Single-domain antibody fragments with high conformational stability. Protein Sci 11, 500-515.

Durocher Y, Perret S, Kamen A. (2002) High-level and high-throughput recombinant protein production by transient transfection of suspension-growing human 293-EBNA1 cells. Nucleic Acids Res. 30 (2):E9.

Eisenberg, D., Schwarz, E., Komaromy, M., and Wall, R. (1984) Analysis of membrane and surface protein sequences with the hydrophobic moment plot. J. Mol. Biol. 179, 125-142

Farrington G K, Caram-Salas N, Haqqani AS, Brunette E, Eldredge J, Pepinsky B, Antognetti G, Baumann E, Ding W, Garber E, Jiang S, Delaney C, Boileau E, Sisk W P, Stanimirovic D B. (2014) A novel platform for engineering blood-brain barrier-crossing bispecific biologics. FASEB J. 28, 4764-4778.

Garberg, P., Ball, M., Borg, N., Cecchelli, R., Fenart, L., Hurst, R. D., Lindmark, T., Mabondzo, A., Nilsson, J. E., Raub, T. J., Stanimirovic, D., Terasaki, T., Oberg, J.-O., and Osterberg, T. (2005) In vitro models for the blood-brain barrier. Toxicol. In Vitro 19, 299-334

Gonzales N R, DePascalis R, Schlom J, Kashmiri S V S (2005) Minimizing the Immunogenicity of Antibodies for Clinical Application. Tumor Biol 26, 31-43

Gottesman M M and Pastan I (1993) Biochemistry of multidrug resistance mediated by the multidrug transporter. Ann. Rev. Biochem. 62, 385-427

Goure W F, Krafft G A, Jerecic J, Hefti F. (2014) Alzheimer's Research & Therapy Targeting the proper amyloid-beta neuronal toxins: a path forward for Alzheimer's disease. Immunotherapeutics, 6, 42-56.

Gergov M, Ojanpera I, Vuori E. (2003) Simultaneous screening for 238 drugs in blood by liquid chromatography-ionspray tandem mass spectrometry with multiple-reaction monitoring. Journal of Chromatography B, 795, 41-53

Hardy J, Bogdanovic N, Winblad B, Portelius E, Andreasen N, Cedazo-Minguez A, Zetterberg H. (2014) Pathways to Alzheimer's disease. J Intern Med. 275, 296-303.

Hamers-Casterman, C., Atarhouch, T., Muyldermans, S., Robinson, G., Hamers, C., Songa, E. B., Bendahman, N., and Hamers, R. (1993) Naturally occurring antibodies devoid of light chains. Nature 363, 446-448.

Haqqani, A. S., Caram-Salas, N., Ding, W., Brunette, E., Delaney, C. E., Baumann, E., Boileau, E., and Stanimirovic, D. (2013) Multiplexed evaluation of serum and CSF pharmacokinetics of brain-targeting single-domain antibodies using a NanoLC-SRM-ILIS method. Mol. Pharm. 10, 1542-1556

Huang Y L, Sa"Ijo" A, Suneson A, Hansson H A. (1995) A new approach for multiple sampling of cisternal cerebrospinal fluid in rodents with minimal trauma and inflammation. J Neurosci Meth; 63:13-22.

Hussack G., Hirama T., Ding W., MacKenzie R., and Tanha J. (2011) Engineered Single-Domain Antibodies with High Protease Resistance and Thermal Stability PLoS ONE 6, e28218.

Hussack G, Arbabi-Ghahroudi M, van Faassen H, Songer J G, Ng K K, MacKenzie R, Tanha J (2011b) Neutralization of *Clostridium difficile* toxin A with single-domain antibodies targeting the cell receptor binding domain. J Biol Chem. 286(11): 8961-76.

Iqbal U., Trojahn U., Albaghdadi H., Zhang J., O'Connor M., Stanimirovic D., Tomanek B., Sutherland G., and Abulrob A. (2010) Kinetic analysis of novel mono- and multivalent VHH-fragments and their application for molecular imaging of brain tumours. Br. J. Pharmacol. 160, 1016-1028.

Jespers, L., Schon, O., Famm, K., and Winter, G. (2004) Aggregation-resistant domain antibodies selected on phage by heat denaturation. Nat. Biotechnol. 22, 1161-1165.

Ji W and Ha I (2010) Drug Development for Alzheimer's Disease: Recent Progress Experimental Neurobiology 19, 120-131.

Jones P T, Dear P H, Foote J, Neuberger M S, Winter G (1986) Replacing the complementarity-determining regions in a human antibody with those from a mouse. Nature 321, 522-525.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Kim, D. Y., Kandalaft, H., Ding, W., Ryan, S., van Fassen, H., Hirama, T., Foote, S. J., MacKenzie, R., and Tanha, J. (2012) Disulfide linkage engineering for improving biophysical properties of human VH domains PEDS advance access Aug. 30, 2012, 1-9.

Kornhuber M E, Kornhuber J, Cimniak U. (1986) A method for repeated CSF sampling in the freely moving rat. J Neurosci Meth 1986; 17:63-68.

Lannfelt L, Relkin, N R, Siemers E R (2014) Amyloid-f3-directed immunotherapy for Alzheimer's disease. J Intern Med. 275, 284-295.

Li S, Zheng W, Kuolee R, Hirama T, Henry M, Makvandi-Nejad S, Fjallman T, Chen W, Zhang J. Pentabody-mediated antigen delivery induces antigen-specific mucosal immune response. Mol Immunol 2009; 46:1718-26.

Mangialasche F, Solomon A, Winblad B, Mecocci P, Kivipelto M (20 10) Alzheimer's disease: clinical trials and drug development. Lancet Neurol 9, 702-716

Monsonego A, and Weiner H (2003) Immunotherapeutic approaches to Alzheimer's disease Science. 302, 834-838.

Morrone C D, Mingzhe Liu M, Black S E, McLaurin J A (2015) Interaction between therapeutic interventions for Alzheimer's disease and physiological Af3 clearance mechanisms. Frontiers in Aging Neuroscience. 7, Article 64, 1-16.

Musiek E S, Holtzman D M (2015) Three dimensions of the amyloid hypothesis: time, space and "wingmen". Nature Neurosci. 18, 800-806.

Nicaise M, Valeio-Lepiniec M, Minard P, Desmadril M. (2004) Affinity transfer by CDR grafting on a nonimmunoglobulin scaffold. Protein Sci. 13(7): 1882-1891.

Nuttall, S. D., Krishnan, U. V., Doughty, L., Pearson, K., Ryan, M. T., Hoogenraad, N. J., Hattarki, M., Carmichael, J. A., Irving, R. A., and Hudson, P. J. (2003) Isolation and characterization of an IgNAR variable domain specific for the human mitochondrial translocase receptor Tom70. Eur. J. Biochem. 270, 3543-3554.

Padlan E A (1991) A possible procedure for reducing the immunogenicity of antibody variable domains while preserving their ligand-binding properties. Mol Immunol 28, 489-498.

Pardridge, W. M., Adv. Drug Delivery Reviews, 15, 5-36 (1995)

Pardridge, W. M. Drug and gene delivery to the brain: the vascular route, Neuron. 2002, 36, 555-558.

Queen C, Schneider W P, Selick H E, Payne P W, Landolfi N F, Duncan J F, Avdalovic N M, Levitt M, Junghans R P, Waldmann T A (1989) A humanized antibody that binds to the interleukin 2 receptor. Proc Natl Acad Sci USA 86, 10029-10033.

Rafii M S, Aisen P S. (2015) Advances in Alzheimer's disease drug development. BMC Med. 13:62.

Riechmann L, Clark M, Waldmann H, Winter G (1988) Reshaping human antibodies for therapy. Nature 332, 323-327.

Samuels B. L., J. Clin. Pharmacol. (1993) Modulation of vinblastine resistance with cyclosporine: a phase I study. Ther. 54, 421-429

Savonenko A V, Melnikova T, Hiatt A, LiT, Worley P F, Troncoso J C, Wong P C, Price D L. (2012) Alzheimer's therapeutics: translation of preclinical science to clinical drug development. Neuropsychopharmacology. 37, 261-277

Selkoe D J, and Hardy J (2016) The amyloid hypothesis of Alzheimer's disease at 25 years EMBO Molecular Medicine. 8, 595-608

Sengupta U, Nilson A N, Kayed R (2016) The Role of Amyloid-β Oligomers in Toxicity, Propagation, and Immunotherapy. EBioMedicine. 6:42-49

Sevigny J et al., (2016) The antibody aducanumab reduces Aβ plaques in Alzheimer's disease. Nature. 537, 50-56

Shields R L, Namenuk A K, Hong K, Meng Y G, Rae J, Briggs J, Xie D, Lai J, Stadlen A, Li B, Fox J A, Presta L G (2001) High resolution mapping of the binding site on human IgG1 for Fc gamma RI, Fc gamma RII, Fc gamma RIII, and FcRn and design of IgG1 variants with improved binding to the Fc gamma R. J Biol Chem. 276, 6591-6604.

Tempest P R, Bremmer P, Lambert M, Taylor G, Furze J M, Carr F J, Harris W J (1991) Reshaping a human monoclonal antibody to inhibit human respiratory syncytial virus infection in vivo. Biotechnology 9, 266-271.

To R, Hirama T, Arbabi-Ghahroudi M, MacKenzie R, Wang P, Xu P, Ni F, and Tanha J. (2005) Isolation of Monomeric Human VHS by a Phage Selection. J. Biol. Chem. 280, 41395-41403.

Tsurushita N, Hinton, RP, Kumar S (2005) Design of humanized antibodies: From anti-Tac to Zenapax. Methods 36, 69-83.

Watanabe, T. (1995) Comparative Study on Reversal Efficacy of SDZ PSC 833, Cyclosporin a and Verapamil on Multidrug Resistance in Vitro and in Vivo Acta Oncol., 34, 235-241

WO 95/04069
WO/2004/076670
WO2003/046560
WO 2002/057445
WO 2011/127580
WO 2007/036021
WO 2006/133566

The invention claimed is:

1. A fusion protein comprising the amino acid sequence of SEQ ID NO: 47.

2. The fusion protein of claim 1, consisting of the amino acid sequence of SEQ ID NO: 47.

3. A pharmaceutical composition comprising the fusion protein of claim 1 and a pharmaceutically acceptable diluent, carrier, vehicle or excipient.

4. A pharmaceutical composition comprising the fusion protein of claim 2 and a pharmaceutically acceptable diluent, carrier, vehicle or excipient.

5. A dimer of two fusion proteins of claim 1.

6. The dimer of claim 5, wherein each of the two fusion proteins consists of the amino acid sequence of SEQ ID NO: 47.

7. A pharmaceutical composition comprising the dimer of claim 5 and a pharmaceutically acceptable diluent, carrier, vehicle or excipient.

8. A pharmaceutical composition comprising the dimer of claim 6 and a pharmaceutically acceptable diluent, carrier, vehicle or excipient.

* * * * *

SEQUENCE LISTING

```
<160> NUMBER OF SEQ ID NOS: 66

<210> SEQ ID NO 1
<211> LENGTH: 10
<212> TYPE: PRT
<213> ORGANISM: Artificial Sequence
<220> FEATURE:
<223> OTHER INFORMATION: CDR1 FC5

<400> SEQUENCE: 1

Gly Phe Lys Ile Thr His Tyr Thr Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2 FC5

<400> SEQUENCE: 2

Arg Ile Thr Trp Gly Gly Asp Asn Thr Phe Tyr Ser Asn Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: CDR3 FC5

<400> SEQUENCE: 3

Gly Ser Thr Ser Thr Ala Thr Pro Leu Arg Val Asp Tyr
1               5                   10
```

```
<210> SEQ ID NO 4
<211> LENGTH: 8
<212> TYPE: PRT
<213> ORGANISM: Artificial Sequence
<220> FEATURE:
<223> OTHER INFORMATION: CDR1 IGF1R-3

<400> SEQUENCE: 4

Glu Tyr Pro Ser Asn Phe Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: CDR2 IGF1R-3

<400> SEQUENCE: 5

Val Ser Arg Asp Gly Leu Thr Thr
1               5

<210> SEQ ID NO 6
<211> LENGTH: 20
<212> TYPE: PRT
<213> ORGANISM: Artificial Sequence
<220> FEATURE:
<223> OTHER INFORMATION: CDR3 IGF1R-3

<400> SEQUENCE: 6

Ala Ile Val Ile Thr Gly Val Trp Asn Lys Val Asp Val Asn Ser Arg
1               5                   10                  15

Ser Tyr His Tyr
            20

<210> SEQ ID NO 7
<211> LENGTH: 8
<212> TYPE: PRT
<213> ORGANISM: Artificial Sequence
<220> FEATURE:
<223> OTHER INFORMATION: CDR1 IGF1R-4

<400> SEQUENCE: 7

Gly Gly Thr Val Ser Pro Thr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: CDR2 IGF1R-4

<400> SEQUENCE: 8

Ile Thr Trp Ser Arg Gly Thr Thr
1               5

<210> SEQ ID NO 9
<211> LENGTH: 17
<212> TYPE: PRT
<213> ORGANISM: Artificial Sequence
<220> FEATURE:
<223> OTHER INFORMATION: CDR3 IGF1R-4

<400> SEQUENCE: 9

Ala Ala Ser Thr Phe Leu Arg Ile Leu Pro Glu Glu Ser Ala Tyr Thr
```

Tyr

<210> SEQ ID NO 10
<211> LENGTH: 8
<212> TYPE: PRT
<213> ORGANISM: Artificial Sequence
<220> FEATURE:
<223> OTHER INFORMATION: CDR1 IGF1R-5

<400> SEQUENCE: 10

Gly Arg Thr Ile Asp Asn Tyr Ala
1               5

<210> SEQ ID NO 11
<211> LENGTH: 8
<212> TYPE: PRT
<213> ORGANISM: Artificial Sequence
<220> FEATURE:
<223> OTHER INFORMATION: CDR2 IGF1R-5
<220> FEATURE:
<221> NAME/KEY: misc_feature
<222> LOCATION: (8)..(8)
<223> OTHER INFORMATION: where X is A or T

<400> SEQUENCE: 11

Ile Asp Trp Gly Asp Gly Gly Xaa
1               5

<210> SEQ ID NO 12
<211> LENGTH: 17
<212> TYPE: PRT
<213> ORGANISM: Artificial Sequence
<220> FEATURE:
<223> OTHER INFORMATION: CDR3 IGF1R-5

<400> SEQUENCE: 12

Ala Met Ala Arg Gln Ser Arg Val Asn Leu Asp Val Ala Arg Tyr Asp
1               5                   10                  15

Tyr

<210> SEQ ID NO 13
<211> LENGTH: 122
<212> TYPE: PRT
<213> ORGANISM: Artificial Sequence
<220> FEATURE:
<223> OTHER INFORMATION: Humanized FC5 consensus
<220> FEATURE:
<221> NAME/KEY: misc_feature
<222> LOCATION: (1)..(1)
<223> OTHER INFORMATION: where X is D or E
<220> FEATURE:
<221> NAME/KEY: misc_feature
<222> LOCATION: (6)..(6)
<223> OTHER INFORMATION: where X is A or E
<220> FEATURE:
<221> NAME/KEY: misc_feature
<222> LOCATION: (37)..(37)
<223> OTHER INFORMATION: where X is F or V
<220> FEATURE:
<221> NAME/KEY: misc_feature
<222> LOCATION: (44)..(44)
<223> OTHER INFORMATION: where X is E or G
<220> FEATURE:
<221> NAME/KEY: misc_feature
<222> LOCATION: (45)..(45)
<223> OTHER INFORMATION: where X is R or L
<220> FEATURE:
<221> NAME/KEY: misc_feature
<222> LOCATION: (47)..(47)

```
<223> OTHER INFORMATION: where X is F or W
<220> FEATURE:
<221> NAME/KEY: misc_feature
<222> LOCATION: (79)..(79)
<223> OTHER INFORMATION: where X is L or V

<400> SEQUENCE: 13

Xaa Val Gln Leu Val Xaa Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Xaa Arg Gln Ala Pro Gly Lys Xaa Xaa Glu Xaa Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
            115                 120

<210> SEQ ID NO 14
<211> LENGTH: 122
<212> TYPE: PRT
<213> ORGANISM: Artificial Sequence
<220> FEATURE:
<223> OTHER INFORMATION: FC5

<400> SEQUENCE: 14

Asp Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
            115                 120

<210> SEQ ID NO 15
<211> LENGTH: 122
<212> TYPE: PRT
<213> ORGANISM: Artificial Sequence
<220> FEATURE:
<223> OTHER INFORMATION: FC5-H1

<400> SEQUENCE: 15

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Lys Ile Thr His Tyr
            20                  25                  30

Thr Met Gly Trp Val Arg Gln Ala Pro Gly Lys Gly Leu Glu Trp Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
            115                 120
```

<210> SEQ ID NO 16
<211> LENGTH: 122
<212> TYPE: PRT
<213> ORGANISM: Artificial Sequence
<220> FEATURE:
<223> OTHER INFORMATION: FC5-H2

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Val Arg Gln Ala Pro Gly Lys Gly Leu Glu Trp Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
            115                 120
```

<210> SEQ ID NO 17
<211> LENGTH: 122
<212> TYPE: PRT
<213> ORGANISM: Artificial Sequence
<220> FEATURE:
<223> OTHER INFORMATION: FC5-H3

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Ala Glu Asp Thr Ala Val Tyr Tyr Cys
                 85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser
        115                 120
```

<210> SEQ ID NO 18
<211> LENGTH: 127
<212> TYPE: PRT
<213> ORGANISM: Artificial Sequence
<220> FEATURE:
<223> OTHER INFORMATION: IGF1R-3 Consensus
<220> FEATURE:
<221> NAME/KEY: misc_feature
<222> LOCATION: (1)..(1)
<223> OTHER INFORMATION: where X is E or Q
<220> FEATURE:
<221> NAME/KEY: misc_feature
<222> LOCATION: (3)..(3)
<223> OTHER INFORMATION: where X is K or Q
<220> FEATURE:
<221> NAME/KEY: misc_feature
<222> LOCATION: (5)..(5)
<223> OTHER INFORMATION: where X is V or E
<220> FEATURE:
<221> NAME/KEY: misc_feature
<222> LOCATION: (14)..(14)
<223> OTHER INFORMATION: where X is A or P
<220> FEATURE:
<221> NAME/KEY: misc_feature
<222> LOCATION: (23)..(23)
<223> OTHER INFORMATION: where X is V or A
<220> FEATURE:
<221> NAME/KEY: misc_feature
<222> LOCATION: (37)..(37)
<223> OTHER INFORMATION: where X is F or V
<220> FEATURE:
<221> NAME/KEY: misc_feature
<222> LOCATION: (44)..(44)
<223> OTHER INFORMATION: where X is E or G
<220> FEATURE:
<221> NAME/KEY: misc_feature
<222> LOCATION: (45)..(45)
<223> OTHER INFORMATION: where X is R or L
<220> FEATURE:
<221> NAME/KEY: misc_feature
<222> LOCATION: (47)..(47)
<223> OTHER INFORMATION: where X is F or W
<220> FEATURE:
<221> NAME/KEY: misc_feature
<222> LOCATION: (49)..(49)
<223> OTHER INFORMATION: where X is A or S
<220> FEATURE:
<221> NAME/KEY: misc_feature
<222> LOCATION: (70)..(70)
<223> OTHER INFORMATION: where X is M or I
<220> FEATURE:
<221> NAME/KEY: misc_feature
<222> LOCATION: (75)..(75)
<223> OTHER INFORMATION: where X is A or S
<220> FEATURE:
<221> NAME/KEY: misc_feature
<222> LOCATION: (79)..(79)
<223> OTHER INFORMATION: where X is V or L
<220> FEATURE:
<221> NAME/KEY: misc_feature
<222> LOCATION: (80)..(80)
<223> OTHER INFORMATION: where X is D or Y
<220> FEATURE:
<221> NAME/KEY: misc_feature
<222> LOCATION: (86)..(86)
<223> OTHER INFORMATION: where X is V or L
<220> FEATURE:
<221> NAME/KEY: misc_feature
<222> LOCATION: (87)..(87)
<223> OTHER INFORMATION: where X is K or R
<220> FEATURE:
<221> NAME/KEY: misc_feature
<222> LOCATION: (122)..(122)
<223> OTHER INFORMATION: where X is Q or L

<400> SEQUENCE: 18

Xaa Val Xaa Leu Xaa Glu Ser Gly Gly Gly Leu Val Gln Xaa Gly Gly
1               5                   10                  15

Ser Leu Arg Leu Ser Cys Xaa Ala Ser Glu Tyr Pro Ser Asn Phe Tyr
            20                  25                  30

Ala Met Ser Trp Xaa Arg Gln Ala Pro Gly Lys Xaa Xaa Glu Xaa Val
        35                  40                  45

Xaa Gly Val Ser Arg Asp Gly Leu Thr Thr Leu Tyr Ala Asp Ser Val
50                  55                  60

Lys Gly Arg Phe Thr Xaa Ser Arg Asp Asn Xaa Lys Asn Thr Xaa Xaa
65                  70                  75                  80

Leu Gln Met Asn Ser Xaa Xaa Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Xaa Val Thr Val Ser Ser
        115                 120                 125

<210> SEQ ID NO 19
<211> LENGTH: 127
<212> TYPE: PRT
<213> ORGANISM: Artificial Sequence
<220> FEATURE:
<223> OTHER INFORMATION: IGF1R-3

<400> SEQUENCE: 19

Gln Val Lys Leu Glu Glu Ser Gly Gly Gly Leu Val Gln Ala Gly Gly
1               5                   10                  15

Ser Leu Arg Leu Ser Cys Val Ala Ser Glu Tyr Pro Ser Asn Phe Tyr
            20                  25                  30

Ala Met Ser Trp Phe Arg Gln Ala Pro Gly Lys Glu Arg Glu Phe Val
        35                  40                  45

Ala Gly Val Ser Arg Asp Gly Leu Thr Thr Leu Tyr Ala Asp Ser Val
50                  55                  60

Lys Gly Arg Phe Thr Met Ser Arg Asp Asn Ala Lys Asn Thr Val Asp
65                  70                  75                  80

Leu Gln Met Asn Ser Val Lys Ala Glu Asp Thr Ala Val Tyr Tyr Cys
                85                  90                  95

Ala Ile Val Ile Thr Gly Val Trp Asn Lys Val Asp Val Asn Ser Arg
            100                 105                 110

Ser Tyr His Tyr Trp Gly Gln Gly Thr Gln Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: IGF1R-3-H5

<400> SEQUENCE: 20

Glu Val Gln Leu Val Glu Ser Gly Gly Gly Leu Val Gln Pro Gly Gly
1               5                   10                  15

```
Ser Leu Arg Leu Ser Cys Ala Ala Ser Glu Tyr Pro Ser Asn Phe Tyr
         20                  25                  30

Ala Met Ser Trp Phe Arg Gln Ala Pro Gly Lys Glu Arg Glu Phe Val
         35                  40                  45

Ser Gly Val Ser Arg Asp Gly Leu Thr Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Val Ile Thr Gly Val Trp Asn Lys Val Asp Val Asn Ser Arg
                100                 105                 110

Ser Tyr His Tyr Trp Gly Gln Gly Thr Leu Val Thr Val Ser Ser
        115                 120                 125
```

```
<210> SEQ ID NO 21
<211> LENGTH: 124
<212> TYPE: PRT
<213> ORGANISM: Artificial Sequence
<220> FEATURE:
<223> OTHER INFORMATION: IGF1R-4 Consensus
<220> FEATURE:
<221> NAME/KEY: misc_feature
<222> LOCATION: (1)..(1)
<223> OTHER INFORMATION: where X is E or Q
<220> FEATURE:
<221> NAME/KEY: misc_feature
<222> LOCATION: (3)..(3)
<223> OTHER INFORMATION: where X is K or Q
<220> FEATURE:
<221> NAME/KEY: misc_feature
<222> LOCATION: (5)..(5)
<223> OTHER INFORMATION: where X is V or E
<220> FEATURE:
<221> NAME/KEY: misc_feature
<222> LOCATION: (14)..(14)
<223> OTHER INFORMATION: where X is A or P
<220> FEATURE:
<221> NAME/KEY: misc_feature
<222> LOCATION: (23)..(23)
<223> OTHER INFORMATION: where X is A or E
<220> FEATURE:
<221> NAME/KEY: misc_feature
<222> LOCATION: (24)..(24)
<223> OTHER INFORMATION: where X is V or A
<220> FEATURE:
<221> NAME/KEY: misc_feature
<222> LOCATION: (37)..(37)
<223> OTHER INFORMATION: where X is V or F
<220> FEATURE:
<221> NAME/KEY: misc_feature
<222> LOCATION: (44)..(44)
<223> OTHER INFORMATION: where X is G or E
<220> FEATURE:
<221> NAME/KEY: misc_feature
<222> LOCATION: (45)..(45)
<223> OTHER INFORMATION: where X is L or R
<220> FEATURE:
<221> NAME/KEY: misc_feature
<222> LOCATION: (47)..(47)
<223> OTHER INFORMATION: where X is F or W
<220> FEATURE:
<221> NAME/KEY: misc_feature
<222> LOCATION: (49)..(49)
<223> OTHER INFORMATION: where X is G or S
<220> FEATURE:
<221> NAME/KEY: misc_feature
<222> LOCATION: (60)..(60)
<223> OTHER INFORMATION: where X is V or Y
<220> FEATURE:
<221> NAME/KEY: misc_feature
```

```
<222> LOCATION: (66)..(66)
<223> OTHER INFORMATION: where X is D or G
<220> FEATURE:
<221> NAME/KEY: misc_feature
<222> LOCATION: (74)..(74)
<223> OTHER INFORMATION: where X is N or S
<220> FEATURE:
<221> NAME/KEY: misc_feature
<222> LOCATION: (75)..(75)
<223> OTHER INFORMATION: where X is A or S
<220> FEATURE:
<221> NAME/KEY: misc_feature
<222> LOCATION: (79)..(79)
<223> OTHER INFORMATION: where X is L or V
<220> FEATURE:
<221> NAME/KEY: misc_feature
<222> LOCATION: (87)..(87)
<223> OTHER INFORMATION: where X is K or R
<220> FEATURE:
<221> NAME/KEY: misc_feature
<222> LOCATION: (88)..(88)
<223> OTHER INFORMATION: where X is A or S
<220> FEATURE:
<221> NAME/KEY: misc_feature
<222> LOCATION: (119)..(119)
<223> OTHER INFORMATION: where X is L or Q

<400> SEQUENCE: 21

Xaa Val Xaa Leu Xaa Glu Ser Gly Gly Gly Leu Val Gln Xaa Gly Gly
1               5                   10                  15

Ser Leu Arg Leu Ser Cys Xaa Xaa Ser Gly Gly Thr Val Ser Pro Thr
            20                  25                  30

Ala Met Gly Trp Xaa Arg Gln Ala Pro Gly Lys Xaa Xaa Glu Xaa Val
        35                  40                  45

Xaa His Ile Thr Trp Ser Arg Gly Thr Thr Arg Xaa Ala Ser Ser Val
    50                  55                  60

Lys Xaa Arg Phe Thr Ile Ser Arg Asp Xaa Xaa Lys Asn Thr Xaa Tyr
65                  70                  75                  80

Leu Gln Met Asn Ser Leu Xaa Xaa Glu Asp Thr Ala Val Tyr Tyr Cys
                85                  90                  95

Ala Ala Ser Thr Phe Leu Arg Ile Leu Pro Glu Glu Ser Ala Tyr Thr
            100                 105                 110

Tyr Trp Gly Gln Gly Thr Xaa Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: IGF1R-4

<400> SEQUENCE: 22

Gln Val Lys Leu Glu Glu Ser Gly Gly Gly Leu Val Gln Ala Gly Gly
1               5                   10                  15

Ser Leu Arg Leu Ser Cys Glu Val Ser Gly Gly Thr Val Ser Pro Thr
            20                  25                  30

Ala Met Gly Trp Phe Arg Gln Ala Pro Gly Lys Glu Arg Glu Phe Val
        35                  40                  45

Gly His Ile Thr Trp Ser Arg Gly Thr Thr Arg Val Ala Ser Ser Val
    50                  55                  60

Lys Asp Arg Phe Thr Ile Ser Arg Asp Ser Ala Lys Asn Thr Val Tyr
65                  70                  75                  80

Leu Gln Met Asn Ser Leu Lys Ser Glu Asp Thr Ala Val Tyr Tyr Cys
```

```
                    85                  90                  95
Ala Ala Ser Thr Phe Leu Arg Ile Leu Pro Glu Glu Ser Ala Tyr Thr
                100                 105                 110

Tyr Trp Gly Gln Gly Thr Gln Val Thr Val Ser Ser
        115                 120

<210> SEQ ID NO 23
<211> LENGTH: 124
<212> TYPE: PRT
<213> ORGANISM: Artificial Sequence
<220> FEATURE:
<223> OTHER INFORMATION: IGF1R-4-H3

<400> SEQUENCE: 23

Gln Val Gln Leu Val Glu Ser Gly Gly Gly Leu Val Gln Pro Gly Gly
1               5                  10                  15

Ser Leu Arg Leu Ser Cys Ala Val Ser Gly Gly Thr Val Ser Pro Thr
                20                  25                  30

Ala Met Gly Trp Phe Arg Gln Ala Pro Gly Lys Gly Leu Glu Phe Val
            35                  40                  45

Gly His Ile Thr Trp Ser Arg Gly Thr Thr Arg Tyr Ala Ser Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Ser Thr Phe Leu Arg Ile Leu Pro Glu Glu Ser Ala Tyr Thr
                100                 105                 110

Tyr Trp Gly Gln Gly Thr Leu Val Thr Val Ser Ser
        115                 120

<210> SEQ ID NO 24
<211> LENGTH: 124
<212> TYPE: PRT
<213> ORGANISM: Artificial Sequence
<220> FEATURE:
<223> OTHER INFORMATION: IGF1R-5 Consensus
<220> FEATURE:
<221> NAME/KEY: misc_feature
<222> LOCATION: (1)..(1)
<223> OTHER INFORMATION: where X is E or Q
<220> FEATURE:
<221> NAME/KEY: misc_feature
<222> LOCATION: (3)..(3)
<223> OTHER INFORMATION: where X is K or Q
<220> FEATURE:
<221> NAME/KEY: misc_feature
<222> LOCATION: (5)..(5)
<223> OTHER INFORMATION: where X is V or E
<220> FEATURE:
<221> NAME/KEY: misc_feature
<222> LOCATION: (14)..(14)
<223> OTHER INFORMATION: where X is A or P
<220> FEATURE:
<221> NAME/KEY: misc_feature
<222> LOCATION: (37)..(37)
<223> OTHER INFORMATION: where X is V or S
<220> FEATURE:
<221> NAME/KEY: misc_feature
<222> LOCATION: (44)..(44)
<223> OTHER INFORMATION: where X is D or G
<220> FEATURE:
<221> NAME/KEY: misc_feature
<222> LOCATION: (45)..(45)
<223> OTHER INFORMATION: where X is L or R
<220> FEATURE:
<221> NAME/KEY: misc_feature
```

```
<222> LOCATION: (47)..(47)
<223> OTHER INFORMATION: where X is F or W
<220> FEATURE:
<221> NAME/KEY: misc_feature
<222> LOCATION: (49)..(49)
<223> OTHER INFORMATION: where X is A or S
<220> FEATURE:
<221> NAME/KEY: misc_feature
<222> LOCATION: (58)..(58)
<223> OTHER INFORMATION: where X is A or T
<220> FEATURE:
<221> NAME/KEY: misc_feature
<222> LOCATION: (75)..(75)
<223> OTHER INFORMATION: where X is A or S
<220> FEATURE:
<221> NAME/KEY: misc_feature
<222> LOCATION: (77)..(77)
<223> OTHER INFORMATION: where X is G or N
<220> FEATURE:
<221> NAME/KEY: misc_feature
<222> LOCATION: (79)..(79)
<223> OTHER INFORMATION: where X is M or L
<220> FEATURE:
<221> NAME/KEY: misc_feature
<222> LOCATION: (85)..(85)
<223> OTHER INFORMATION: where X is N or R
<220> FEATURE:
<221> NAME/KEY: misc_feature
<222> LOCATION: (87)..(87)
<223> OTHER INFORMATION: where X is E or R
<220> FEATURE:
<221> NAME/KEY: misc_feature
<222> LOCATION: (88)..(88)
<223> OTHER INFORMATION: where X is P or A
<220> FEATURE:
<221> NAME/KEY: misc_feature
<222> LOCATION: (95)..(95)
<223> OTHER INFORMATION: where X is S or Y
<220> FEATURE:
<221> NAME/KEY: misc_feature
<222> LOCATION: (119)..(119)
<223> OTHER INFORMATION: where X is Q or L

<400> SEQUENCE: 24

Xaa Val Xaa Leu Xaa Glu Ser Gly Gly Gly Leu Val Gln Xaa Gly Gly
1               5                   10                  15

Ser Leu Arg Leu Ser Cys Ala Ala Ser Gly Arg Thr Ile Asp Asn Tyr
            20                  25                  30

Ala Met Ala Trp Xaa Arg Gln Ala Pro Gly Lys Xaa Xaa Glu Xaa Val
        35                  40                  45

Xaa Thr Ile Asp Trp Gly Asp Gly Gly Xaa Arg Tyr Ala Asn Ser Val
    50                  55                  60

Lys Gly Arg Phe Thr Ile Ser Arg Asp Asn Xaa Lys Xaa Thr Xaa Tyr
65                  70                  75                  80

Leu Gln Met Asn Xaa Leu Xaa Xaa Glu Asp Thr Ala Val Tyr Xaa Cys
                85                  90                  95

Ala Met Ala Arg Gln Ser Arg Val Asn Leu Asp Val Ala Arg Tyr Asp
            100                 105                 110

Tyr Trp Gly Gln Gly Thr Xaa Val Thr Val Ser Ser
        115                 120

<210> SEQ ID NO 25
<211> LENGTH: 124
<212> TYPE: PRT
<213> ORGANISM: Artificial Sequence
<220> FEATURE:
<223> OTHER INFORMATION: IGF1R-5

<400> SEQUENCE: 25
```

Gln Val Lys Leu Glu Ser Gly Gly Gly Leu Val Gln Ala Gly Gly
1               5                   10                  15

Ser Leu Arg Leu Ser Cys Ala Ala Ser Gly Arg Thr Ile Asp Asn Tyr
            20                  25                  30

Ala Met Ala Trp Ser Arg Gln Ala Pro Gly Lys Asp Arg Glu Phe Val
        35                  40                  45

Ala Thr Ile Asp Trp Gly Asp Gly Ala Arg Tyr Ala Asn Ser Val
    50                  55                  60

Lys Gly Arg Phe Thr Ile Ser Arg Asp Asn Ala Lys Gly Thr Met Tyr
65                  70                  75                  80

Leu Gln Met Asn Leu Glu Pro Glu Asp Thr Ala Val Tyr Ser Cys
            85                  90                  95

Ala Met Ala Arg Gln Ser Arg Val Asn Leu Asp Val Ala Arg Tyr Asp
        100                 105                 110

Tyr Trp Gly Gln Gly Thr Gln Val Thr Val Ser Ser
        115                 120

<210> SEQ ID NO 26
<211> LENGTH: 124
<212> TYPE: PRT
<213> ORGANISM: Artificial Sequence
<220> FEATURE:
<223> OTHER INFORMATION: IGF1R-5-H2

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
            85                  90                  95

Ala Met Ala Arg Gln Ser Arg Val Asn Leu Asp Val Ala Arg Tyr Asp
        100                 105                 110

Tyr Trp Gly Gln Gly Thr Leu Val Thr Val Ser Ser
        115                 120

<210> SEQ ID NO 27
<211> LENGTH: 174
<212> TYPE: PRT
<213> ORGANISM: Artificial Sequence
<220> FEATURE:
<223> OTHER INFORMATION: PK-4

<400> SEQUENCE: 27

Ser Gly Lys Thr Glu Tyr Met Ala Phe Pro Lys Pro Phe Glu Ser Ser
1               5                   10                  15

Ser Ser Ile Gly Ala Glu Lys Pro Arg Asn Lys Lys Leu Pro Glu Glu
            20                  25                  30

Glu Val Glu Ser Ser Arg Thr Pro Trp Leu Tyr Glu Gln Gly Glu
        35                  40                  45

Val Glu Lys Pro Phe Ile Lys Thr Gly Phe Ser Val Ser Val Glu Lys
    50                  55                  60

```
Ser Thr Ser Ser Asn Arg Lys Asn Gln Leu Asp Thr Asn Gly Arg Arg
 65                  70                  75                  80

Arg Gln Phe Asp Glu Glu Ser Leu Glu Ser Phe Ser Met Pro Asp
             85                  90                  95

Pro Val Asp Pro Thr Thr Val Thr Lys Thr Phe Lys Thr Arg Lys Ala
                100                 105                 110

Ser Ala Gln Ala Ser Leu Ala Ser Lys Asp Lys Thr Pro Lys Ser Lys
            115                 120                 125

Ser Lys Lys Arg Asn Ser Thr Gln Leu Lys Ser Arg Val Lys Asn Ile
130                 135                 140

Thr His Ala Arg Arg Ile Leu Gln Gln Ser Asn Arg Asn Ala Cys Asn
145                 150                 155                 160

Glu Ala Pro Glu Thr Gly Ser Asp Phe Ser Met Phe Glu Ala
                165                 170
```

<210> SEQ ID NO 28
<211> LENGTH: 40
<212> TYPE: PRT
<213> ORGANISM: Artificial Sequence
<220> FEATURE:
<223> OTHER INFORMATION: P4 peptide

<400> SEQUENCE: 28

```
Phe Ser Ser Met Pro Asp Pro Val Asp Pro Thr Thr Val Thr Lys Thr
1               5                   10                  15

Phe Lys Thr Arg Lys Ala Ser Ala Gln Ala Ser Leu Ala Ser Lys Asp
            20                  25                  30

Lys Thr Pro Lys Ser Lys Ser Lys
        35                  40
```

<210> SEQ ID NO 29
<211> LENGTH: 40
<212> TYPE: PRT
<213> ORGANISM: Artificial Sequence
<220> FEATURE:
<223> OTHER INFORMATION: P5 peptide

<400> SEQUENCE: 29

```
Lys Asp Lys Thr Pro Lys Ser Lys Ser Lys Arg Asn Ser Thr Gln
1               5                   10                  15

Leu Lys Ser Arg Val Lys Asn Ile Thr His Ala Arg Arg Ile Leu Gln
            20                  25                  30

Gln Ser Asn Arg Asn Ala Cys Asn
        35                  40
```

<210> SEQ ID NO 30
<211> LENGTH: 40
<212> TYPE: PRT
<213> ORGANISM: Artificial Sequence
<220> FEATURE:
<223> OTHER INFORMATION: P4-5 peptide (ABP)

<400> SEQUENCE: 30

```
Lys Thr Phe Lys Thr Arg Lys Ala Ser Ala Gln Ala Ser Leu Ala Ser
1               5                   10                  15

Lys Asp Lys Thr Pro Lys Ser Lys Ser Lys Arg Asn Ser Thr Gln
            20                  25                  30

Leu Lys Ser Arg Val Lys Asn Ile
        35                  40
```

<210> SEQ ID NO 31
<211> LENGTH: 40
<212> TYPE: PRT
<213> ORGANISM: Artificial Sequence
<220> FEATURE:
<223> OTHER INFORMATION: ABP consensus
<220> FEATURE:
<221> NAME/KEY: misc_feature
<222> LOCATION: (1)..(1)
<223> OTHER INFORMATION: where X is G or A
<220> FEATURE:
<221> NAME/KEY: misc_feature
<222> LOCATION: (4)..(4)
<223> OTHER INFORMATION: where X is G or V
<220> FEATURE:
<221> NAME/KEY: misc_feature
<222> LOCATION: (6)..(6)
<223> OTHER INFORMATION: where X is G or A
<220> FEATURE:
<221> NAME/KEY: misc_feature
<222> LOCATION: (7)..(7)
<223> OTHER INFORMATION: where X is G or A
<220> FEATURE:
<221> NAME/KEY: misc_feature
<222> LOCATION: (28)..(28)
<223> OTHER INFORMATION: where X is G or V
<220> FEATURE:
<221> NAME/KEY: misc_feature
<222> LOCATION: (29)..(29)
<223> OTHER INFORMATION: where X is G or V
<220> FEATURE:
<221> NAME/KEY: misc_feature
<222> LOCATION: (34)..(34)
<223> OTHER INFORMATION: where X is G or V
<220> FEATURE:
<221> NAME/KEY: misc_feature
<222> LOCATION: (36)..(36)
<223> OTHER INFORMATION: where X is G or A
<220> FEATURE:
<221> NAME/KEY: misc_feature
<222> LOCATION: (38)..(38)
<223> OTHER INFORMATION: where X is G or A

<400> SEQUENCE: 31

Xaa Thr Phe Xaa Thr Xaa Xaa Ala Ser Ala Gln Ala Ser Leu Ala Ser
1               5                   10                  15

Lys Asp Lys Thr Pro Lys Ser Lys Ser Lys Lys Xaa Xaa Ser Thr Gln
            20                  25                  30

Leu Xaa Ser Xaa Val Xaa Asn Ile
        35                  40

<210> SEQ ID NO 32
<211> LENGTH: 40
<212> TYPE: PRT
<213> ORGANISM: Artificial Sequence
<220> FEATURE:
<223> OTHER INFORMATION: [ABP(G)]

<400> SEQUENCE: 32

Lys Thr Phe Lys Thr Arg Lys Ala Ser Ala Gln Ala Ser Leu Ala Ser
1               5                   10                  15

Lys Asp Lys Thr Pro Lys Ser Lys Ser Lys Lys Arg Gly Ser Thr Gln
            20                  25                  30

Leu Lys Ser Arg Val Lys Asn Ile
        35                  40

<210> SEQ ID NO 33
<211> LENGTH: 40
<212> TYPE: PRT
<213> ORGANISM: Artificial Sequence

<220> FEATURE:
<223> OTHER INFORMATION: [ABP(GG)]

<400> SEQUENCE: 33

Lys Thr Phe Lys Thr Arg Lys Ala Ser Ala Gln Ala Ser Leu Ala Ser
1               5                   10                  15

Lys Asp Lys Thr Pro Lys Ser Lys Ser Lys Lys Gly Gly Ser Thr Gln
            20                  25                  30

Leu Lys Ser Arg Val Lys Asn Ile
        35                  40

<210> SEQ ID NO 34
<211> LENGTH: 40
<212> TYPE: PRT
<213> ORGANISM: Artificial Sequence
<220> FEATURE:
<223> OTHER INFORMATION: [ABP(RG-G)]

<400> SEQUENCE: 34

Lys Thr Phe Lys Thr Arg Gly Ala Ser Ala Gln Ala Ser Leu Ala Ser
1               5                   10                  15

Lys Asp Lys Thr Pro Lys Ser Lys Ser Lys Lys Arg Gly Ser Thr Gln
            20                  25                  30

Leu Lys Ser Arg Val Lys Asn Ile
        35                  40

<210> SEQ ID NO 35
<211> LENGTH: 40
<212> TYPE: PRT
<213> ORGANISM: Artificial Sequence
<220> FEATURE:
<223> OTHER INFORMATION: [ABP(GG-G)]

<400> SEQUENCE: 35

Lys Thr Phe Lys Thr Gly Gly Ala Ser Ala Gln Ala Ser Leu Ala Ser
1               5                   10                  15

Lys Asp Lys Thr Pro Lys Ser Lys Ser Lys Lys Arg Gly Ser Thr Gln
            20                  25                  30

Leu Lys Ser Arg Val Lys Asn Ile
        35                  40

<210> SEQ ID NO 36
<211> LENGTH: 40
<212> TYPE: PRT
<213> ORGANISM: Artificial Sequence
<220> FEATURE:
<223> OTHER INFORMATION: [ABP(6G)]

<400> SEQUENCE: 36

Gly Thr Phe Gly Thr Gly Gly Ala Ser Ala Gln Ala Ser Leu Ala Ser
1               5                   10                  15

Lys Asp Lys Thr Pro Lys Ser Lys Ser Lys Lys Gly Gly Ser Thr Gln
            20                  25                  30

Leu Lys Ser Arg Val Lys Asn Ile
        35                  40

<210> SEQ ID NO 37
<211> LENGTH: 35
<212> TYPE: PRT
<213> ORGANISM: Artificial Sequence
<220> FEATURE:
<223> OTHER INFORMATION: [ABP(GGspv)]

```
<400> SEQUENCE: 37

Lys Thr Phe Lys Thr Arg Lys Ala Ser Ala Gln Ala Ser Leu Ala Ser
1               5                   10                  15

Lys Asp Lys Thr Pro Lys Ser Lys Ser Lys Lys Gly Gly Ser Thr Val
            20                  25                  30

Lys Asn Ile
        35

<210> SEQ ID NO 38
<211> LENGTH: 29
<212> TYPE: PRT
<213> ORGANISM: Artificial Sequence
<220> FEATURE:
<223> OTHER INFORMATION: [ABP(trc)]

<400> SEQUENCE: 38

Lys Thr Phe Lys Thr Arg Lys Ala Ser Ala Gln Ala Ser Leu Ala Ser
1               5                   10                  15

Lys Asp Lys Thr Pro Lys Ser Lys Ser Lys Lys Arg Gly
            20                  25

<210> SEQ ID NO 39
<211> LENGTH: 234
<212> TYPE: PRT
<213> ORGANISM: Artificial Sequence
<220> FEATURE:
<223> OTHER INFORMATION: Mouse Fc2a

<400> SEQUENCE: 39

Ala Ser Glu Pro Arg Gly Pro Thr Ile Lys Pro Cys Pro Pro Cys Lys
1               5                   10                  15

Cys Pro Ala Pro Asn Leu Leu Gly Gly Pro Ser Val Phe Ile Phe Pro
            20                  25                  30

Pro Lys Ile Lys Asp Val Leu Met Ile Ser Leu Ser Pro Ile Val Thr
            35                  40                  45

Cys Val Val Val Asp Val Ser Glu Asp Asp Pro Asp Val Gln Ile Ser
    50                  55                  60

Trp Phe Val Asn Asn Val Glu Val His Thr Ala Gln Thr Gln Thr His
65                  70                  75                  80

Arg Glu Asp Tyr Asn Ser Thr Leu Arg Val Val Ser Ala Leu Pro Ile
                85                  90                  95

Gln His Gln Asp Trp Met Ser Gly Lys Glu Phe Lys Cys Lys Val Asn
            100                 105                 110

Asn Lys Asp Leu Pro Ala Pro Ile Glu Arg Thr Ile Ser Lys Pro Lys
        115                 120                 125

Gly Ser Val Arg Ala Pro Gln Val Tyr Val Leu Pro Pro Pro Glu Glu
    130                 135                 140

Glu Met Thr Lys Lys Gln Val Thr Leu Thr Cys Met Val Thr Asp Phe
145                 150                 155                 160

Met Pro Glu Asp Ile Tyr Val Glu Trp Thr Asn Asn Gly Lys Thr Glu
                165                 170                 175

Leu Asn Tyr Lys Asn Thr Glu Pro Val Leu Asp Ser Asp Gly Ser Tyr
            180                 185                 190

Phe Met Tyr Ser Lys Leu Arg Val Glu Lys Lys Asn Trp Val Glu Arg
        195                 200                 205

Asn Ser Tyr Ser Cys Ser Val Val His Glu Gly Leu His Asn His His
    210                 215                 220
```

-continued

```
Thr Thr Lys Ser Phe Ser Arg Thr Pro Gly
225                 230

<210> SEQ ID NO 40
<211> LENGTH: 232
<212> TYPE: PRT
<213> ORGANISM: Artificial Sequence
<220> FEATURE:
<223> OTHER INFORMATION: Human Fc1x7

<400> SEQUENCE: 40

Ala Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Gly Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly
225                 230

<210> SEQ ID NO 41
<211> LENGTH: 232
<212> TYPE: PRT
<213> ORGANISM: Artificial Sequence
<220> FEATURE:
<223> OTHER INFORMATION: Human Fc1X0

<400> SEQUENCE: 41

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Gly Pro Glu Val Lys Phe Asn Trp His
50                  55                  60
```

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Gly Leu His Asn His Tyr Thr Gln
    210                 215                 220

Lys Ser Leu Ser Leu Ser Pro Gly
225                 230

<210> SEQ ID NO 42
<211> LENGTH: 407
<212> TYPE: PRT
<213> ORGANISM: Artificial Sequence
<220> FEATURE:
<223> OTHER INFORMATION: FC5-mFc2a-ABP

<400> SEQUENCE: 42

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
            85                  90                  95

Ala Ala Gly Ser Thr Ser Thr Ala Thr Pro Leu Arg Val Asp Tyr Trp
        100                 105                 110

Gly Lys Gly Thr Gln Val Thr Val Ser Ser Ala Ser Glu Pro Arg Gly
    115                 120                 125

Pro Thr Ile Lys Pro Cys Pro Pro Cys Lys Cys Pro Ala Pro Asn Leu
130                 135                 140

Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Val Asp Val
            165                 170                 175

Ser Glu Asp Asp Pro Asp Val Gln Ile Ser Trp Phe Val Asn Asn Val
        180                 185                 190

```
Glu Val His Thr Ala Gln Thr Gln Thr His Arg Glu Asp Tyr Asn Ser
            195                 200                 205

Thr Leu Arg Val Val Ser Ala Leu Pro Ile Gln His Gln Asp Trp Met
        210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
                245                 250                 255

Gln Val Tyr Val Leu Pro Pro Glu Glu Met Thr Lys Lys Gln
            260                 265                 270

Val Thr Leu Thr Cys Met Val Thr Asp Phe Met Pro Glu Asp Ile Tyr
                275                 280                 285

Val Glu Trp Thr Asn Asn Gly Lys Thr Glu Leu Asn Tyr Lys Asn Thr
        290                 295                 300

Glu Pro Val Leu Asp Ser Asp Gly Ser Tyr Phe Met Tyr Ser Lys Leu
305                 310                 315                 320

Arg Val Glu Lys Lys Asn Trp Val Glu Arg Asn Ser Tyr Ser Cys Ser
                325                 330                 335

Val Val His Glu Gly Leu His Asn His His Thr Thr Lys Ser Phe Ser
            340                 345                 350

Arg Thr Pro Gly Thr Gly Gly Gly Ser Gly Gly Gly Ser Lys
                355                 360                 365

Thr Phe Lys Thr Arg Lys Ala Ser Ala Gln Ala Ser Leu Ala Ser Lys
        370                 375                 380

Asp Lys Thr Pro Lys Ser Lys Ser Lys Arg Asn Ser Thr Gln Leu
385                 390                 395                 400

Lys Ser Arg Val Lys Asn Ile
                405

<210> SEQ ID NO 43
<211> LENGTH: 407
<212> TYPE: PRT
<213> ORGANISM: Artificial Sequence
<220> FEATURE:
<223> OTHER INFORMATION: FC5-H3-mFc2a-ABP

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser Ala Ser Glu Pro Arg Gly
        115                 120                 125

Pro Thr Ile Lys Pro Cys Pro Pro Cys Lys Cys Pro Ala Pro Asn Leu
    130                 135                 140
```

-continued

```
Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Val Asp Val
                165                 170                 175

Ser Glu Asp Asp Pro Asp Val Gln Ile Ser Trp Phe Val Asn Asn Val
            180                 185                 190

Glu Val His Thr Ala Gln Thr Gln Thr His Arg Glu Asp Tyr Asn Ser
        195                 200                 205

Thr Leu Arg Val Val Ser Ala Leu Pro Ile Gln His Gln Asp Trp Met
    210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
                245                 250                 255

Gln Val Tyr Val Leu Pro Pro Glu Glu Glu Met Thr Lys Lys Gln
            260                 265                 270

Val Thr Leu Thr Cys Met Val Thr Asp Phe Met Pro Glu Asp Ile Tyr
        275                 280                 285

Val Glu Trp Thr Asn Asn Gly Lys Thr Glu Leu Asn Tyr Lys Asn Thr
    290                 295                 300

Glu Pro Val Leu Asp Ser Asp Gly Ser Tyr Phe Met Tyr Ser Lys Leu
305                 310                 315                 320

Arg Val Glu Lys Lys Asn Trp Val Glu Arg Asn Ser Tyr Ser Cys Ser
                325                 330                 335

Val Val His Glu Gly Leu His Asn His His Thr Thr Lys Ser Phe Ser
            340                 345                 350

Arg Thr Pro Gly Thr Gly Gly Gly Ser Gly Gly Gly Ser Lys
        355                 360                 365

Thr Phe Lys Thr Arg Lys Ala Ser Ala Gln Ala Ser Leu Ala Ser Lys
    370                 375                 380

Asp Lys Thr Pro Lys Ser Lys Ser Lys Arg Asn Ser Thr Gln Leu
385                 390                 395                 400

Lys Ser Arg Val Lys Asn Ile
                405
```

<210> SEQ ID NO 44
<211> LENGTH: 404
<212> TYPE: PRT
<213> ORGANISM: Artificial Sequence
<220> FEATURE:
<223> OTHER INFORMATION: FC5-H3-hFc1X7-ABP

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95
```

Ala Ala Gly Ser Thr Ser Thr Ala Thr Pro Leu Arg Val Asp Tyr Trp
                100                 105                 110

Gly Gln Gly Thr Leu Val Thr Val Ser Ser Ala Glu Pro Lys Ser Ser
            115                 120                 125

Asp Lys Thr His Thr Cys Pro Pro Cys Pro Ala Pro Glu Leu Leu Gly
130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Gly Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Thr Gly Gly Gly Ser Gly Gly Gly Ser Lys Thr Phe Lys
        355                 360                 365

Thr Arg Lys Ala Ser Ala Gln Ala Ser Leu Ala Ser Lys Asp Lys Thr
    370                 375                 380

Pro Lys Ser Lys Ser Lys Arg Asn Ser Thr Gln Leu Lys Ser Arg
385                 390                 395                 400

Val Lys Asn Ile

<210> SEQ ID NO 45
<211> LENGTH: 404
<212> TYPE: PRT
<213> ORGANISM: Artificial Sequence
<220> FEATURE:
<223> OTHER INFORMATION: FC5-H3-hFc1X7-ABP(G)

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50              55                  60

Lys Gly Arg Phe Thr Ile Ser Arg Asp Asn Ser Lys Asn Thr Val Tyr
 65              70                  75                  80

Leu Gln Met Asn Ser Leu Arg Ala Glu Asp Thr Ala Val Tyr Tyr Cys
             85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser Ala Glu Pro Lys Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Gly Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Thr Gly Gly Gly Ser Gly Gly Gly Ser Lys Thr Phe Lys
        355                 360                 365

Thr Arg Lys Ala Ser Ala Gln Ala Ser Leu Ala Ser Lys Asp Lys Thr
    370                 375                 380

Pro Lys Ser Lys Ser Lys Arg Gly Ser Thr Gln Leu Lys Ser Arg
385                 390                 395                 400

Val Lys Asn Ile

<210> SEQ ID NO 46
<211> LENGTH: 404
<212> TYPE: PRT
<213> ORGANISM: Artificial Sequence
<220> FEATURE:
<223> OTHER INFORMATION: FC5-H3-hFc1X7-ABP(GG-G)

<400> SEQUENCE: 46

Glu Val Gln Leu Val Glu Ser Gly Gly Gly Leu Val Gln Pro Gly Gly

```
1               5                   10                  15
Ser Leu Arg Leu Ser Cys Ala Ala Ser Gly Phe Lys Ile Thr His Tyr
            20                  25                  30
Thr Met Gly Trp Phe Arg Gln Ala Pro Gly Lys Gly Leu Glu Phe Val
            35                  40                  45
Ser Arg Ile Thr Trp Gly Gly Asp Asn Thr Phe Tyr Ser Asn Ser Val
            50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Val Tyr Tyr Cys
            85                  90                  95
Ala Ala Gly Ser Thr Ser Thr Ala Thr Pro Leu Arg Val Asp Tyr Trp
            100                 105                 110
Gly Gln Gly Thr Leu Val Thr Val Ser Ser Ala Glu Pro Lys Ser Ser
            115                 120                 125
Asp Lys Thr His Thr Cys Pro Pro Cys Pro Ala Pro Glu Leu Leu Gly
            130                 135                 140
Gly Pro Ser Val Phe Leu Phe Pro Pro Lys Pro Lys Asp Thr Leu Met
145                 150                 155                 160
Ile Ser Arg Thr Pro Glu Val Thr Cys Val Val Val Asp Val Ser His
            165                 170                 175
Glu Gly Pro Glu Val Lys Phe Asn Trp Tyr Val Asp Gly Val Glu Val
            180                 185                 190
His Asn Ala Lys Thr Lys Pro Arg Glu Glu Gln Tyr Asn Ser Thr Tyr
            195                 200                 205
Arg Val Val Ser Val Leu Thr Val Leu His Gln Asp Trp Leu Asn Gly
            210                 215                 220
Lys Glu Tyr Lys Cys Lys Val Ser Asn Lys Ala Leu Pro Ala Pro Ile
225                 230                 235                 240
Glu Lys Thr Ile Ser Lys Ala Lys Gly Gln Pro Arg Glu Pro Gln Val
            245                 250                 255
Tyr Thr Leu Pro Pro Ser Arg Asp Glu Leu Thr Lys Asn Gln Val Ser
            260                 265                 270
Leu Thr Cys Leu Val Lys Gly Phe Tyr Pro Ser Asp Ile Ala Val Glu
            275                 280                 285
Trp Glu Ser Asn Gly Gln Pro Glu Asn Asn Tyr Lys Thr Thr Pro Pro
            290                 295                 300
Val Leu Asp Ser Asp Gly Ser Phe Phe Leu Tyr Ser Lys Leu Thr Val
305                 310                 315                 320
Asp Lys Ser Arg Trp Gln Gln Gly Asn Val Phe Ser Cys Ser Val Met
            325                 330                 335
His Glu Ala Leu His Asn His Tyr Thr Gln Lys Ser Leu Ser Leu Ser
            340                 345                 350
Pro Gly Thr Gly Gly Gly Ser Gly Gly Gly Gly Ser Lys Thr Phe Lys
            355                 360                 365
Thr Gly Gly Ala Ser Ala Gln Ala Ser Leu Ala Ser Lys Asp Lys Thr
            370                 375                 380
Pro Lys Ser Lys Ser Lys Lys Arg Gly Ser Thr Gln Leu Lys Ser Arg
385                 390                 395                 400
Val Lys Asn Ile

<210> SEQ ID NO 47
<211> LENGTH: 405
```

<212> TYPE: PRT
<213> ORGANISM: Artificial Sequence
<220> FEATURE:
<223> OTHER INFORMATION: FC5-H3-hFc1X7-ABP(6G)

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser Ala Glu Pro Lys Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Gly Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Thr Gly Gly Gly Ser Gly Gly Gly Ser Gly Thr Phe
        355                 360                 365

Gly Thr Gly Gly Ala Ser Ala Gln Ala Ser Leu Ala Ser Lys Asp Lys
370                 375                 380
```

Thr Pro Lys Ser Lys Ser Lys Lys Gly Gly Ser Thr Gln Leu Lys Ser
385                 390                 395                 400

Arg Val Lys Asn Ile
            405

<210> SEQ ID NO 48
<211> LENGTH: 414
<212> TYPE: PRT
<213> ORGANISM: Artificial Sequence
<220> FEATURE:
<223> OTHER INFORMATION: FC5(H3)-ABP(GG-G)- hFc1X7

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser Gly Gly Gly Gly Ser Gly
        115                 120                 125

Gly Gly Gly Ser Lys Thr Phe Lys Thr Gly Gly Ala Ser Ala Gln Ala
    130                 135                 140

Ser Leu Ala Ser Lys Asp Lys Thr Pro Lys Ser Lys Ser Lys Lys Arg
145                 150                 155                 160

Gly Ser Thr Gln Leu Lys Ser Arg Val Lys Asn Ile Gly Gly Gly Gly
                165                 170                 175

Ser Gly Gly Gly Gly Ser Ala Glu Pro Lys Ser Ser Asp Lys Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Gly Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Asp Glu Leu Thr Lys Asn Gln Val Ser Leu Thr Cys Leu
                325                 330                 335

```
Val Lys Gly Phe Tyr Pro Ser Asp Ile Ala Val Glu Trp Glu Ser Asn
              340                 345                 350

Gly Gln Pro Glu Asn Asn Tyr Lys Thr Thr Pro Pro Val Leu Asp Ser
          355                 360                 365

Asp Gly Ser Phe Phe Leu Tyr Ser Lys Leu Thr Val Asp Lys Ser Arg
      370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly
              405                 410

<210> SEQ ID NO 49
<211> LENGTH: 404
<212> TYPE: PRT
<213> ORGANISM: Artificial Sequence
<220> FEATURE:
<223> OTHER INFORMATION: FC5-H3-hFc1X0-ABP(GG-G)

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Gly Leu Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Gly Ser Thr Ser Thr Ala Thr Pro Leu Arg Val Asp Tyr Trp
            100                 105                 110

Gly Gln Gly Thr Leu Val Thr Val Ser Ser Ala Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Gly Pro Glu Val Lys Phe Asn Trp His Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285
```

```
Trp Glu Ser Asn Gly Gln Pro Glu Asn Asn Tyr Lys Thr Thr Pro Pro
        290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Gly Leu His Asn His Tyr Thr Gln Lys Ser Leu Ser Leu Ser
            340                 345                 350

Pro Gly Thr Gly Gly Ser Gly Gly Gly Ser Lys Thr Phe Lys
        355                 360                 365

Thr Gly Gly Ala Ser Ala Gln Ala Ser Leu Ala Ser Lys Asp Lys Thr
    370                 375                 380

Pro Lys Ser Lys Ser Lys Lys Arg Gly Ser Thr Gln Leu Lys Ser Arg
385                 390                 395                 400

Val Lys Asn Ile

<210> SEQ ID NO 50
<211> LENGTH: 406
<212> TYPE: PRT
<213> ORGANISM: Artificial Sequence
<220> FEATURE:
<223> OTHER INFORMATION: IGF1R5-H2-hFc1X7-ABP(GG-G)

<400> SEQUENCE: 50

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ile Asp Asn Tyr
            20                  25                  30

Ala Met Ala Trp Val Arg Gln Ala Pro Gly Lys Gly Leu Glu Trp Val
        35                  40                  45

Ala Thr Ile Asp Trp Gly Asp Gly Thr Arg Tyr Ala Asn Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Met Ala Arg Gln Ser Arg Val Asn Leu Asp Val Ala Arg Tyr Asp
            100                 105                 110

Tyr Trp Gly Gln Gly Thr Leu Val Thr Val Ser Ser Ala Glu Pro Lys
        115                 120                 125

Ser Ser Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Gly Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
```

```
                    245                 250                 255
Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Thr Gly Gly Ser Gly Gly Gly Ser Lys Thr
        355                 360                 365

Phe Lys Thr Gly Gly Ala Ser Ala Gln Ala Ser Leu Ala Ser Lys Asp
    370                 375                 380

Lys Thr Pro Lys Ser Lys Ser Lys Arg Gly Ser Thr Gln Leu Lys
385                 390                 395                 400

Ser Arg Val Lys Asn Ile
            405

<210> SEQ ID NO 51
<211> LENGTH: 405
<212> TYPE: PRT
<213> ORGANISM: Artificial Sequence
<220> FEATURE:
<223> OTHER INFORMATION: ABP(GG-G)-hFc1X7- IGF1R5-H2

<400> SEQUENCE: 51

Lys Thr Phe Lys Thr Gly Gly Ala Ser Ala Gln Ala Ser Leu Ala Ser
1               5                   10                  15

Lys Asp Lys Thr Pro Lys Ser Lys Ser Lys Arg Gly Ser Thr Gln
            20                  25                  30

Leu Lys Ser Arg Val Lys Asn Ile Gly Gly Gly Ser Gly Gly Gly Gly
        35                  40                  45

Ser Ala Glu Pro Lys Ser Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Gly Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
```

```
                195                 200                 205
Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly Gln Val Gln Leu Val Glu Ser
                275                 280                 285

Gly Gly Gly Leu Val Gln Pro Gly Gly Ser Leu Arg Leu Ser Cys Ala
290                 295                 300

Ala Ser Gly Arg Thr Ile Asp Asn Tyr Ala Met Ala Trp Val Arg Gln
305                 310                 315                 320

Ala Pro Gly Lys Gly Leu Glu Trp Val Ala Thr Ile Asp Trp Gly Asp
                325                 330                 335

Gly Gly Thr Arg Tyr Ala Asn Ser Val Lys Gly Arg Phe Thr Ile Ser
                340                 345                 350

Arg Asp Asn Ser Lys Asn Thr Met Tyr Leu Gln Met Asn Ser Leu Arg
                355                 360                 365

Ala Glu Asp Thr Ala Val Tyr Tyr Cys Ala Met Ala Arg Gln Ser Arg
370                 375                 380

Val Asn Leu Asp Val Ala Arg Tyr Asp Tyr Trp Gly Gln Gly Thr Leu
385                 390                 395                 400

Val Thr Val Ser Ser
                405

<210> SEQ ID NO 52
<211> LENGTH: 414
<212> TYPE: PRT
<213> ORGANISM: Artificial Sequence
<220> FEATURE:
<223> OTHER INFORMATION: hFc1X7- ABP(GG-G)- IGF1R5-H2

<400> SEQUENCE: 52

Ala Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Gly Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
```

```
                145                 150                 155                 160
Ser Asp Ile Ala Val Glu Trp Glu Ser Asn Gly Gln Pro Glu Asn Asn
                    165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Gly Gly Gly Ser Gly Gly Gly Gly
225                 230                 235                 240

Ser Lys Thr Phe Lys Thr Gly Gly Ala Ser Gln Ala Ser Leu Ala
                245                 250                 255

Ser Lys Asp Lys Thr Pro Lys Ser Lys Ser Lys Arg Gly Ser Thr
            260                 265                 270

Gln Leu Lys Ser Arg Val Lys Asn Ile Gly Gly Ser Gly Gly Gly
        275                 280                 285

Gly Ser Gln Val Gln Leu Val Glu Ser Gly Gly Leu Val Gln Pro
    290                 295                 300

Gly Gly Ser Leu Arg Leu Ser Cys Ala Ala Ser Gly Arg Thr Ile Asp
305                 310                 315                 320

Asn Tyr Ala Met Ala Trp Val Arg Gln Ala Pro Gly Lys Gly Leu Glu
                325                 330                 335

Trp Val Ala Thr Ile Asp Trp Gly Asp Gly Gly Thr Arg Tyr Ala Asn
            340                 345                 350

Ser Val Lys Gly Arg Phe Thr Ile Ser Arg Asp Asn Ser Lys Asn Thr
        355                 360                 365

Met Tyr Leu Gln Met Asn Ser Leu Arg Ala Glu Asp Thr Ala Val Tyr
    370                 375                 380

Tyr Cys Ala Met Ala Arg Gln Ser Arg Val Asn Leu Asp Val Ala Arg
385                 390                 395                 400

Tyr Asp Tyr Trp Gly Gln Gly Thr Leu Val Thr Val Ser Ser
                405                 410

<210> SEQ ID NO 53
<211> LENGTH: 405
<212> TYPE: PRT
<213> ORGANISM: Artificial Sequence
<220> FEATURE:
<223> OTHER INFORMATION: FC5-H3-hFc1X7-L(consensus)-ABP(6G)
<220> FEATURE:
<221> NAME/KEY: misc_feature
<222> LOCATION: (357)..(357)
<223> OTHER INFORMATION: where X is A or G
<220> FEATURE:
<221> NAME/KEY: misc_feature
<222> LOCATION: (359)..(359)
<223> OTHER INFORMATION: where X is A or G
<220> FEATURE:
<221> NAME/KEY: misc_feature
<222> LOCATION: (360)..(360)
<223> OTHER INFORMATION: where X is S or T
<220> FEATURE:
<221> NAME/KEY: misc_feature
<222> LOCATION: (362)..(362)
<223> OTHER INFORMATION: where X is G or V
<220> FEATURE:
<221> NAME/KEY: misc_feature
<222> LOCATION: (363)..(363)
<223> OTHER INFORMATION: where X is G, A or V
<220> FEATURE:
<221> NAME/KEY: misc_feature
```

<222> LOCATION: (365)..(365)
<223> OTHER INFORMATION: where X is S or T

<400> SEQUENCE: 53

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly | Ser | Leu | Arg | Leu | Ser | Cys | Ala | Ala | Ser | Gly | Phe | Lys | Ile | Thr |
| | | | 20 | | | | | 25 | | | | | 30 | |
| His | Tyr | Thr | Met | Gly | Trp | Phe | Arg | Gln | Ala | Pro | Gly | Lys | Gly | Leu |
| | | | 35 | | | | | 40 | | | | | 45 | |
| Glu | Phe | Val | Ser | Arg | Ile | Thr | Trp | Gly | Gly | Asp | Asn | Thr | Phe | Tyr |
| | | | 50 | | | | | 55 | | | | | 60 | |
| Ser | Asn | Ser | Val | Lys | Gly | Arg | Phe | Thr | Ile | Ser | Arg | Asp | Asn | Ser |
| 65 | | | | | 70 | | | | | 75 | | | | |
| Lys | Asn | Thr | Val | Tyr | Leu | Gln | Met | Asn | Ser | Leu | Arg | Ala | Glu | Asp |
| | | | 80 | | | | | 85 | | | | | 90 | |
| Thr | Ala | Val | Tyr | Tyr | Cys | Ala | Ala | Gly | Ser | Thr | Ser | Thr | Ala | Thr |
| | | | 95 | | | | | 100 | | | | | 105 | |
| Pro | Leu | Arg | Val | Asp | Tyr | Trp | Gly | Gln | Gly | Thr | Leu | Val | Thr | Val |
| | | | 110 | | | | | 115 | | | | | 120 | |
| Ser | Ser | Ala | Glu | Pro | Lys | Ser | Ser | Asp | Lys | Thr | His | Thr | Cys | Pro |
| | | | 125 | | | | | 130 | | | | | 135 | |
| Pro | Cys | Pro | Ala | Pro | Glu | Leu | Leu | Gly | Gly | Pro | Ser | Val | Phe | Leu |
| | | | 140 | | | | | 145 | | | | | 150 | |
| Phe | Pro | Pro | Lys | Pro | Lys | Asp | Thr | Leu | Met | Ile | Ser | Arg | Thr | Pro |
| | | | 155 | | | | | 160 | | | | | 165 | |
| Glu | Val | Thr | Cys | Val | Val | Val | Asp | Val | Ser | His | Glu | Gly | Pro | Glu |
| | | | 170 | | | | | 175 | | | | | 180 | |
| Val | Lys | Phe | Asn | Trp | Tyr | Val | Asp | Gly | Val | Glu | Val | His | Asn | Ala |
| | | | 185 | | | | | 190 | | | | | 195 | |
| Lys | Thr | Lys | Pro | Arg | Glu | Glu | Gln | Tyr | Asn | Ser | Thr | Tyr | Arg | Val |
| | | | 200 | | | | | 205 | | | | | 210 | |
| Val | Ser | Val | Leu | Thr | Val | Leu | His | Gln | Asp | Trp | Leu | Asn | Gly | Lys |
| | | | 215 | | | | | 220 | | | | | 225 | |
| Glu | Tyr | Lys | Cys | Lys | Val | Ser | Asn | Lys | Ala | Leu | Pro | Ala | Pro | Ile |
| | | | 230 | | | | | 235 | | | | | 240 | |
| Glu | Lys | Thr | Ile | Ser | Lys | Ala | Lys | Gly | Gln | Pro | Arg | Glu | Pro | Gln |
| | | | 245 | | | | | 250 | | | | | 255 | |
| Val | Tyr | Thr | Leu | Pro | Pro | Ser | Arg | Asp | Glu | Leu | Thr | Lys | Asn | Gln |
| | | | 260 | | | | | 265 | | | | | 270 | |
| Val | Ser | Leu | Thr | Cys | Leu | Val | Lys | Gly | Phe | Tyr | Pro | Ser | Asp | Ile |
| | | | 275 | | | | | 280 | | | | | 285 | |
| Ala | Val | Glu | Trp | Glu | Ser | Asn | Gly | Gln | Pro | Glu | Asn | Asn | Tyr | Lys |
| | | | 290 | | | | | 295 | | | | | 300 | |
| Thr | Thr | Pro | Pro | Val | Leu | Asp | Ser | Asp | Gly | Ser | Phe | Phe | Leu | Tyr |
| 305 | | | | | 310 | | | | | 315 | | | | |
| Ser | Lys | Leu | Thr | Val | Asp | Lys | Ser | Arg | Trp | Gln | Gln | Gly | Asn | Val |
| | | | 320 | | | | | 325 | | | | | 330 | |
| Phe | Ser | Cys | Ser | Val | Met | His | Glu | Ala | Leu | His | Asn | His | Tyr | Thr |
| | | | 335 | | | | | 340 | | | | | 345 | |
| Gln | Lys | Ser | Leu | Ser | Leu | Ser | Pro | Gly | Thr | Gly | Xaa | Gly | Xaa | Xaa |
| | | | 350 | | | | | 355 | | | | | 360 | |
| Gly | Xaa | Xaa | Gly | Xaa | Gly | Thr | Phe | Gly | Thr | Gly | Gly | Ala | Ser | Ala |
| | | | 365 | | | | | 370 | | | | | 375 | |
| Gln | Ala | Ser | Leu | Ala | Ser | Lys | Asp | Lys | Thr | Pro | Lys | Ser | Lys | Ser |
| | | | 380 | | | | | 385 | | | | | 390 | |
| Lys | Lys | Gly | Ser | Thr | Gln | Leu | Lys | Ser | | | | | | |
| | | | 395 | | | | | 400 | | | | | | |

Arg Val Lys Asn Ile
            405

<210> SEQ ID NO 54
<211> LENGTH: 40
<212> TYPE: PRT
<213> ORGANISM: Artificial Sequence
<220> FEATURE:
<223> OTHER INFORMATION: ABP consensus
<220> FEATURE:
<221> NAME/KEY: misc_feature
<222> LOCATION: (1)..(1)
<223> OTHER INFORMATION: where X is K, G or A
<220> FEATURE:
<221> NAME/KEY: misc_feature
<222> LOCATION: (4)..(4)
<223> OTHER INFORMATION: where X is K, G or V
<220> FEATURE:
<221> NAME/KEY: misc_feature
<222> LOCATION: (6)..(6)
<223> OTHER INFORMATION: where X is R, G or A
<220> FEATURE:
<221> NAME/KEY: misc_feature
<222> LOCATION: (7)..(7)
<223> OTHER INFORMATION: where X is K, G or A
<220> FEATURE:
<221> NAME/KEY: misc_feature
<222> LOCATION: (28)..(28)
<223> OTHER INFORMATION: where X is R, G or V
<220> FEATURE:
<221> NAME/KEY: misc_feature
<222> LOCATION: (29)..(29)
<223> OTHER INFORMATION: where X is N, G or V
<220> FEATURE:
<221> NAME/KEY: misc_feature
<222> LOCATION: (34)..(34)
<223> OTHER INFORMATION: where X is K, G or V
<220> FEATURE:
<221> NAME/KEY: misc_feature
<222> LOCATION: (36)..(36)
<223> OTHER INFORMATION: where X is R, G or A
<220> FEATURE:
<221> NAME/KEY: misc_feature
<222> LOCATION: (38)..(38)
<223> OTHER INFORMATION: where X is K, G or A

<400> SEQUENCE: 54

Xaa Thr Phe Xaa Thr Xaa Xaa Ala Ser Ala Gln Ala Ser Leu Ala Ser
1               5                   10                  15

Lys Asp Lys Thr Pro Lys Ser Lys Ser Lys Lys Xaa Xaa Ser Thr Gln
            20                  25                  30

Leu Xaa Ser Xaa Val Xaa Asn Ile
        35                  40

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gly Gly Gly Ser Gly Gly Gly Gly Ser
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic

```
<400> SEQUENCE: 56

Gly Gly Gly Gly Ser Gly Gly Gly Gly Ser
1               5                   10

<210> SEQ ID NO 57
<211> LENGTH: 4
<212> TYPE: PRT
<213> ORGANISM: Artificial Sequence
<220> FEATURE:
<223> OTHER INFORMATION: Synthetic

<400> SEQUENCE: 57

Gly Gly Gly Ser
1

<210> SEQ ID NO 58
<211> LENGTH: 8
<212> TYPE: PRT
<213> ORGANISM: Artificial Sequence
<220> FEATURE:
<223> OTHER INFORMATION: Synthetic

<400> SEQUENCE: 58

Gly Gly Gly Ser Gly Gly Gly Ser
1               5

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Ile Thr Trp Gly Gly Asp Asn Thr Phe Tyr Ser Asn Ser Val Lys
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Synthetic

<400> SEQUENCE: 60

Asn Thr Glu Pro Val Leu Asp Ser Asp Gly Ser Tyr Phe Met Tyr Ser
1               5                   10                  15

Lys

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Ala Ser Ala Gln Ala Ser Leu Ala Ser Lys
1               5                   10

<210> SEQ ID NO 62
<211> LENGTH: 16
<212> TYPE: PRT
<213> ORGANISM: Artificial Sequence
<220> FEATURE:
```

```
<223> OTHER INFORMATION: Synthetic

<400> SEQUENCE: 62

Gly Leu Glu Trp Val Ala Thr Ile Asp Trp Gly Asp Gly Gly Thr Arg
1               5                   10                  15

<210> SEQ ID NO 63
<211> LENGTH: 13
<212> TYPE: PRT
<213> ORGANISM: Artificial Sequence
<220> FEATURE:
<223> OTHER INFORMATION: Synthetic

<400> SEQUENCE: 63

Ala Glu Asp Thr Ala Val Tyr Tyr Cys Ala Met Ala Arg
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic

<400> SEQUENCE: 64

Leu Val Phe Phe Ala Glu Asp Val Gly Ser Asn Lys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic

<400> SEQUENCE: 65

Ala Pro Trp Val Ser Thr Pro Thr Leu Val Glu Ala Ala Arg
1               5                   10

<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

Ile Leu Ile Ser
1
```